US012240815B2

(12) United States Patent
Silverman et al.

(10) Patent No.: US 12,240,815 B2
(45) Date of Patent: Mar. 4, 2025

(54) POTENT AND SELECTIVE HUMAN NEURONAL NITRIC OXIDE SYNTHASE INHIBITORS

(71) Applicant: Northwestern University, Evanston, IL (US)

(72) Inventors: Richard B. Silverman, Winnetka, IL (US); Ha T. Do, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/184,544

(22) Filed: Feb. 24, 2021

(65) Prior Publication Data

US 2021/0269400 A1    Sep. 2, 2021

Related U.S. Application Data

(63) Continuation of application No. PCT/US2020/019466, filed on Feb. 24, 2020.

(60) Provisional application No. 62/980,735, filed on Feb. 24, 2020.

(51) Int. Cl.
| | |
|---|---|
| *C07D 213/73* | (2006.01) |
| *C07D 401/06* | (2006.01) |
| *C07D 401/10* | (2006.01) |
| *C07D 413/10* | (2006.01) |

(52) U.S. Cl.
CPC ......... *C07D 213/73* (2013.01); *C07D 401/06* (2013.01); *C07D 401/10* (2013.01); *C07D 413/10* (2013.01)

(58) Field of Classification Search
CPC .. C07D 213/73; C07D 401/06; C07D 401/10; C07D 413/10
See application file for complete search history.

(56) References Cited

U.S. PATENT DOCUMENTS

| | | | | |
|---|---|---|---|---|
| 5,972,975 | A * | 10/1999 | Esser | A61K 31/44 514/217.08 |
| 7,317,021 | B2 * | 1/2008 | Fuchss | A61P 17/00 546/118 |
| 8,735,606 | B2 | 5/2014 | Silverman | |
| 8,829,187 | B1 | 9/2014 | Silverman | |
| 8,932,842 | B2 | 1/2015 | Silverman | |
| 9,090,589 | B2 | 7/2015 | Silverman | |
| 9,120,750 | B2 | 9/2015 | Silverman | |
| 9,212,144 | B2 | 12/2015 | Silverman | |
| 9,212,161 | B2 | 12/2015 | Silverman | |
| 9,242,957 | B2 | 1/2016 | Silverman | |
| 9,416,106 | B2 | 8/2016 | Silverman | |
| 9,663,468 | B2 | 5/2017 | Silverman | |
| 9,682,950 | B2 | 6/2017 | Silverman | |
| 9,701,661 | B2 | 7/2017 | Silverman | |
| 9,732,037 | B2 | 8/2017 | Silverman | |
| 9,758,507 | B2 | 9/2017 | Silverman | |
| 9,765,055 | B2 | 9/2017 | Silverman | |
| 9,783,500 | B2 | 10/2017 | Silverman | |
| 9,878,996 | B2 | 1/2018 | Silverman | |
| 9,951,014 | B2 | 4/2018 | Silverman | |
| 10,167,260 | B2 | 1/2019 | Silverman | |
| 10,759,791 | B2 | 9/2020 | Silverman | |
| 2013/0040359 | A1 | 2/2013 | Silverman | |
| 2014/0228578 | A1 | 8/2014 | Silverman | |
| 2014/0256016 | A1 | 9/2014 | Silverman | |
| 2015/0210644 | A1 | 7/2015 | Silverman | |
| 2015/0252020 | A1 | 9/2015 | Silverman | |
| 2016/0122302 | A1 | 5/2016 | Silverman | |
| 2016/0368877 | A1 | 12/2016 | Silverman | |
| 2017/0260165 | A1 | 9/2017 | Silverman | |
| 2017/0275278 | A1 | 9/2017 | Silverman | |
| 2017/0298021 | A1 | 10/2017 | Silverman | |
| 2020/0179368 | A1 | 6/2020 | Silverman | |
| 2020/0331910 | A1 | 10/2020 | Silverman | |
| 2020/0377481 | A1 | 12/2020 | Silverman | |
| 2021/0269400 | A1 | 9/2021 | Silverman | |

FOREIGN PATENT DOCUMENTS

WO    2017214286    12/2017

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html>.*
Winn, M. D. etal. Use of TLS parameters to model anisotropic displacements in macromolecular refinement. Acta Crystallographica Section D 2001, 57, 122-133.
Yung-Chi, C. et al. Relationship between the inhibition constant (KI) and the concentration of inhibitor which causes 50 per cent inhibition (150) of an enzymatic reaction. Biochemical Pharmacology 1973, 22, 3099-3108.
Adams, P. D.; et al. PHENIX: a comprehensive Python-based system for macromolecular structure solution. Acta Crystallographica Section D 2010, 66, 213-221.
Alderton, W. K.; et al. Nitric oxide synthases: structure, function and inhibition. Biochemical Journal 2001, 357, 593-615.
Banks, W. A. From blood-brain barrier to blood-brain interface: new opportunities for CNS drug delivery. Nature Reviews Drug Discovery 2016, 15, 275.

(Continued)

*Primary Examiner* — Rebecca L Anderson
(74) *Attorney, Agent, or Firm* — Quarles & Brady LLP

(57) ABSTRACT

Disclosed are 2-aminopyridine derivative compounds for use as inhibitors of nitric oxide synthase (NOS). In particular, the field of the invention relates to 2-aminopyridine derivative compounds for use as inhibitors of neuronal nitric oxide synthase (nNOS), which are formulated as pharmaceutical compositions for treating diseases and disorders associated with nNOS such as Alzheimer's, Parkinson's, and Huntington's diseases, and amyotrophic lateral sclerosis, cerebral palsy, stroke/ischemic brain damage, and migraine headaches.

23 Claims, 1 Drawing Sheet

(56) References Cited

OTHER PUBLICATIONS

Barbanti, P. et al. Drugs targeting nitric oxide synthase for migraine treatment. Expert Opinion on Investigational Drugs 2014, 23, 1141-1148.
Battye, T. G. G. et al. iMOSFLM: a new graphical interface for diffraction-image processing with MOSFLM. Acta Crystallographica Section D: Biological Crystallography 2011, 67, 271-281.
Bolanos, J. P. et al. Nitric oxide-mediated mitochondrial damage in the brain: Mechanisms and implications for neurodegenerative diseases. Journal of Neurochemistry 1997, 68, 2227-2240.
Cinelli, M. A. et al. Nitrile in the Hole: Discovery of a Small Auxiliary Pocket in Neuronal Nitric Oxide Synthase Leading to the Development of Potent and Selective 2-Aminoquinoline Inhibitors. Journal of Medicinal Chemistry 2017, 60, 3958-3978.
Cinelli, M. A. et al. Phenyl Ether- and Aniline-Containing 2-Aminoquinolines as Potent and Selective Inhibitors of Neuronal Nitric Oxide Synthase. Journal of Medicinal Chemistry 2015, 58, 8694-8712.
De La Torre, J. C. et al. Evidence that Alzheimer's disease is a microvascular disorder: the role of constitutive nitric oxide. Brain Research Reviews 2000, 34, 119-136.
Di, L. et al. Demystifying Brain Penetration in Central Nervous System Drug Discovery. Journal of Medicinal Chemistry 2013, 56, 2-12.
Do et al., "Optimization of Blood-Brain Barrier Permeability with Potent and Selective Human Neuronal Nitric Oxide Synthase Inhibitors Having a 2-Aminopyridine Scaffold," J. Med. Chem. 2019, 62, 5, 2690-2707.
Do, H. T. et al. Improvement of Cell Permeability of Human Neuronal Nitric Oxide Synthase Inhibitors Using Potent and Selective 2-Aminopyridine-Based Scaffolds with a Fluorobenzene Linker. Journal of Medicinal Chemistry 2017, 60, 9360-9375.
Drechsel, D. A. et al. Nitric oxide-mediated oxidative damage and the progressive demise of motor neurons in ALS. Neurotoxicity research 2012, 22, 251-264.
Emsley, P. et al. Coot: model-building tools for molecular graphics. Acta Crystallographica Section D 2004, 60, 2126-2132.
Evans, P. Scaling and assessment of data quality. Acta Crystallographica Section D 2006, 62, 72-82.
Feng, B. et al. In Vitro P-glycoprotein Assays to Predict the in Vivo Interactions of P-glycoprotein with Drugs in the Central Nervous System. Drug Metabolism and Disposition 2008, 36, 268-275.
Fischmann, T. O. et al. Structural characterization of nitric oxide synthase isoforms reveals striking active-site conservation. Nature Structural Biology 1999, 6, 233.
Fossetta, J. D. et al. Expression of human inducible nitric oxide synthase in *Escherichia coli*. FEBS Letters 1996, 379, 135-138.
Garthwaite, J. et al. Nitric Oxide Signaling in the Central Nervous System. Annual Review of Physiology 1995, 57, 683-706.
Gribkoff, V. K. et al. The need for new approaches in CNS drug discovery: Why drugs have failed, and what can be done to improve outcomes. Neuropharmacology 2017, 120, 11-19.
Hevel, J. M. et al. [25] Nitric oxide synthase assays. Methods in Enzymology 1994, 233, 250-258.
Hevel, J. M. et al. Purification of the inducible murine macrophage nitric oxide synthase. Identification as a flavoprotein. Journal of Biological Chemistry 1991, 266, 22789-91.
International Searching Authority. International Search Report and Written Opinion for application PCT/US2020/019466. Mailed on Nov. 19, 2020. 10 pages.
Ji, H. et al. Minimal Pharmacophoric Elements and Fragment Hopping, an Approach Directed at Molecular Diversity and Isozyme Selectivity. Design of Selective Neuronal Nitric Oxide Synthase Inhibitors. Journal of the American Chemical Society 2008, 130, 3900-3914.
Kabsch, W. XDS. Acta Crystallographica Section D: Biological Crystallography 2010, 66, 125-132.
Kang, S. et al. 2-Aminopyridines with a Truncated Side Chain To Improve Human Neuronal Nitric Oxide Synthase Inhibitory Potency and Selectivity. Journal of Medicinal Chemistry 2015, 58, 5548-5560.
Leber, A. et al. Characterization of Recombinant Human Endothelial Nitric-oxide Synthase Purified from the Yeast Pichia pastoris. Journal of Biological Chemistry 1999, 274, 37658-37664.
Li, H. et al. Crystal Structures of Zinc-free and -bound Heme Domain of Human Inducible Nitric oxide Synthase: Implications for Dimer Stability and Comparison With Endothelial Nitric-Oxide Synthase. Journal of Biological Chemistry 1999, 274, 21276-21284.
Li, H. et al. Electrostatic Control of Isoform Selective Inhibitor Binding in Nitric Oxide Synthase. Biochemistry 2016, 55, 3702-3707.
Li, H. et al. Structures of human constitutive nitric oxide synthases. Acta Crystallographica Section D 2014, 70, 2667-2674.
Liebschner, D. et al. Polder maps: improving OMIT maps by excluding bulk solvent. Acta Crystallographica. Section D, Structural Biology 2017, 73, 148-157.
Loscher, W. et al. Drug resistance in brain diseases and the role of drug efflux transporters. Nature Reviews Neuroscience 2005, 6, 591.
Maccallini, C. et al. Targeting neuronal nitric oxide synthase as a valuable strategy for the therapy of neurological disorders. Neural Regeneration Research 2016, 11, 1731-1734.
McCoy, A. J. et al. Phaser crystallographic software. Journal of Applied Crystallography 2007, 40, 658-674.
McPhillips, T. M. et al. Blu-Ice and the Distributed Control System: software for data acquisition and instrument control at macromolecular crystallography beamlines. Journal of Synchrotron Radiation 2002, 9, 401-406.
Moore, P. K. et al. Selective inhibitors of neuronal nitric oxide synthase—is no NOS really good NOS for the nervous system? Trends in Pharmacological Sciences 1997, 18, 204-211.
Mukherjee, P. et al. Development of nitric oxide synthase inhibitors for neurodegeneration and neuropathic pain. Chemical Society Reviews 2014, 43, 6814-6838.
Muller, J. et al. Tuning the predictive capacity of the PAMPA-BBB model. European Journal of Pharmaceutical Sciences 2015, 79, 53-60.
Muller, S. et al. An Improved One-pot Procedure for the Synthesis of Alkynes from Aldehydes. Synlett 1996, 1996, 521-522.
Murshudov, G. N. et al. Refinement of Macromolecular Structures by the Maximum-Likelihood Method. Acta Crystallographica Section D 1997, 53, 240-255.
Nutt, D. J. et al. CNS drug development in Europe—Past progress and future challenges. Neurobiology of Disease 2014, 61, 6-20.
Patil, A. G. et al. Validation of quinidine as a probe substrate for the in vitro P-gp inhibition assay in Caco-2 cell monolayer. European Journal of Drug Metabolism and Pharmacokinetics 2011, 36, 115.
Rankovic, Z. CNS Drug Design: Balancing Physicochemical Properties for Optimal Brain Exposure. Journal of Medicinal Chemistry 2015, 58, 2584-2608.
Roman, L. J. et al. High-level expression of functional rat neuronal nitric oxide synthase in *Escherichia coli*. Proceedings of the National Academy of Sciences 1995, 92, 8428-8432.
Silverman, R. B. Design of Selective Neuronal Nitric Oxide Synthase Inhibitors for the Prevention and Treatment of Neurodegenerative Diseases. Accounts of Chemical Research 2009, 42, 439-451.
St. Jean, D. J. et al. Mitigating Heterocycle Metabolism in Drug Discovery. Journal of Medicinal Chemistry 2012, 55, 6002-6020.
Torreilles, F. et al. Neurodegenerative disorders: the role of peroxynitrite. Brain Research Reviews 1999, 30, 153-163.
Uehara, T. et al. S-Nitrosylated protein-disulphide isomerase links protein misfolding to neurodegeneration. Nature 2006, 441, 513-517.
Wager, T. T. et al. Moving beyond Rules: The Development of a Central Nervous System Multiparameter Optimization (CNS MPO) Approach To Enable Alignment of Druglike Properties. ACS Chemical Neuroscience 2010, 1, 435-449.
Wang, H.-Y. et al. Potent and Selective Human Neuronal Nitric Oxide Synthase Inhibition by Optimization of the 2-Aminopyridine-

(56) References Cited

OTHER PUBLICATIONS

Based Scaffold with a Pyridine Linker. Journal of Medicinal Chemistry 2016, 59, 4913-4925.

* cited by examiner

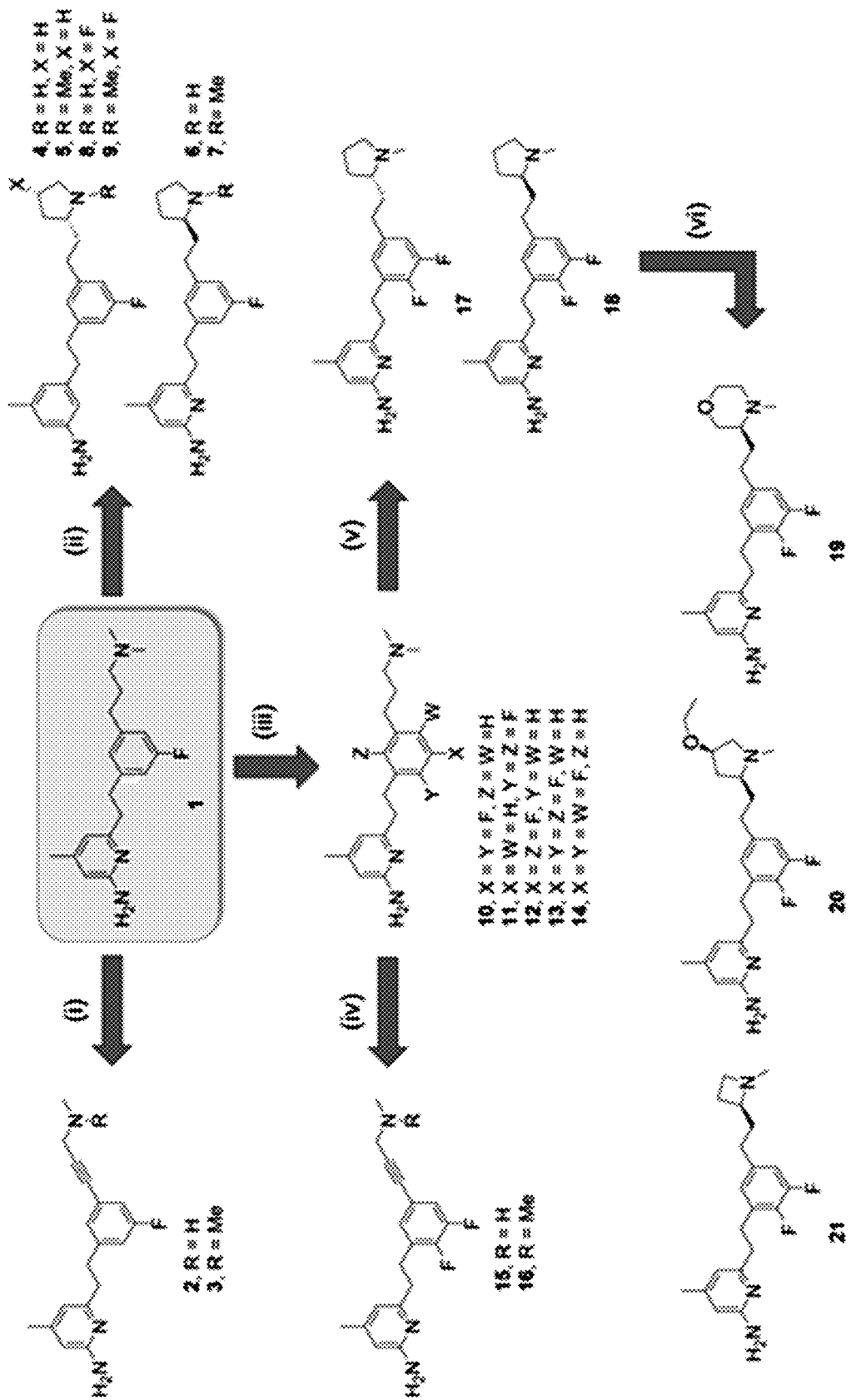

POTENT AND SELECTIVE HUMAN NEURONAL NITRIC OXIDE SYNTHASE INHIBITORS

CROSS-REFERENCED TO RELATED PATENT APPLICATIONS

This application claims the benefit of priority under 35 U.S.C. § 119(e) to U.S. Provisional Application No. 62/980,735, filed Feb. 24, 2020 and to International Application No. PCT/US2020/019466, filed Feb. 24, 2020, the contents of which are incorporated herein by reference in their entireties.

STATEMENT REGARDING FEDERALLY SPONSORED RESEARCH OR DEVELOPMENT

This invention was made with government support under grant GM049725 awarded by the National Institutes of Health. The government has certain rights in the invention.

BACKGROUND

The field of the invention relates to 2-aminopyridine derivative compounds for use as inhibitors of nitric oxide synthase. In particular, the field of the invention relates to 2-aminopyridine derivative compounds for use as inhibitors of nitric oxide synthase, which are formulated as pharmaceutical compositions for treatment of neurological diseases or disorders, which may include but are not limited to Alzheimer's, Parkinson's, and Huntington's diseases, amyotrophic lateral sclerosis, cerebral palsy, stroke/ischemic brain damage, and migraine headaches.

In some aspects, the disclosed subject matter relates to methods for treating neurological diseases and disorders and particularly neurodegenerative diseases. Neurodegenerative diseases, such as the commonly known Alzheimer's, Parkinson's, and Huntington's diseases, are characterized by a gradual degeneration and death of neurons in central nervous system (CNS), causing problems in muscular movements and mental functioning of patients. Despite acute medical needs, comprehensive treatments for these diseases are still very limited.[1,2] One of the most difficult challenges in CNS drug development is to effectively deliver therapeutic drugs into the human brain, mainly because of the presence of a blood brain barrier (BBB) located at the interface of blood vessels and brain tissues.[3] The BBB is composed of a layer of endothelial cells with tights junctions that prevents the access of external toxins, and therefore protects the brain and preserves its optimal physiological environment. This cell layer, however, also limits the access of valuable therapeutic drugs into the brain.[4] The major pathway for CNS drugs to cross the BBB is a passive diffusion through its lipid membrane. In addition to the tight junctions of endothelial cells, high expression levels of efflux transporters on the BBB, especially P-glycoprotein (P-gp), contributes greatly to the limited brain exposure of CNS drugs.[5] Consequently, it is necessary in CNS drug development to establish a strategy that includes a combination of increasing the passive permeability and lowering the P-gp mediated efflux.[3,6,7]

Neuronal nitric oxide synthase (nNOS) has been validated as a promising therapeutic target in the development of new treatments for neurodegenerative diseases.[8-10] In brain, nitric oxide (NO) produced by nNOS participates in neuronal transmissions.[11] The overproduction of NO in cells, however, is harmful. Particularly, excess NO formed by overactivated nNOS in CNS can cause excessive nitration and nitrosylation of proteins, leading to their misfolding and aggregation.[12] Additionally, the reaction of NO with superoxide anion creates a strongly oxidizing reagent, peroxinitrite, which damages DNA and causes lipid peroxidation. These processes lead to the nerve cell death and the impairment in neuronal transmissions.[13,14] Limiting NO production through inhibiting nNOS, therefore, could become an essential approach to protect neurons and potentially cure certain neurodegenerative diseases.[15,16]

nNOS is a homodimeric enzyme with each monomer containing one C-terminal reductase domain and one N-terminal oxygenase domain. The C-terminal reductase domain includes nicotinamide adenine dinucleotide phosphate (NADPH), flavin adenine dinucleotide (FAD), and flavin mononucleotide (FMN), whereas the N-terminal oxygenase domain includes a non-catalytic zinc, tetra-hydrobiopterin ($H_4B$), and a heme. These two domains are connected to each other by a calmodulin domain. When dimerization occurs, an electron flow is facilitated from the reductase domain to the oxygenase domain, through which L-Arg gets oxidized to L-Cit and NO is released.[15,17] Facilitating a molecule to compete with L-Arg binding at the active site of the enzyme is one of the fundamental approaches to inhibit nNOS.[16] The challenges of this task involve not only the potency of nNOS inhibitors, but also relate to their binding selectivity for nNOS over both eNOS and iNOS, the two isoforms that share very similar structural features to that of nNOS.[18,19] It is necessary to avoid over-inhibition of both eNOS and iNOS becasuse eNOS inhibition can result in cardiovascular failure while iNOS inhibition can cause a disruption in the immune system.[20]

In recent years, the inventors' efforts in achieving nNOS inhibitors with excellent potency and high isoform activity have led to a promising class of molecules bearing a 2-aminopyridine scaffold. Using this molecular scaffold, the inventors obtained nNOS inhibitors that exhibit excellent activity at concentrations in the <30 nM range.[15,21,22] The first generation of nNOS inhibitors bearing a 2-aminopyridine scaffold, however, showed poor predicted permeation through the BBB as revealed by very little Caco-2 permeability.[23] Recently, the inventors were able to improve the cell membrane permeability of 2-aminopyridine nNOS inhibitors, while retaining their high inhibitory activity for nNOS. The inventors previously identified a lead compound (1, FIG. 1), which shows an excellent potency and selectivity to human nNOS ($K_{i,\ hnNOS}$=30 nM; hnNOS/heNOS=2799) and displays an efflux ratio (ER) of 5.9 in Caco-2 assay.[24] In order to move forward in CNS drug development, the cell membrane permeability of 2-aminopyridine nNOS inhibitors must be further improved with a required ER of <2.5 for being a likely CNS(+) drug.[7,25]

SUMMARY

Disclosed are 2-aminopyridine compounds, pharmaceutical compositions and methods of treating diseases or disorders associated with nitric oxide synthase (NOS) activity. Diseases and disorders treated by the disclosed compounds, pharmaceutical compositions, and methods may include neurological diseases or disorders. Neurological diseases or disorders treated by the disclosed 2-aminopyridine compounds may include, but are not limited to neurodegenerative diseases such as Alzheimer's, Parkinson's, and Huntington's diseases, and amyotrophic lateral sclerosis, cerebral palsy, stroke/ischemic brain damage, and migraine headaches.

The disclosed compounds include derivatives of 2-aminopyridine. The disclosed compounds may have a formula (I) as follows:

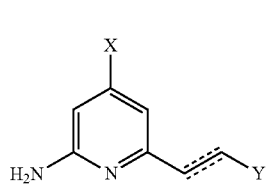
(I)

where X is hydrogen, $C_1$-$C_6$-alkyl (e.g., methyl), $C_1$-$C_6$-alkoxy (e.g., methoxy), halogen (e.g., fluoro or chloro), or haloalkyl (e.g., $CH_2F$, $CF_2H$, or $CF_3$),
≡ represents a single, double, or triple bond;
Y is substituted aryl (e.g., substituted phenyl) or substituted heteroaryl (e.g., substituted quinolinyl such as substituted quinolin-3-yl), wherein Y is substituted at one or more ring positions with halogen or a substituent having a formula —Z—$R^a$ and Y optionally is substituted at two or more ring positions with halogen (e.g., 2,3-difluoro-phenyl); or
Y has a formula —Z—$R^a$;
Z is selected from $C_1$-$C_6$-alkyl, $C_2$-$C_6$-alkenyl, and $C_2$-$C_6$-alkynyl;
$R^a$ is selected from amino, alkylamino (e.g., methylamino), dialkylamino (e.g., dimethylamino), or a 4-6 membered heterocycle which contains at least one nitrogen atom and which heterocycle is optionally substituted at one or more positions with alkyl (e.g., methyl), alkoxyl(e.g., ethoxy), or halogen (e.g. fluoro).

Also contemplated are salts of the disclosed compounds including pharmaceutically acceptable salts of the disclosed compounds. Also contemplated are solvates of the disclosed compounds.

Specifically, the disclosed compounds may have a formula (Ia):

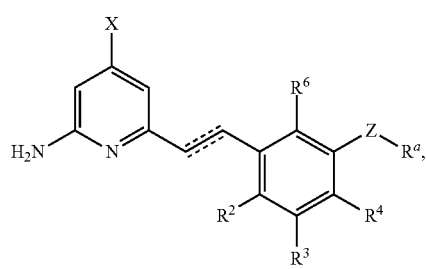
(Ia)

wherein X, Z, and $R^a$ are as defined above for formula (I) and $R^2$, $R^3$, $R^4$, and $R^6$, are each independently H or halogen (e.g., fluoro).

Specifically, the disclosed compounds may have a formula (Ib)

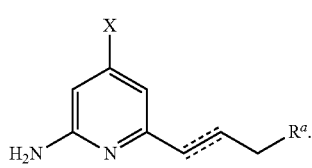
(Ib)

Specifically, the disclosed compounds may have a formula (II):

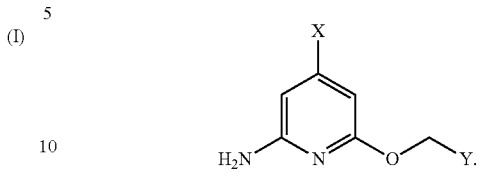
(II)

The disclosed compounds may be formulated as pharmaceutical compositions comprising the compounds or pharmaceutically acceptable salts thereof in a pharmaceutically acceptable carrier for use in treatment methods for a subject in need thereof. In some embodiments, the disclosed compounds and pharmaceutical compositions may be utilized to treat diseases or disorders associated with nitric oxide synthase activity. Particularly, the disclosed compounds and pharmaceutical compositions may be utilized to inhibit nitric oxide synthase in a subject in need thereof and treat diseases or disorders that are associated with nitric oxide synthase activity. In some embodiments, the disclosed compounds and pharmaceutical compositions may be utilized to treat neurological diseases or disorders in a subject in need thereof. Particularly, the disclosed compounds and pharmaceutical compositions may be utilized to treat Alzheimer's, Huntington's and/or Parkinson's disease, amyotrophic lateral sclerosis (ALS), cerebral palsy, and migraine headaches.

BRIEF DESCRIPTION OF THE FIGURES

FIG. 1. Structural modifications of compound 1. (i) enhancing rigidity by unsaturated C—C triple bond; (ii) enhancing lipophilicity and rigidity by incorporating pyrrolidine ring; (iii) enhancing lipophilicity by incorporating more fluorine into middle linker; (iv) difluorobenzene linker incorporated with unsaturated C—C triple bond; (v) difluorobenzene linker incorporated with pyrrolidine ring; (vi) modulating pKa of amino tail group.

DETAILED DESCRIPTION

The present invention is described herein using several definitions, as set forth below and throughout the application.

Definitions

The disclosed subject matter may be further described using definitions and terminology as follows. The definitions and terminology used herein are for the purpose of describing particular embodiments only and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or FIGURES, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with neuronal nitric oxide synthase (nNOS) activity and/or nitric oxide (NO) levels, such as a disease or disorder in which elevated NO levels are undesirable. The term "subject" may be used interchangeably with the terms "individual" and "patient" and includes human and non-human mammalian subjects.

Diseases and disorders associated with nNOS activity may include, but are not limited to neurological diseases and disorders. Neurological diseases and disorders may include, but are not limited to neurodegenerative diseases and disorders such as Alzheimer's, Parkinson's, and Huntington's diseases, and amyotrophic lateral sclerosis, cerebral palsy, stroke/ischemic brain damage, and migraine headaches.

The disclosed compounds may be utilized to modulate enzyme activities including, but not limited to nNOS activity. The term "modulate" should be interpreted broadly to include "inhibiting" enzyme activity and/or otherwise modulating enzyme activity.

New Chemical Entities

New chemical entities may be disclosed herein and may be described using terms known in the art and defined herein.

The term "alkyl" as used herein refers to a saturated straight or branched hydrocarbon, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively.

The term "alkylene" refers to a diradical of an alkyl group. An exemplary alkylene group is —$CH_2CH_2$—.

The term "haloalkyl" refers to an alkyl group that is substituted with at least one halogen, for example, —$CH_2F$, —$CHF_2$, —$CF_3$, —$CH_2CF_3$, —$CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively. A "cycloalkene" is a compound having a ring structure (e.g., of 3 or more carbon atoms) and comprising at least one double bond.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of a cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number or ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl orheteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "carboxy" or "carboxyl" as used herein refers to the radical —COOH or its corresponding salts, e.g. —COONa, etc.

The term "amide" or "amido" or "carboxamido" as used herein refers to a radical of the form —R$^1$C(O)N(R$^2$)—, —R$^1$C(O)N(R$^2$) R$^3$—, —C(O)N R$^2$ R$^3$, or —C(O)NH$_2$, wherein R$^1$, R$^2$ and R$^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Pharmaceutical Compositions

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that inhibits neuronal nitric oxide synthase may be administered as a single compound or in combination with another compound that inhibits neuronal nitric oxide synthase or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds, which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with neuronal nitric oxide synthase activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with neuronal nitric oxide synthase activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition, and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

2-Aminopyridine Derived Compounds and Uses Thereof

Disclosed herein are 2-aminopyridine derived compounds, pharmaceutical compositions comprising the compounds, and methods of using the compounds and pharmaceutical compositions for treating diseases and disorders associated with neuronal nitric oxide synthase activity. The disclosed compounds may include derivatives of 2-aminopyridine compounds or salts thereof having a formula as follows:

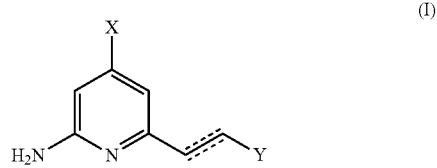

(I)

where X is hydrogen, $C_1$-$C_6$-alkyl (e.g., methyl), $C_1$-$C_6$-alkoxy (e.g., methoxy), halogen (e.g., fluoro or chloro), or haloalkyl (e.g., $CH_2F$, $CF_2H$, or $CF_3$), ≡≡≡ represents a single, double, or triple bond;

Y is substituted aryl (e.g., substituted phenyl) or substituted heteroaryl (e.g., substituted quinolinyl such as substituted quinolin-3-yl), wherein Y is substituted at one or more ring positions with halogen or a substituent having a formula —Z—$R^a$ and Y optionally is substituted at two or more ring positions with halo (e.g., 2,3-difluoro-phenyl); or Y has a formula —Z—$R^a$;

Z is selected from $C_1$-$C_6$-alkyl, $C_2$-$C_6$-alkenyl, and $C_2$-$C_6$-alkynyl;

$R^a$ is selected from amino, alkylamino (e.g., methylamino), dialkylamino (e.g., dimethylamino), or a 4-6 membered heterocycle which contains at least one nitrogen atom and which heterocycle is optionally substituted at one or more positions with alkyl (e.g., methyl), alkoxy (e.g., ethoxy), or halogen (e.g. fluoro).

Also contemplated are salts of the disclosed compounds including pharmaceutically acceptable salts of the disclosed compounds. Also contemplated are solvates of the disclosed compounds.

In some embodiments, the disclosed compounds may have $R^a$ selected from pyrrolidinyl (e.g., pyrrolidin-2-yl) which optionally is substituted at one or more positions with alkyl (e.g., 1-methyl-pyrrolidin-2-yl or 4-methyl-pyrrolidin-2-yl) or alkoxy (e.g., 4-ethoxy-pyrrolidin-2-yl) or halogen (e.g., 4-fluoro-pyrrolidin-2-yl) or both of alkyl and halogen (e.g., 4-fluoro-1-methylpyrrolidin-2-yl), azetinyl (e.g., azetin-2-yl), which optionally is substituted at one or more positions with alkyl (e.g., 1-methyl-azetin-2-yl), and morpholinyl (e.g., morpholin-3-yl) optionally substituted at one or more position with alkyl (e.g., 4-methyl-morpholin-3-yl), piperidinyl (e.g., piperidin-1-yl), or piperazinyl (e.g., piperazin-1-yl) optionally substituted at one or more positions with alkyl (e.g., 4-methyl-piperazin-1-yl).

In some embodiments, the disclosed compounds may have a formula (Ia):

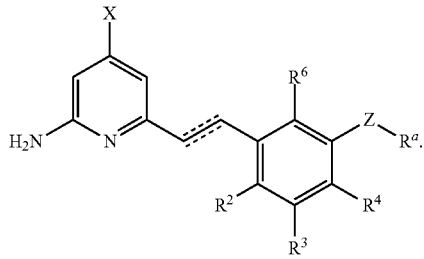

(Ia)

where X, Z, and $R^a$ are as defined for formula (I) and $R^2$, $R^3$, $R^4$, and $R^6$, are each independently H or halogen (e.g., fluoro). In some embodiments, $R^3$ is halogen (e.g., fluoro). In some embodiments, $R^2$ is halogen (e.g., fluoro). In some embodiments, $R^2$ is halogen (e.g., fluoro) and $R^3$ is halogen (e.g., fluoro). In some embodiments, Z is methyl, ethyl, or propyl. In some embodiments, $R^a$ is dimethylamino.

Specifically, the disclosed compounds may have a formula (Ib)

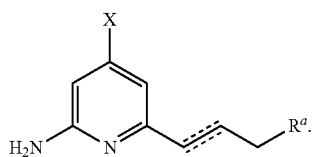

(Ib)

where X is defined as above and particularly where X is methyl; and where $R^a$ is defined as above and particular where $R^a$ is methylamino, dimethylamino, Specifically, the disclosed compounds may have a formula (II):

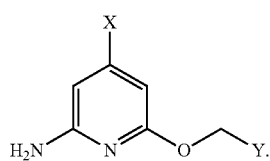

(II)

In some embodiments, the disclosed compounds may have a formula (Ic):

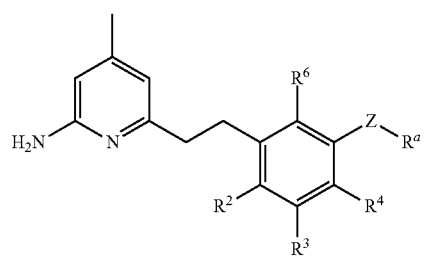

(Ic)

where Z and $R^a$ are as defined for formula (I) and $R^2$, $R^3$, $R^4$, and $R^6$, are each independently H or halogen (e.g., fluoro).

Specifically, the compounds disclosed herein may include compounds having a formula selected from:

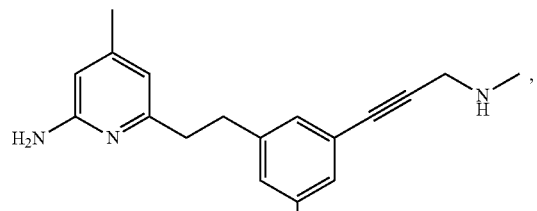

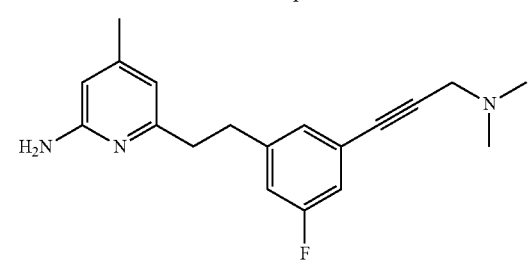

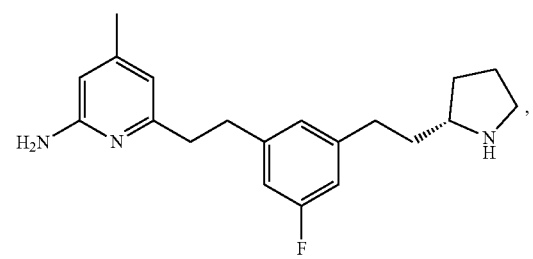

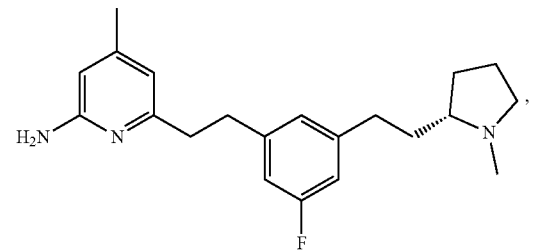

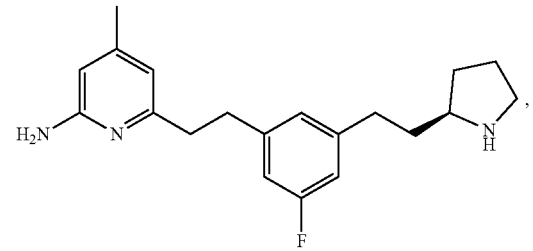

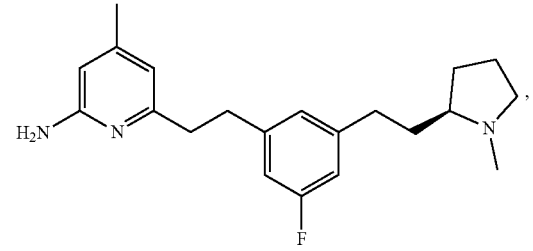

-continued
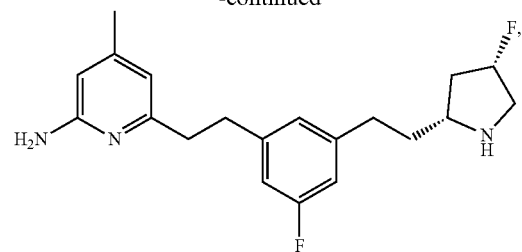
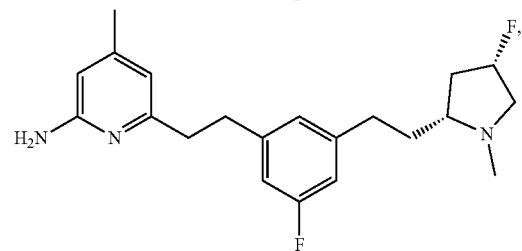
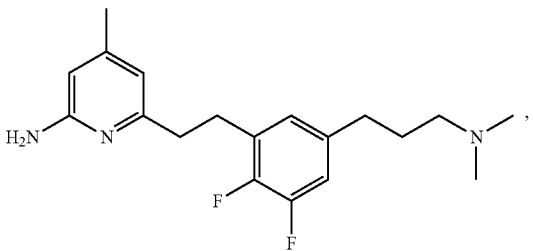
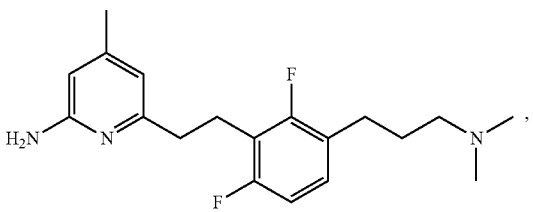
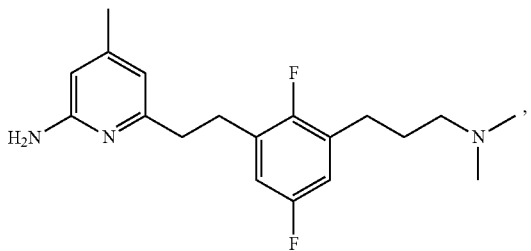
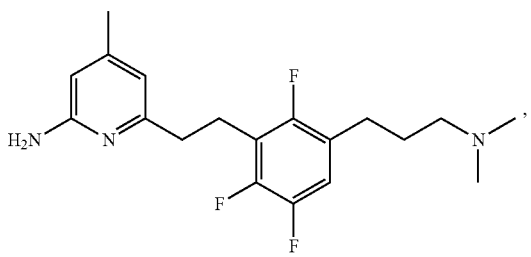
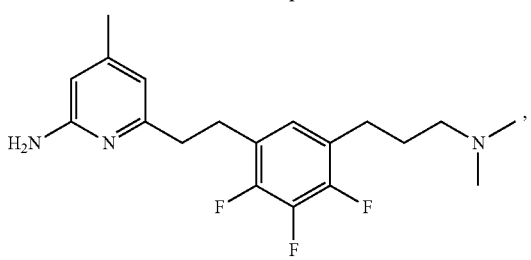
-continued
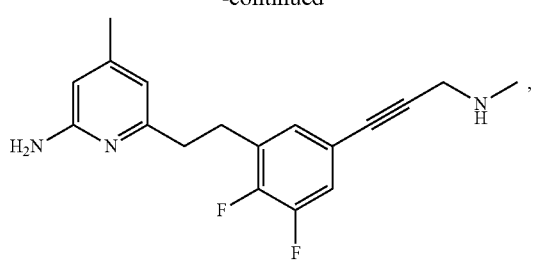
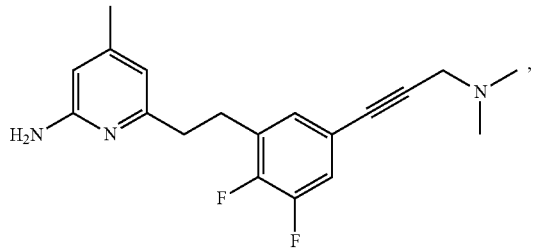
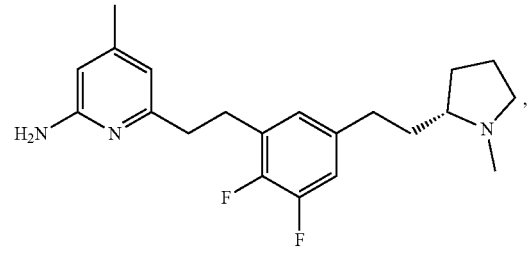
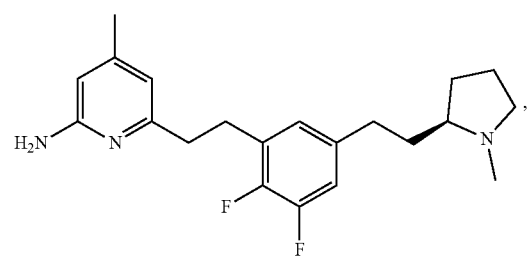
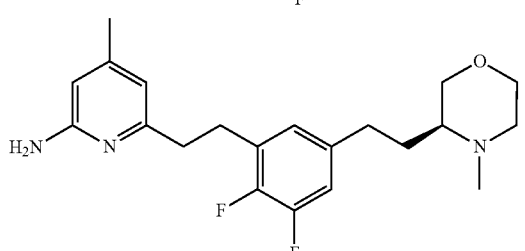
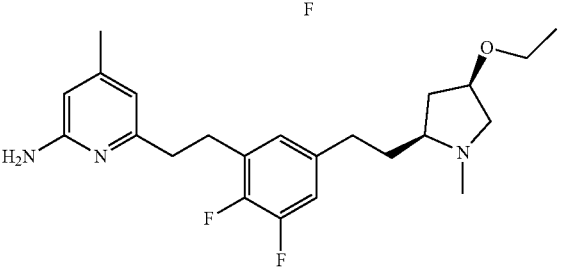

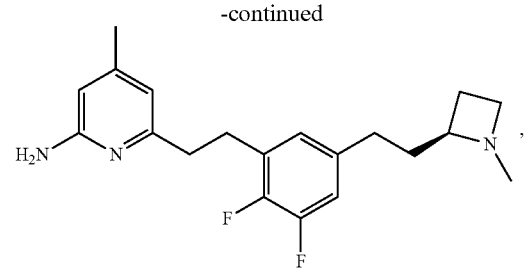
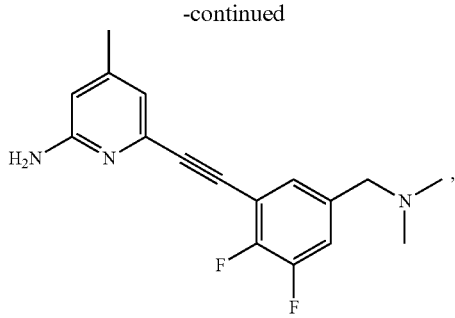
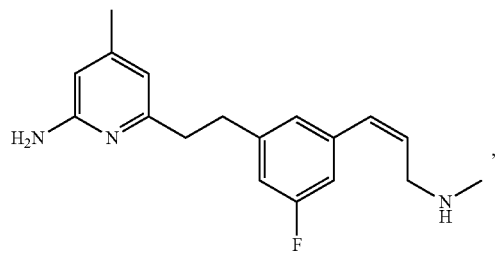
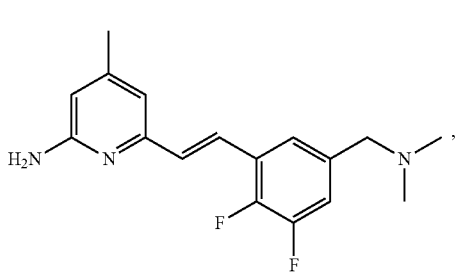
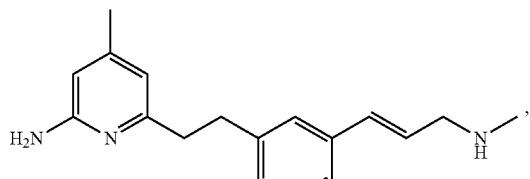
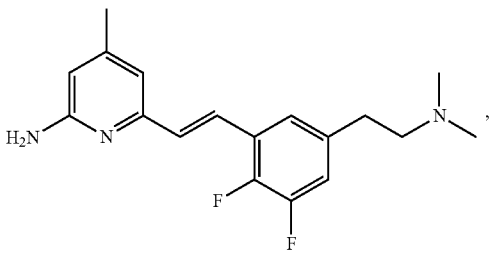
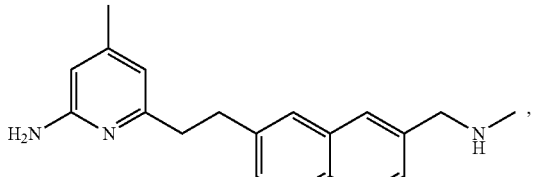
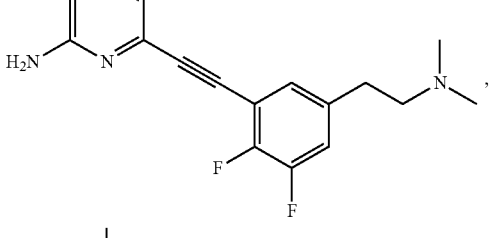
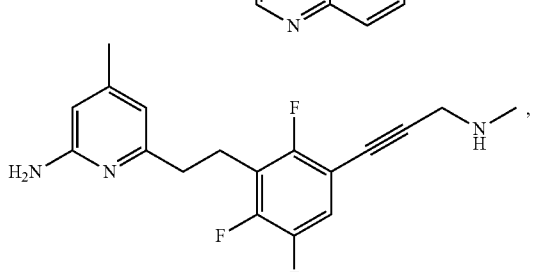
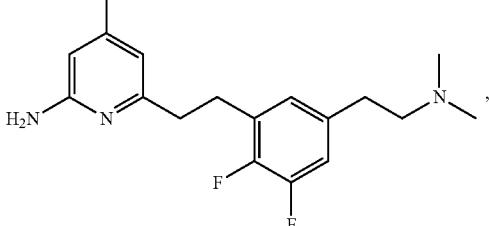
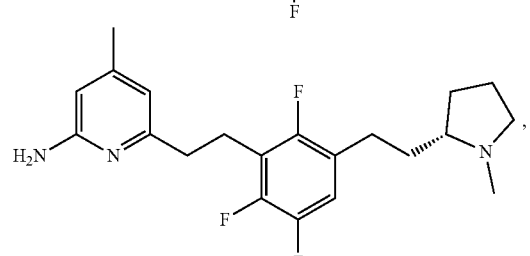
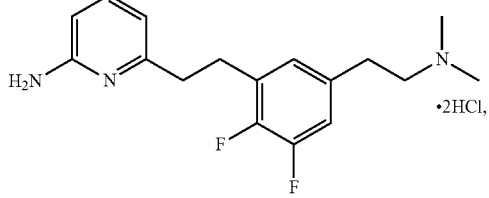
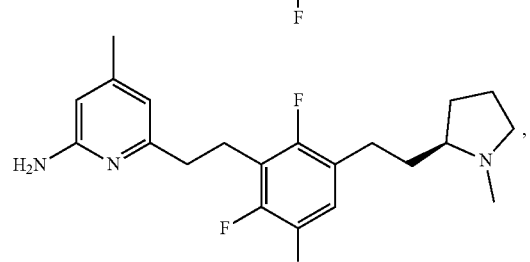

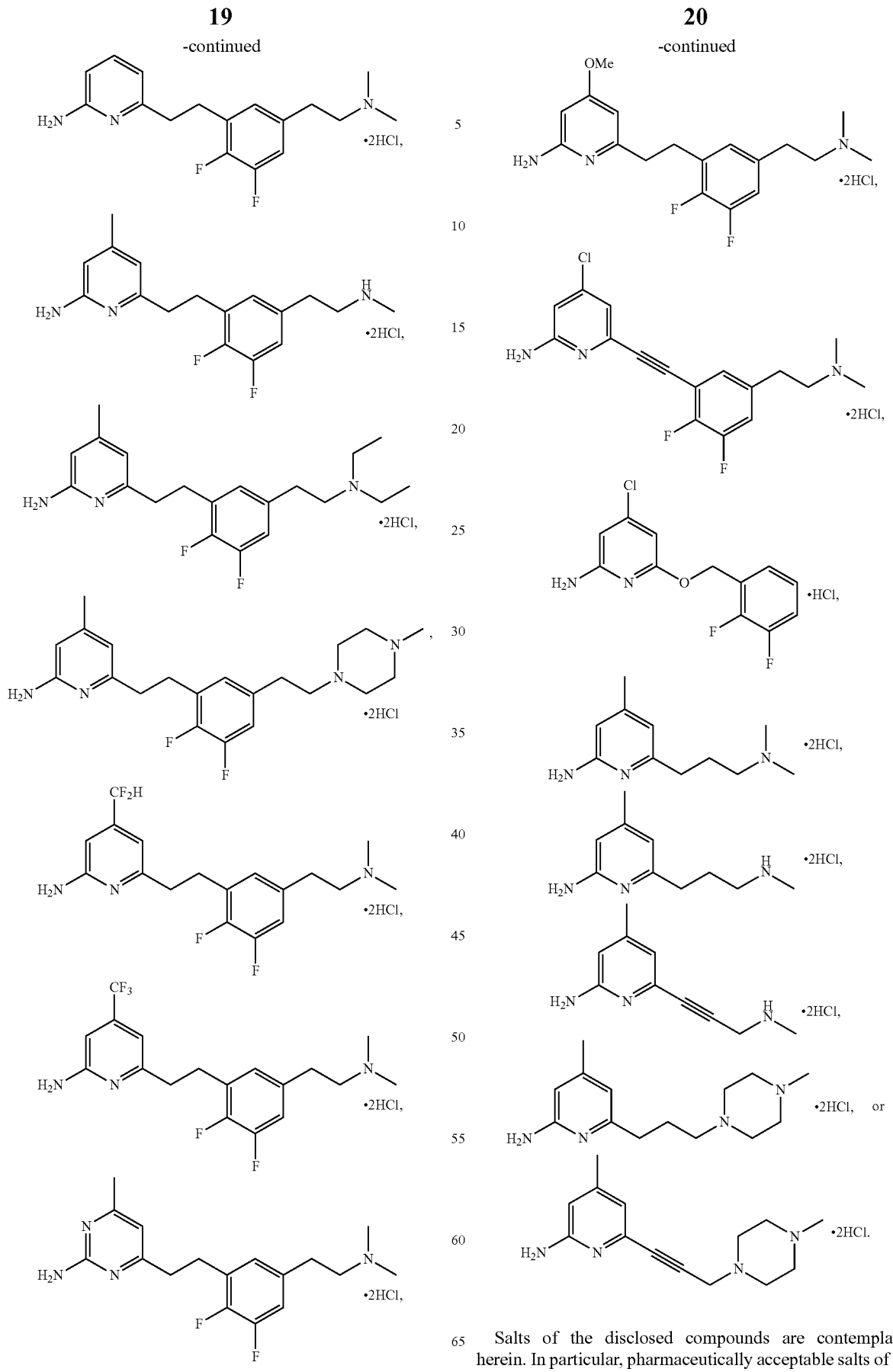
Salts of the disclosed compounds are contemplated herein. In particular, pharmaceutically acceptable salts of the disclosed compounds are contemplated herein.

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating diseases or disorders associated with nitric oxide synthase activity.

In some embodiments, the disclosed compounds and pharmaceutical compositions may be utilized for treating or preventing a subject having a disease or disorder associated with nitric oxide synthase (NOS), the method comprising administering o the subject the compounds and/or the pharmaceutical compositions. In these methods, the subject may be administered an amount of the compound sufficient to inhibit NOS activity.

In some embodiments, the disclosed compounds and pharmaceutical compositions may be utilized for treating or preventing neurodegenerative diseases or disorders in a subject in need thereof. In these methods, the subject may be administered an amount of the compound sufficient to inhibit NOS activity. In these methods, the subject may have a neurodegenerative disease or disorder selected from, but not limited to, Alzheimer's disease, Huntington's disease, Parkinson's disease, amyotrophic lateral sclerosis (ALS), cerebral palsy, and migraine headaches.

In some embodiments, the disclosed compounds and pharmaceutical compositions may be utilized for inhibiting NOS in a subject in need thereof. In these methods, the subject may be administered an amount of the compound sufficient to inhibit NOS activity.

In some embodiments, the NOS inhibited by the disclosed compounds is a neuronal NOS. In some embodiments, the disclosed compounds have a $K_i$ for human nNOS which is less than about of 100 nM, 90 nM, 80 nM, 70 nM, 60 nM, 50 nM, 40 nM, 30 nM, 20 nM, 10 nM, 5 nM, 1 nM, 0.5 nM, 0.1 nM or lower.

In some embodiments, the NOS inhibited by the disclosed compounds is a neuronal NOS which is inhibited selectively versus iNOS. In some embodiments, the compounds exhibit a selectivity for nNOS versus iNOS (n/i) which is at least about 10, 20, 30, 40, 50, 60, 70, 80, 90, 100 or higher.

In some embodiments, the NOS inhibited by the disclosed compounds is a neuronal NOS which is inhibited selectively versus eNOS. In some embodiments, the compounds exhibit a selectivity for nNOS versus eNOS (n/e) which is at least about 100, 200, 300, 400, 500, 600, 700, 800, 900, 1000, 1100, 1200, 1300, 1400, 1500, or higher.

In some embodiments, the NOS inhibited by the disclosed compounds is a neuronal NOS present in the brain of a subject in need thereof. In these methods, the disclosed compounds and preferably exhibit an effective permeability ($P_e$) for the blood brain barrier of at least about $5 \times 10^{-6}$ cm/s, $6 \times 10^{-6}$ cm/s, $7 \times 10^{-6}$ cm/s, $8 \times 10^{-6}$ cm/s, $9 \times 10^{-6}$ cm/s, $10 \times 10^{-6}$ cm/s, $11 \times 10^{-6}$ cm/s, $12 \times 10^{-6}$ cm/s, $13 \times 10^{-6}$ cm/s, $14 \times 10^{-6}$ cm/s, $15 \times 10^{-6}$ cm/s, $16 \times 10^{-6}$ cm/s, $17 \times 10^{-6}$ cm/s, $18 \times 10^{-6}$ cm/s, $19 \times 10^{-6}$ cm/s, or $20 \times 10^{-6}$ cm/s.

ILLUSTRATIVE EMBODIMENTS

The following embodiments are illustrative and should not be interpreted to limit the scope of the claimed subject matter.

Embodiment 1. A compound of a formula (I) or a salt or solvate thereof:

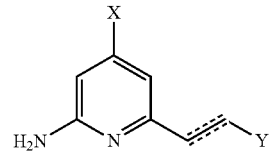

(I)

where X is hydrogen, $C_1$-$C_6$-alkyl (e.g., methyl), $C_1$-$C_6$-alkoxy (e.g., methoxy), halogen (e.g., fluoro or chloro), or haloalkyl (e.g., $CF_2H$ or $CF_3$), ===== represents a single, double, or triple bond;

Y is substituted aryl (e.g., substituted phenyl) or substituted heteroaryl (e.g., substituted quinolinyl such as substituted quinolin-3-yl), wherein Y is substituted at one or more ring positions with halogen or a substituent having a formula —Z—$R^a$ and Y optionally is substituted at two or more ring positions with halo (e.g., 2,3-difluoro-phenyl); or Y has a formula —Z—$R^a$;

Z is selected from $C_1$-$C_6$-alkyl, $C_2$-$C_6$-alkenyl, and $C_2$-$C_6$-alkynyl;

$R^a$ is selected from amino, alkylamino (e.g., methylamino), dialkylamino (e.g., dimethylamino), or a 4-6 membered heterocycle which contains at least one nitrogen atom and which heterocycle is optionally substituted at one or more positions with alkyl (e.g., methyl), alkoxy (e.g., ethoxy), or halogen (e.g. fluoro).

Embodiment 2. The compound of embodiment 1, wherein $R^a$ is selected from pyrrolidinyl (e.g., pyrrolidin-2-yl) which optionally is substituted at one or more positions with alkyl (e.g., 1-methyl-pyrrolidin-2-yl or 4-methyl-pyrrolidin-2-yl) or alkoxy (e.g., 4-ethoxy-pyrrolidin-2-yl) or halogen (e.g., 4-fluoro-pyrrolidin-2-yl) or both of alkyl and halogen (e.g., 1-methyl-4-fluoropyrrolidin-2-yl), azetinyl (e.g., azetin-2-yl) which optionally is substituted at one or more positions with alkyl (e.g., 1-methyl-azetin-2-yl), morpholinyl (e.g., morpholin-3-yl) optionally substituted at one or more position with alkyl (e.g., 4-methyl-morpholin-3-yl), piperidinyl (e.g., piperidin-1-yl), or piperazinyl (e.g., piperazin-1-yl) optionally substituted with alkyl (e.g., 4-methylpiperazin-1-yl).

Embodiment 3. The compound of embodiment 1 having a formula (Ia):

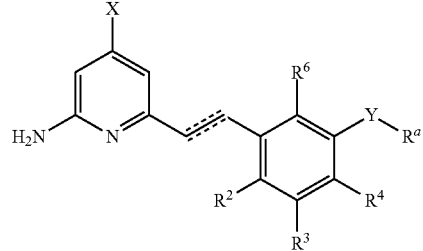

(Ia)

wherein $R^2$, $R^3$, $R^4$, and $R^6$, are each independently H or halogen (e.g., fluoro).

Embodiment 4. The compound of embodiment 3, wherein $R^3$ is halogen (e.g., fluoro).

Embodiment 5. The compound of embodiment 3 or 4, wherein $R^2$ is halogen (e.g., fluoro).

Embodiment 6. The compound of embodiment 3, wherein $R^2$ is halogen (e.g., fluoro) and $R^3$ is halogen (e.g., fluoro).

Embodiment 7. The compound of any of the foregoing embodiments wherein Z is methyl, ethyl, or propyl.

Embodiment 8. The compound of any of the foregoing embodiment wherein $R^a$ is dimethylamino.

Embodiment 9. The compound of can of the foregoing embodiments of a formula (Ib):

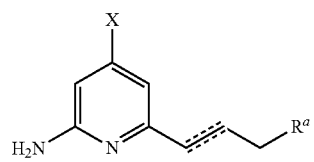

(Ib)

where X is defined as above and particularly where X is methyl; and where $R^a$ is defined as above and particular where $R^a$ is methylamino, dimethylamino.

Embodiment 10. A compound having a formula II:

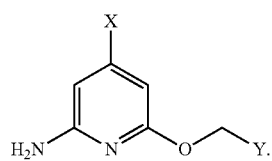

(II)

Embodiment 11. The compound of any of the foregoing embodiments of a formula:

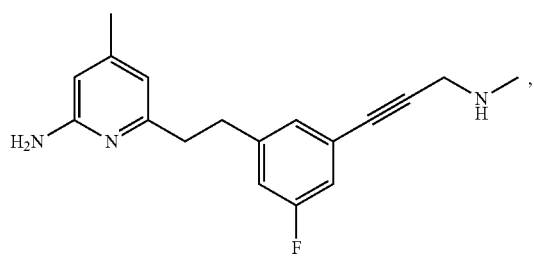

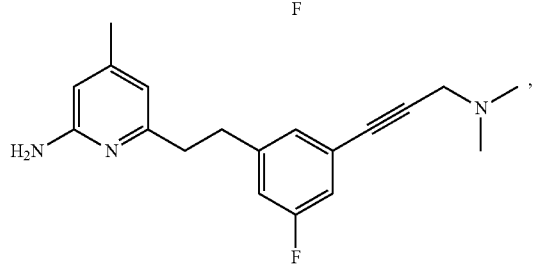

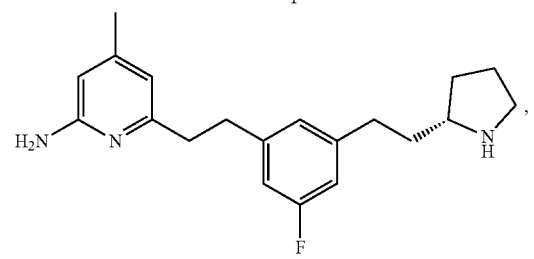

-continued

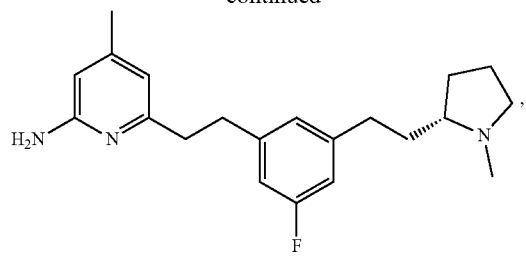

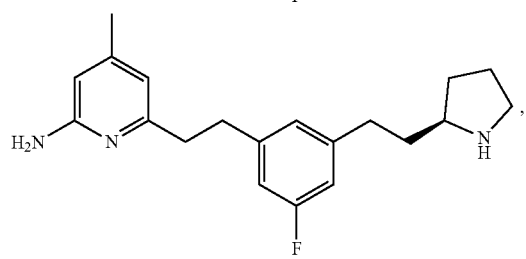

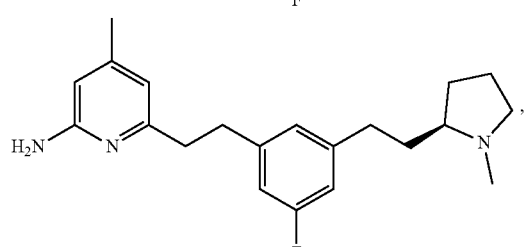

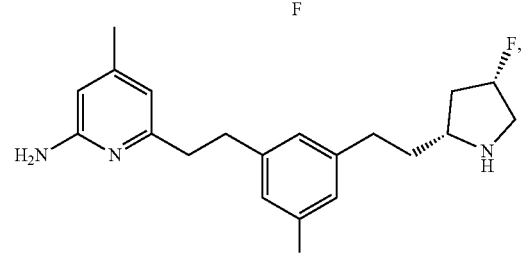

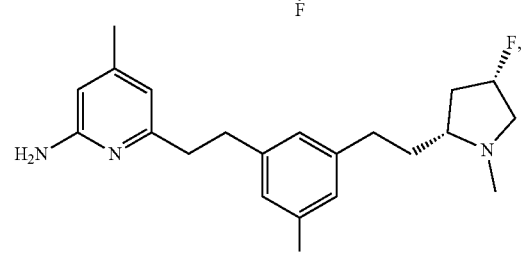

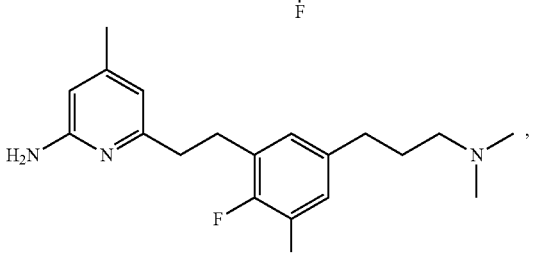

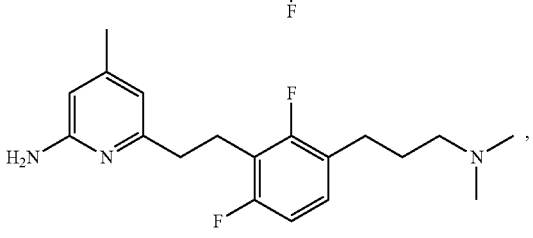

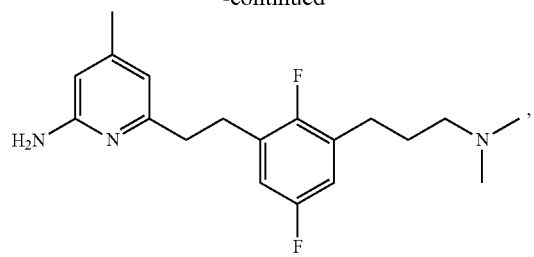
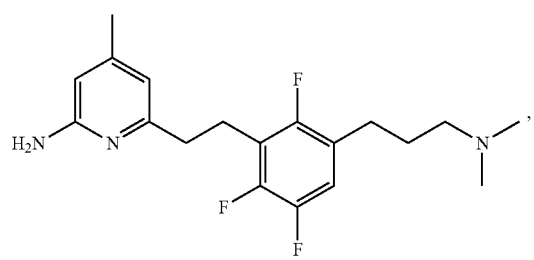
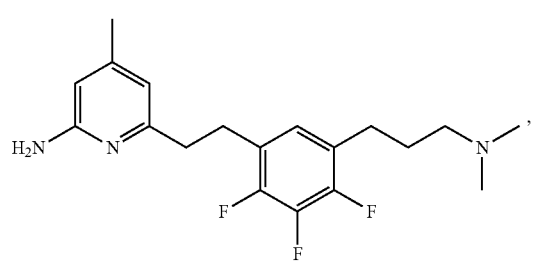
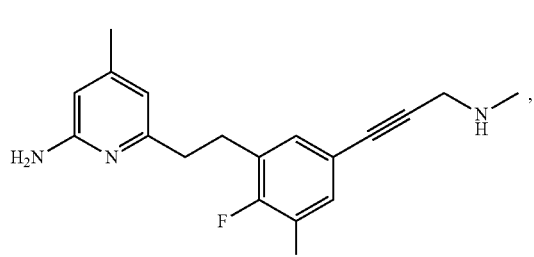
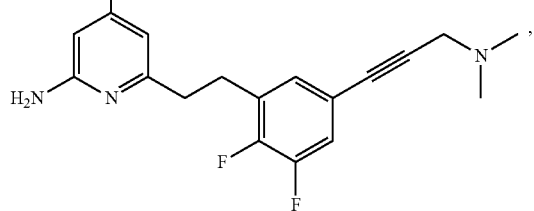
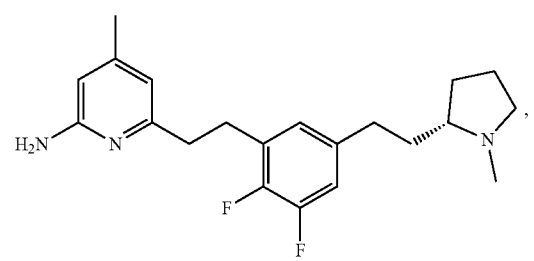
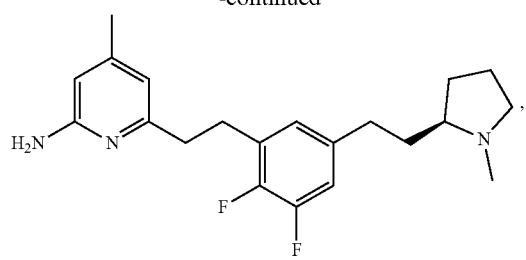
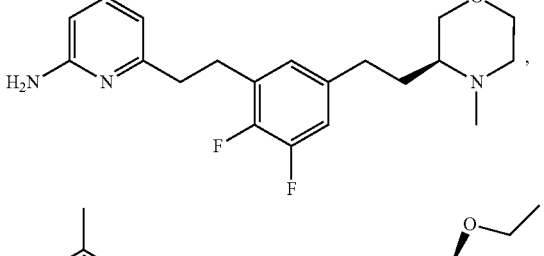
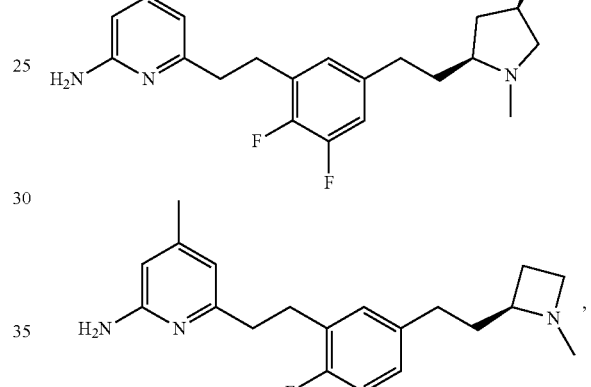
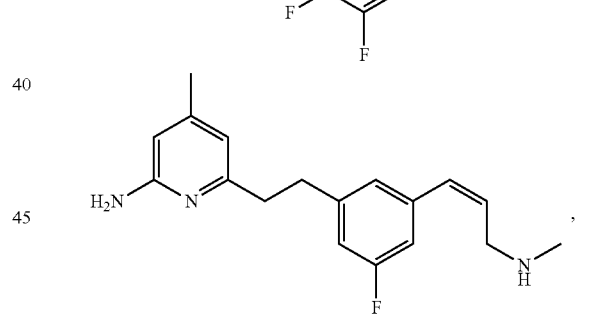
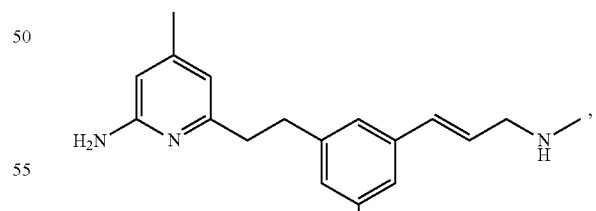
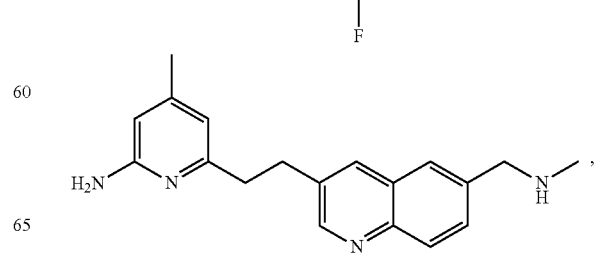

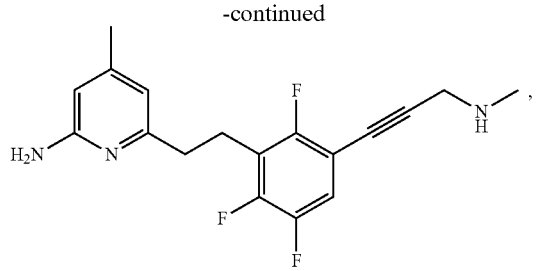
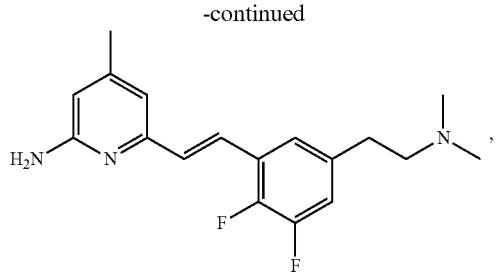
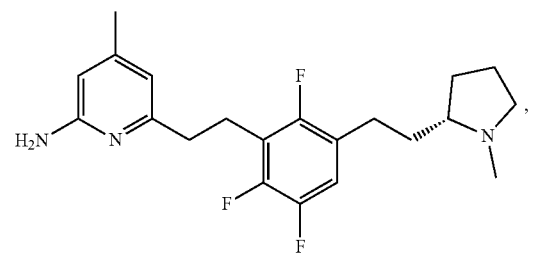
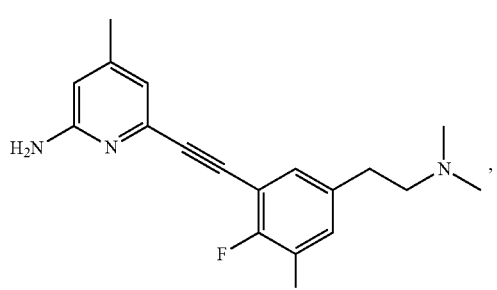
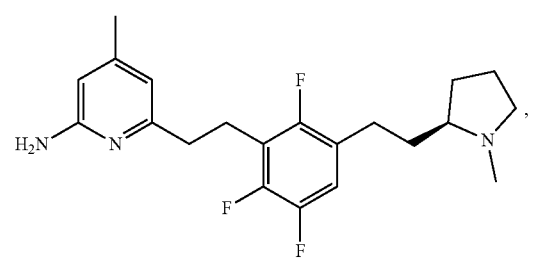
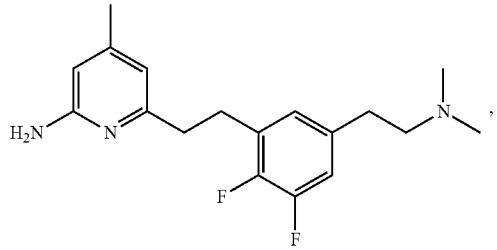
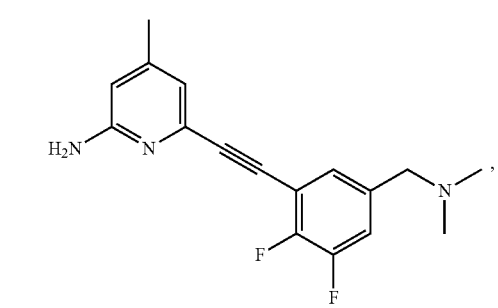
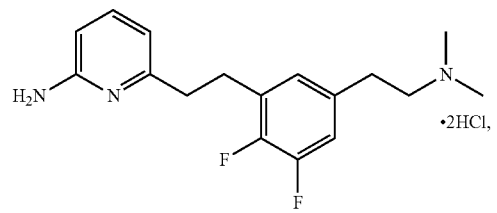
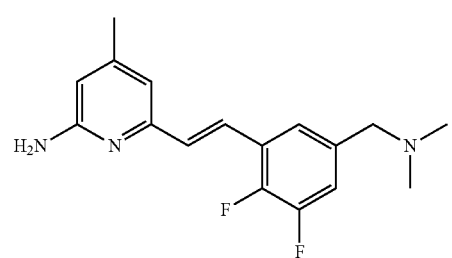
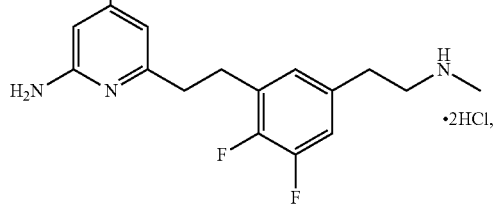
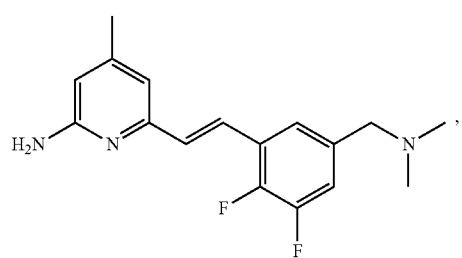
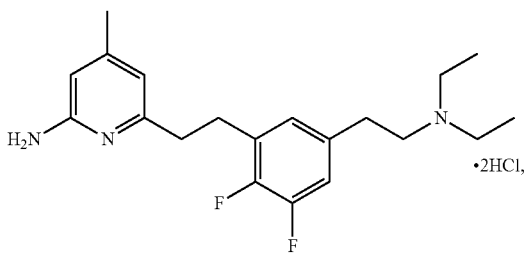

-continued

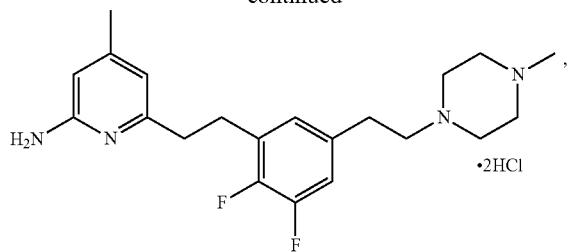

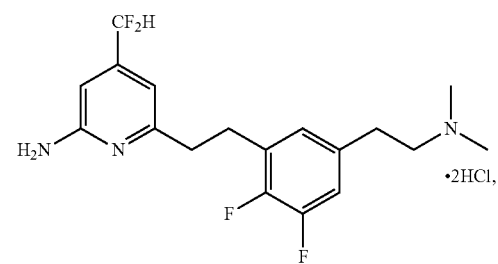

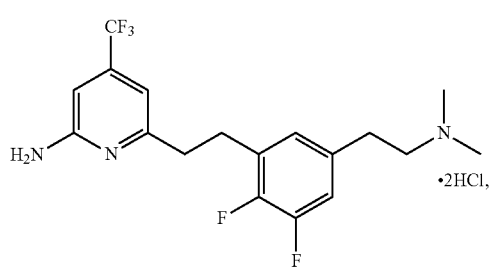

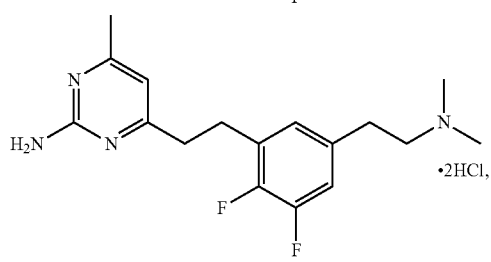

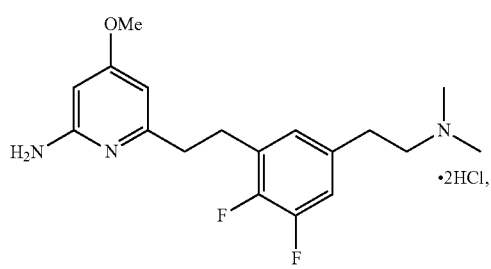

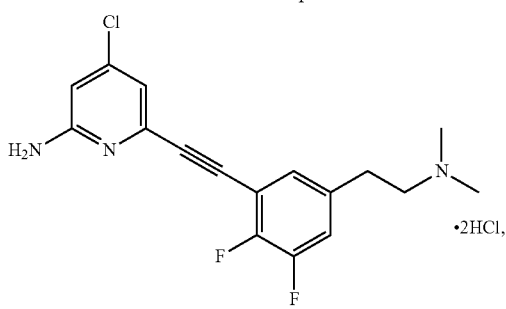

-continued

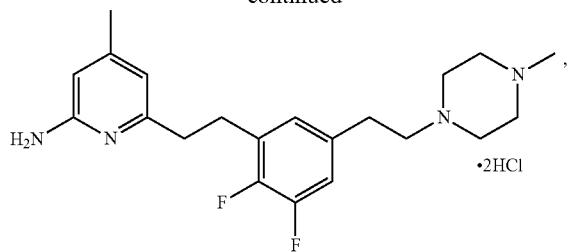

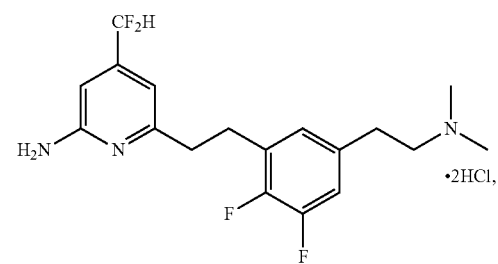

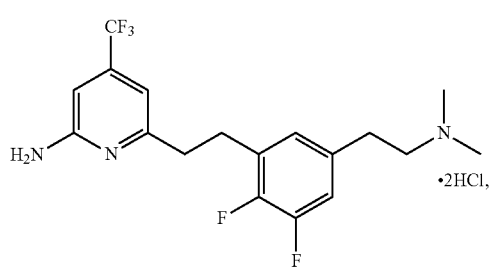

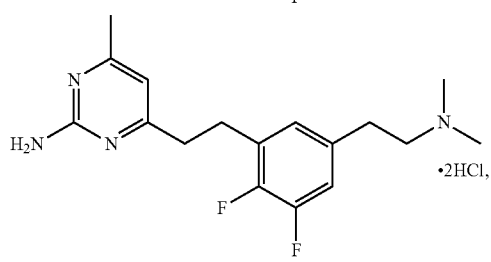

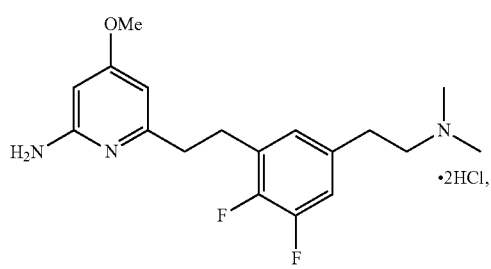

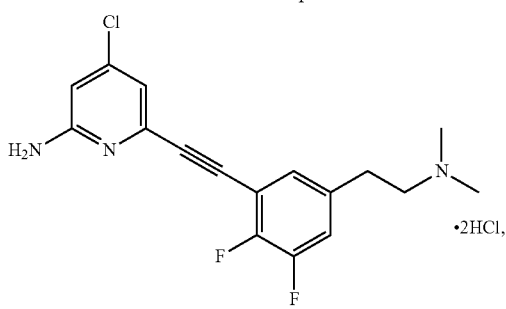

Embodiment 12. The compound of any of the foregoing embodiments, wherein the compound has an effective permeability $P_e$ for the blood brain barrier of at least about $5\times10^{-6}$ cm/s, $6\times10^{-6}$ cm/s, $7\times10^{-6}$ cm/s, $8\times10^{-6}$ cm/s, $9\times10^{-6}$ cm/s, $10\times10^{-6}$ cm/s, $11\times10^{-6}$ cm/s, $12\times10^{-6}$ cm/s, $13\times10^{-6}$ cm/s, $14\times10^{-6}$ cm/s, $15\times10^{-6}$ cm/s, $16\times10^{-6}$ cm/s, $17\times10^{-6}$ cm/s, $18\times10^{-6}$ cm/s, $19\times10^{-6}$ cm/s, or $20\times10^{-6}$ cm/s.

Embodiment 13. The compound of any of the foregoing embodiments, wherein the compound has a selectivity for nNOS versus iNOS of at least about 30.

Embodiment 14. The compound of any of the foregoing embodiments, wherein the compound has a selectivity for nNOS versus eNOS of at least about 1000.

Embodiment 15. A pharmaceutical composition comprising the compound of any of the foregoing embodiments and a pharmaceutically acceptable carrier.

Embodiment 16. A method of treating or preventing a disease or disorder associated with nitric oxide synthase in a subject in need thereof, the method comprising administering to the subject the compound of any of embodiments 1-14 or the pharmaceutical composition of embodiment 15.

Embodiment 17. The method of embodiment 16, wherein the disease or disorder is a neurodegenerative disease or disorder.

Embodiment 18. The method of embodiment 16, wherein the disease or disorder is Alzheimer's disease.
Embodiment 19. The method of embodiment 16, wherein the disease or disorder is Huntington's disease.
Embodiment 20. The method of embodiment 16, wherein the disease or disorder is Parkinson's disease.
Embodiment 21. The method of embodiment 16, wherein the disease or disorder is amyotrophic lateral sclerosis (ALS).
Embodiment 22. The method of embodiment 16, wherein the disease or disorder is cerebral palsy.
Embodiment 223. The method of embodiment 16, wherein the disease or disorder is a migraine headache.
Embodiment 24. A method of inhibiting nitric oxide synthase (NOS) in a cell, the method comprising contacting the cell with any of the compounds of embodiments 1-14.

EXAMPLES

The following Examples are illustrative and are not intended to limit the scope of the claimed subject matter.

Example 1

Title—Optimization of Blood Brain Barrier Permeability with Reduced P-Glycoprotein Substrate Liability on Potent and Selective Human Neuronal Nitric Oxide Synthase Inhibitors Bearing 2-Aminopyridine Scaffold for CNS Drug Development Reference is made to the manuscript: Do et al., "Optimization of Blood-Brain Barrier Permeability with Potent and Selective Human Neuronal Nitric Oxide Synthase Inhibitors Having a 2-Aminopyridine Scaffold," J. Med. Chem. 2019, 62, 5, 2690-2707, published Feb. 25, 2019, the content of which is incorporated herein by reference in its entirety.

Neurodegenerative diseases, such as the commonly known Alzheimer's, Parkinson's, and Huntington's diseases, are characterized by a gradual degeneration and death of neurons in central nervous system (CNS), causing problems in muscular movements and mental functioning of patients. Despite acute medical needs, comprehensive treatments for these diseases are still very limited.[1,2] One of the most difficult challenges in CNS drug development is to effectively deliver therapeutic drugs into the human brain, mainly because of the presence of a blood brain barrier (BBB) located at the interface of blood vessels and brain tissues.[3] The BBB is composed of a layer of endothelial cells with tights junctions that prevents the access of external toxins, and therefore protects the brain and preserves its optimal physiological environment. This cell layer, however, also limits the access of valuable therapeutic drugs into the brain.[4] The major pathway for CNS drugs to cross the BBB is a passive diffusion through its lipid membrane. In addition to the tight junctions of endothelial cells, high expression levels of efflux transporters on the BBB, especially P-glycoprotein (P-gp), contributes greatly to the limited brain exposure of CNS drugs.[5] Consequently, it necessitates in CNS drug development to establish a strategy consisting of a combination between increasing the passive permeability and lowering the P-gp mediated efflux.[3,6,7]

Neuronal nitric oxide synthase (nNOS) has been validated as a promising therapeutic target in the development of new treatments for neurodegenerative diseases.[8-10] In brain, nitric oxide (NO) produced by nNOS participates in neuronal transmissions.[11] The overproduction of NO in cells, however, is harmful. Particularly, excess NO formed by overactivated nNOS in CNS can cause excessive nitration and nitrosylation of proteins, leading to their misfolding and aggregation.[12] Additionally, the reaction of NO with superoxide anion creates a strongly oxidizing reagent, peroxinitrite, which damages DNA and causes lipid peroxidation. These processes lead to the nerve cell death and the impairment in neuronal transmissions.[13,14] Limiting NO production through inhibiting nNOS, therefore, could become an essential approach to protect neurons and potentially cure certain neurodegenerative diseases.[15,16]

nNOS is a homodimeric enzyme with each monomer containing of one C-terminal reductase domain and one N-terminal oxygenase domain. The C-terminal reductase domain consists of nicotinamide adenine dinucleotide phosphate (NADPH), flavin adenine dinucleotide (FAD), and flavin mononucleotide (FMN), whereas the N-terminal oxygenase domain contains a non-catalytic zinc, tetra-hydrobiopterin ($H_4B$), and a heme. These two domains are connected to each other by a calmodulin domain. When a dimerization happens, an electron flow is facilitated from the reductase domain to the oxygenase domain, at which L-Arg gets oxidized to L-Cit and NO is released.[15,17] Facilitating a molecule to compete with L-Arg binding at the active site of the enzyme is one of the fundamental approaches to inhibit nNOS.[16] The challenges of this task not only involve in the potency of inhibitors, but also relate to their binding selectivity for nNOS over both eNOS and iNOS, the two isoforms that share very similar structural features to that of nNOS.[18,19] It is necessary to avoid over-inhibition of these two NOS isoforms since eNOS inhibition can result in cardiovascular failure while iNOS inhibition can cause a disruption in the immune system.[20]

In recent years, our efforts in achieving nNOS inhibitors with excellent potency and high isoform activity have led to a promising class of molecules bearing a 2-aminopyridine scaffold. Using this molecular scaffold, we have obtained nNOS inhibitors that exhibit excellent activity at concentrations in the sub-30-nM range.[15,21,22] Our first generation of nNOS inhibitors bearing 2-aminopyridine scaffold, however, showed poor predicted permeation through the BBB as revealed by very little Caco-2 permeability.[23] Recently, we have been able to improve the cell membrane permeability of our 2-aminopyridine nNOS inhibitors, while retaining their high inhibitory activity. In our previous report, we obtained a new lead compound (1, FIG. 1), which shows an excellent potency and selectivity to human nNOS ($K_{i\ hnNOS}$=30 nM; hnNOS/heNOS=2799) and displays an efflux ratio (ER) of 5.9 in Caco-2 assay.[24] In order to move forward in CNS drug development, the cell membrane permeability of these 2-aminopyridine nNOS inhibitors must be further improved with a required ER of <2.5 for being a likely CNS(+) drug.[7,25]

In this contribution, we report our optimization toward improving the cell membrane permeability and reducing the P-gp substrate liability of 2-aminopyridine nNOS inhibitors, using 1 as the lead compound for numerous chemical modifications. Insights into understanding the structural effects on the activity and permeability of analogs have been obtained through various medicinal chemistry approaches, including enhancing the lipophilicity and rigidity of new analogs, along with modulating the pKa of basic amino groups within the molecules (FIG. 1). These structural modifications have been centralized on enhancing the disposition of nNOS inhibitors into the brain while preserving their potency and selectivity comparable to those of 1. Moreover, in this work, we aim, for the first time, to investigate the inhibition studies of potential compounds using all human NOS isoforms, which helps to provide not only a direct comparison in isoform selectivity but also more robust data for clinical studies if any of the studied nNOS inhibitors could be advanced to a later stage of drug development.

Structural modifications of 1 (FIG. 1) was first carried out on the tail chain where an unsaturated C—C triple bond is incorporated to new analogs (compounds 2 and 3) to enhance the rigidity of these molecules. In order to enhance the lipophilicity of 1 and therefore increase its permeability, analogs 4-9 with a pyrrolidine ring in the tail chain were designed to introduce more hydrocarbon groups into the lead molecule as well as to reduce rotatable bonds in the molecule. Different enantiomers of the pyrrolidine ring were also studied to investigate the effect of chirality on the activity and selectivity of these molecules. Furthermore, one fluorine atom has been incorporated at the C4 position on the pyrrolidine ring (8 and 9) to reduce the basicity of this cyclic amine and protect it from metabolism. In another direction, the lipophilicity of new analogs was enhanced by incorporating additional fluorine atoms into the middle fluorobenzene linker of 1. Various compounds (10-14) bearing two or three fluorine atoms at different relative positions in the middle linker have been designed and synthesized. A combination of the increased rigidity offered by an unsaturated C—C triple bond and the enhanced lipophilicity associated with multi-fluorobenzene linkers as found in compounds 15 and 16 was also investigated to gain insights into the combined effect on the cell membrane permeability of the new analogs. We then performed further structural modification by combining the optimal multi-fluorobenzene linker with the pyrrolidine tail chain which retains the most nNOS inhibition activity from 1, wherein compounds 17 and 18 have been obtained to maximize the possible lipophilicity. Finally, the pKa of the cyclic amino group, i.e., pyrrolidine ring, in the tail chain was modulated by using different heterocycles, including morpholine (19) and azetidine (21), as well as introducing an electron withdrawing group into the pyrrolidine ring (20). All new analogs have been tested for their nNOS inhibition and selectivity over eNOS and iNOS using NO-hemoglobin capture assay, while their cell membrane permeability was investigated using a parallel artificial membrane permeability for blood brain barrier (PAMPA-BBB) assay. Compounds with high potency, selectivity and permeability were further examined in Caco-2 bidirectional assay to evaluate their P-gp substrate liability.

Results and Discussion
Chemistry

The synthesis of compounds 2 and 3 with enhanced rigidity in the tail chain is shown in Scheme 1. Deprotonation of pyrrole-protected 2,4-dimethylpyridine 22 by n-BuLi followed by a reaction of the generated anion with electrophile 23 provided intermediate 24 with the 2-aminopyridine head and the middle linker coupled. Sonogashira coupling of 24 with either N-Boc-N-methyl-propargylamine (25a) or 3-dimethylamino-1-propyne (25b) afforded alkynes carrying Boc-protected secondary (26a) or tertiary (26b) amine. Boc-deprotection of 26a followed by pyrrole deprotection yielded target compound 2, whereas pyrrole deprotection of 26b generated compound 3.

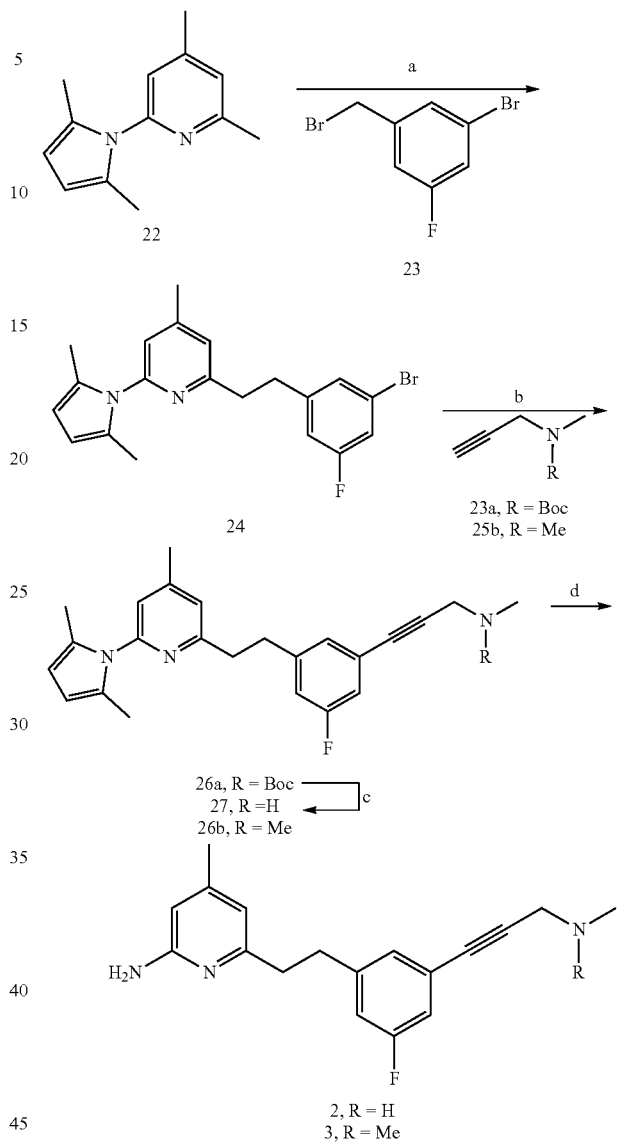

Scheme 1. Synthesis of 2 and 3

Reagents and conditions: (a) (i) n-BuLi 1.6M/THF, THF, -78° C.→-20° C., 15 min, (ii) 23, THF, -78° C.→-20° C., 20 min; (b) 25a or 25b, Pd(PPh₃)₄, CuI, TEA:DMF (9:1), Microwave, 120° C., 30 min; (c) 20% TFA, CH₂Cl₂, RT, 1 h; (d) NH₂OH·HCl, EtOH/H₂O (2:1), 100° C., 20 h.

The synthesis of pyrrolidine analogs 4-9 was carried through the preparation of pyrrolidinoalkynes 32a-c (Scheme 2). The pure enantiomers of these pyrrolidinoalkynes were directly synthesized from their corresponding aldehydes (30a-c) using Seyferth-Gilbert homologation. Aldehydes 30a-c were prepared from the oxidation of their corresponding alcohols, obtained from either commercial sources (29a and 29b) or by being synthesized (29c) from a carboxylic acid precursor (28). Scheme 3 shows the synthetic routes of 4-9 from 32a-c. Sonogashira coupling of intermediate 24 with different pyrrolidinoalkynes (32a-c), followed by a sequence of Boc-deprotection and hydrogenation, gave intermediates 34a-c. Pyrrole-deprotection of these intermediates provided secondary-amine analogs 4, 6, and 8. In a separated pathway, methylation of the secondary amino group using formaldehyde/NaBH₄, followed by a removal of the pyrrole protecting group generated tertiary-amine analogs 5, 7, and 9.

Scheme 2. Synthesis of pyrrolidinoalkynes
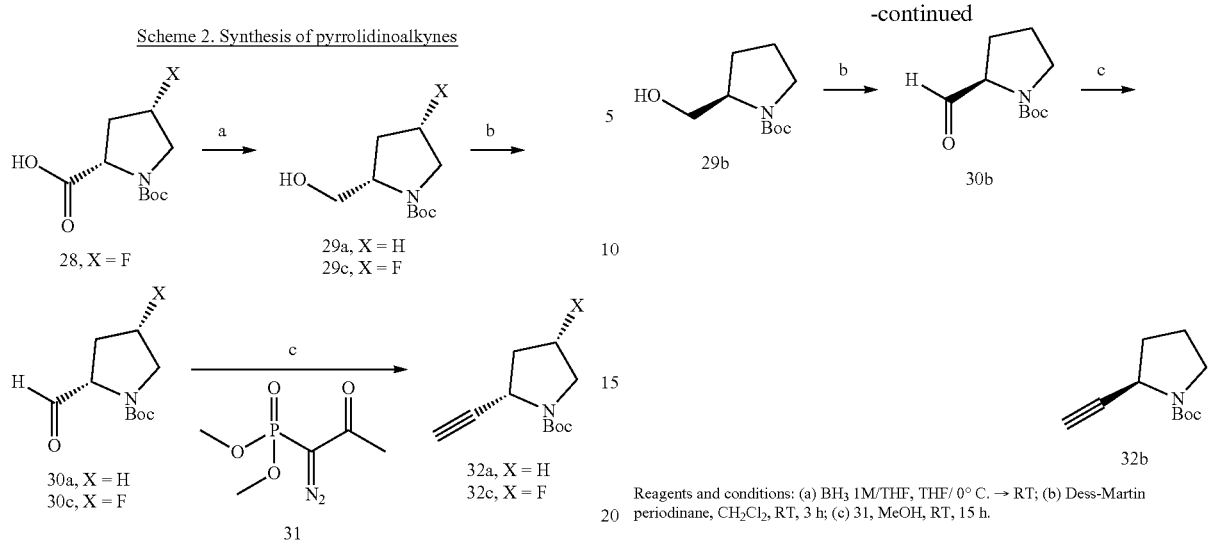
Reagents and conditions: (a) BH₃ 1M/THF, THF/ 0° C. → RT; (b) Dess-Martin periodinane, CH₂Cl₂, RT, 3 h; (c) 31, MeOH, RT, 15 h.
Scheme 3. Synthesis of pyrrolidine analogs 4-9
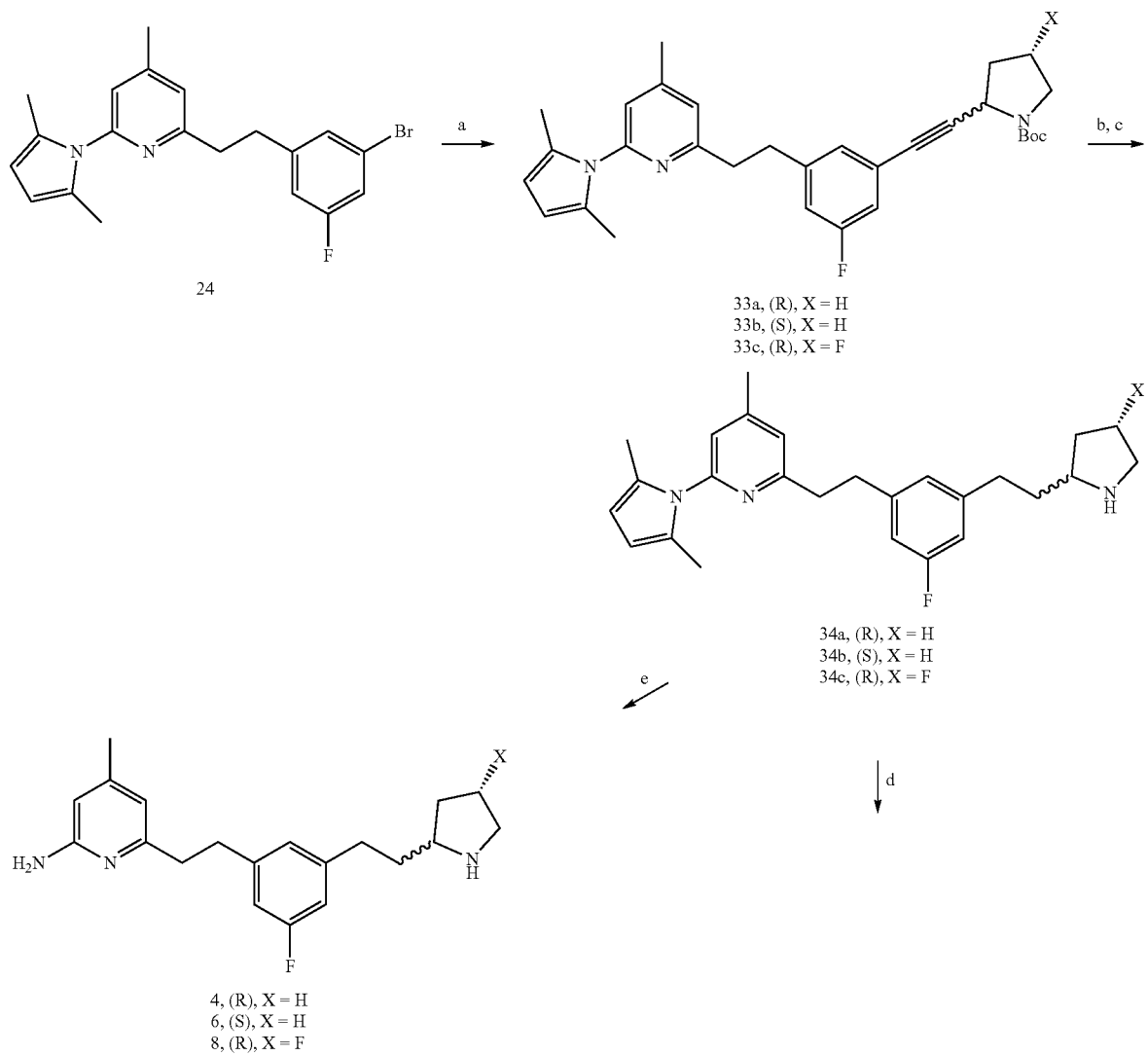

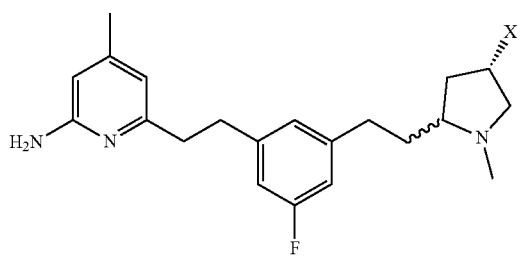

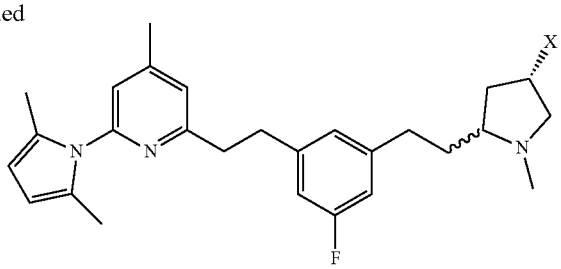

5, (R), X = H
7, (S), X = H
9, (R), X = F 35a, (R), X = H
35b, (S), X = H
35c, (R), X = F

Reagents and conditions: (a) 32a-c, Pd(PPh$_3$)$_4$, CuI, TEA:DMF (9:1), Microwave, 120° C., 30 min; (b) 20% TFA, CH$_2$Cl$_2$, RT, 1 h; (c) Pd/C, H$_2$, MeOH, RT, 20 h; (d) (i) HCHO 37% in H$_2$O, (ii) NaBH$_4$, MeOH; (e) NH$_2$OH•HCl, EtOH/H$_2$O (2:1), 100° C., 20 h.

The synthesis of analogs containing di- and tri-fluorobenzene linkers (10-14) was started with the preparation of linker components (36a-e) from commercially available sources (See the supporting information). Following a general synthetic route for nNOS inhibitors as shown in Scheme 1, the synthesized linkers (36a-e) were coupled with pyrrole-protected 2-aminopyridine head 22 through carbon-carbon bond formation using n-BuLi. The generated intermediates (37a-e) then underwent Sonogashira coupling with alkyne 25b to keep the tail chain the same as that of lead compound 1. Alkyne reduction of intermediates 38a-e followed by a pyrrole deprotection yielded the desired product 10-14 (Scheme 4).

Scheme 4. Synthesis of di- and trifluorobenzene analogs 10-14

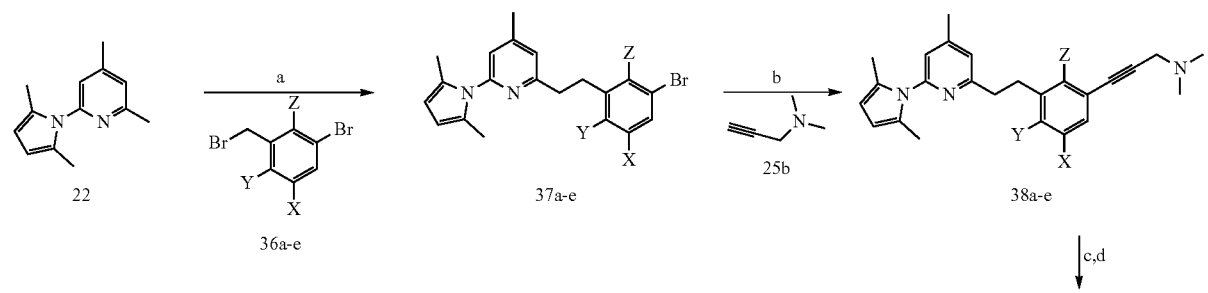

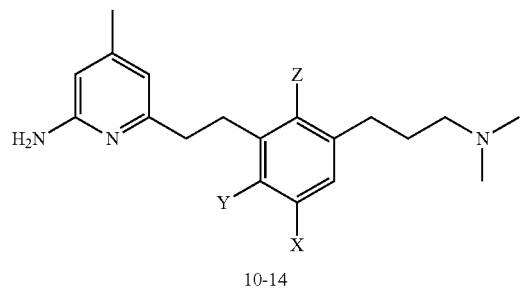

10-14

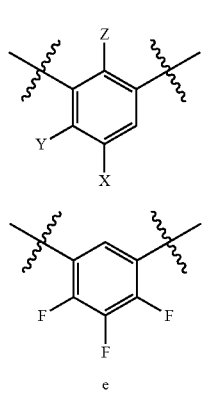

Reagents and conditions: (a) (i) n-BuLi 1.6 M/THF, THF, -78° C.→ -20° C., 15 min, (ii) 36a-e, THF, -78° C.→ -20° C., 20 min; (b) 25b, Pd(PPh₃)₄, CuI, TEA:DMF (9:1), Microwave, 120° C., 30 min; (c) Pd/C, H₂, MeOH, RT, 20 h; (d) NH₂OH·HCl, EtOH/H₂O (2:1), 100° C., 20 h.

In order to obtain the highest possible improvement in cell membrane permeability, a new set of compounds with both enhanced lipophilicity and increased rigidity were synthesized. New analogs were designed to have a difluorobenzene middle linker and a tail chain containing either a pyrrolidine ring or an alkyne amino group in the tail chain to increase their lipophilicity or reduce the number of rotatable bonds, respectively. The synthesis of these analogs (15-18) is shown in Scheme 5. Sonogashira coupling reactions of a previously synthesized 37a with different alkynes (25a-b, 32a-b) yielded intermediates 39 and 41-43. A Boc-deprotection of 39 generated the intermediate 40, which underwent a pyrrole-deprotection along with 41 to yield the two desired compounds (15 and 16) bearing the alkyne amino group in the tail chain. On the other hand, 42 and 43 were undergone a sequence of reactions, including Boc-deprotection, hydrogenation with Pd/C, methylation with formaldehyde, and pyrrole deprotection, to give the target products (17 and 18) containing a pyrrolidine ring in their tail chain.

The synthesis of compounds 19-21 to modulate the pKa of the amino group in the tail chain were first involved the preparation of the corresponding alkyne-functionalized tail chains (44a-c), whose syntheses can be found in the Supporting Information. Sonogashira coupling again were used to attach these tail chains to intermediate 37a. The target compounds (19-21) were obtained by subsequent reactions including (i) Boc/Cbz deprotection, (ii) hydrogenation of alkyne, (iii) a methylation of secondary amine to tertiary amine by HCHO/NaBH₄, and (iv) a pyrrole deprotection. It is worth mentioning that these reactions worked efficiently for the synthesis of 19, while the removal of Cbz group in the synthesis of 20 and 21 required the use of Pd(OH)₂/C under H₂ gas. The use of Pd/C, H₂ to remove Cbz group did not yield the desired products even at a high pressure up to 110 psi hydrogen gas. Additionally, Sonogashira coupling of azetidine alkyne 44c required the use of a different Pd catalyst and base (i.e., Pd(PPh₃)₂Cl₂ and diethylamine, respectively) to obtain a reasonable yield and less inseparable byproducts (Scheme 6).

Scheme 5. Synthesis of analogs 15-18 with enhanced lipophilicity and rigidity

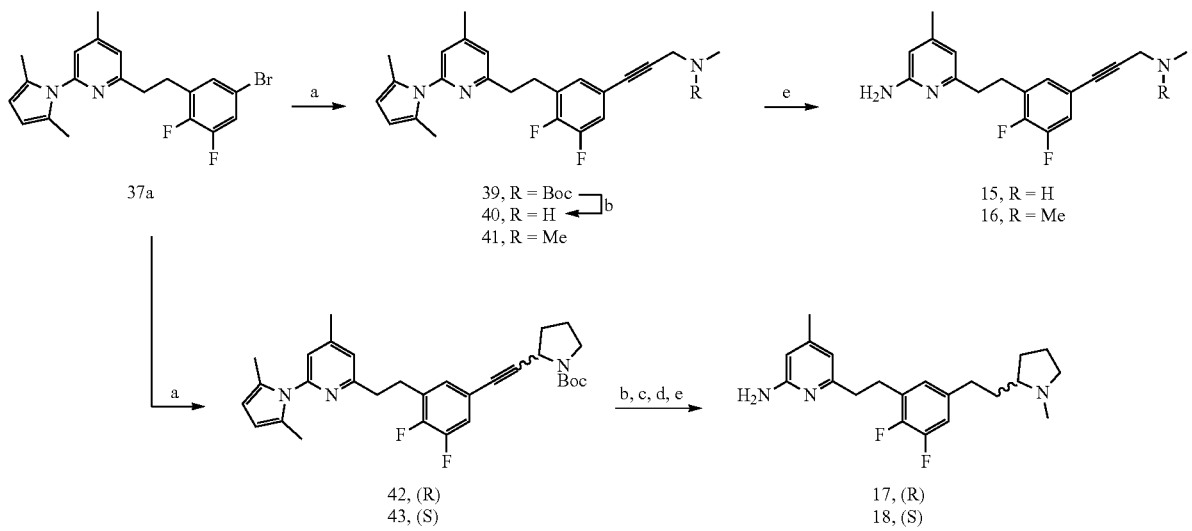

Reagents and conditions: (a) 25a-b or 32a-b, Pd(PPh₃)₄, CuI, TEA:DMF (9:1), Microwave, 120° C., 30 min; (b) 20% TFA, CH₂Cl₂, RT, 1 h; (c) Pd/C, H₂, MeOH, RT, 20 h; (d) (i) HCHO 37% in H₂O, (ii) NaBH₄, MeOH; (e) NH₂OH·H₂O (2:1), 100° C., 20 h.

Scheme 6. Synthesis of 19-21

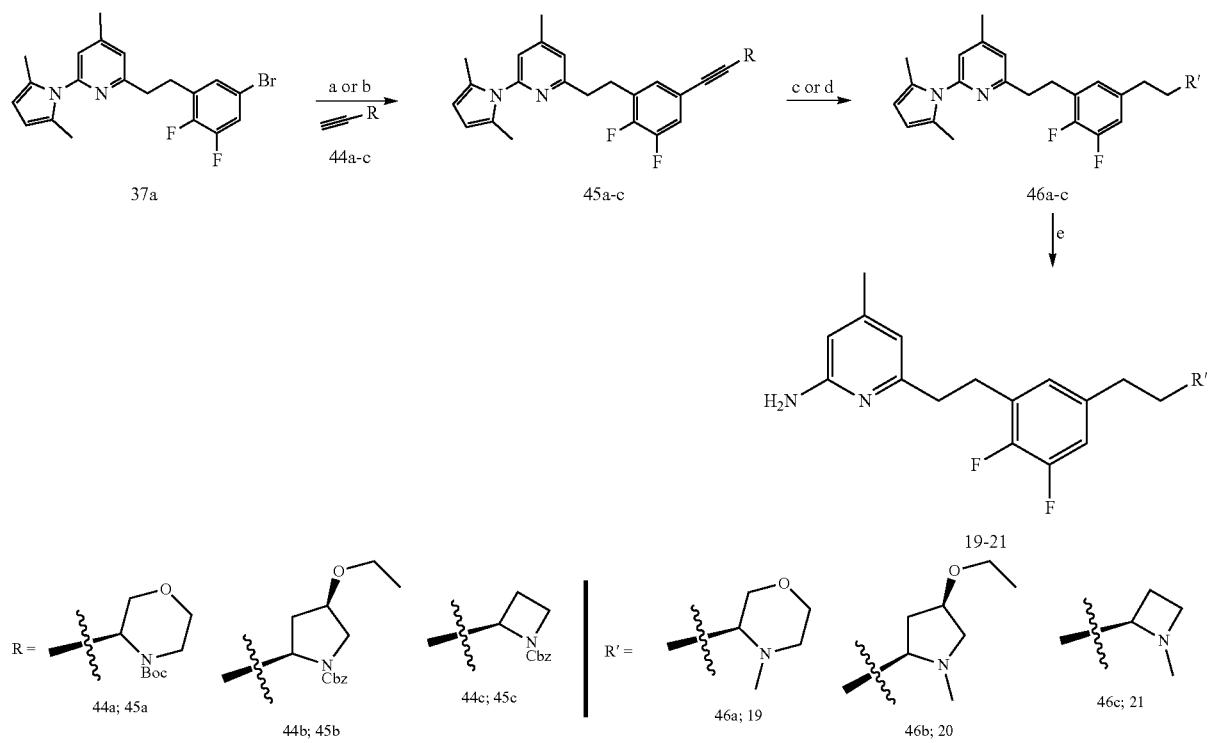

Reagents and conditions: (a) 44a or 44b, Pd(PPh₃)₄, CuI, TEA:DMF (9:1), Microwave, 120° C., 30 min; (b) 44c, Pd(PPh₃)₂Cl₂, CuI, PPh₃, DEA:DMF (1:1), Microwave, 120°C., 20 min; (c) 45a → 46a: (i) 20% TFA, CH₂Cl₂, RT, 1 h, (ii) Pd/C, H₂, MeOH, RT, 20 h, (iii) HCHO 37% in H₂O, NaBH₄, MeOH; (d) 45b-c → 46b-c: (i) Pd(OH)₂/C, H₂ (1 atm), MeOH, RT, 20 h, (ii) HCHO 37% in H₂O, NaBH₄, MeOH; (e) NH₂OH·H₂O (2:1), 100° C, 20 h.

Biological Activity

The nNOS inhibitory activity and selectivity of new analogs 2-21 were determined using the NO hemoglobin capture assay and the results are summarized in Table 1 along with those of compound 1 for comparison. On the basis of screening, these compounds were first tested against rat and human nNOS and murine iNOS to evaluate their potency and selectivity on account of the ease of expression and purification of these enzymes. Beside the selectivity of nNOS over iNOS (n/i), the inhibitory activity of those compounds toward rat and human nNOS was also compared (hn/rn ratio) since this ratio is a useful information for the translation from preclinical to clinical studies. The parallel artificial membrane permeability for blood brain barrier (PAMPA-BBB) assay was used to evaluate the effects of our structural modifications on the cell membrane permeability of 2-21, which helps to understand the structure-permeability relationship of these compounds.

TABLE 1

Rat and human nNOS potency, selectivity over murine iNOS, and effective permeability in PAMPA-BBB assay of 1-21

| Comp | $K_i$ (nM) rat nNOS | $K_i$ (nM) human nNOS | $K_i$ (nM) murine iNOS | Selectivity hnNOS/rnNOS | Selectivity rnNOS/miNOS | $P_e$ ($10^{-6}$ cm · s$^{-1}$) |
|---|---|---|---|---|---|---|
| 1 | 26 | 30 | 3857 | 1.2 | 149 | 14.80 ± 0.69 |
| 2 | 32 | 58 | 7616 | 1.8 | 238 | 15.52 ± 0.02 |
| 3 | 58 | 124 | 4890 | 2.1 | 143 | 18.76 ± 0.03 |
| 4 | 31 | 68 | 2183 | 2.2 | 70 | 5.18 ± 0.05 |
| 5 | 26 | 52 | 2910 | 2 | 86 | 13.30 ± 1.44 |
| 6 | 28 | 59 | 2704 | 2.1 | 96 | 5.52 ± 0.22 |
| 7 | 33 | 84 | 3386 | 2.5 | 103 | 13.61 ± 0.24 |
| 8 | 65 | 129 | 4542 | 1.98 | 70 | 12.34 ± 0.06 |
| 9 | 128 | 204 | 5011 | 1.6 | 39 | 18.90 ± 0.08 |
| 10 | 19 | 29 | 823 | 1.53 | 43 | 15.90 ± 0.48 |
| 11 | 60 | 36 | 2198 | 0.6 | 37 | 15.38 ± 0.50 |
| 12 | 79 | 157 | 1950 | 1.98 | 25 | 16.35 ± 0.44 |
| 13 | 47 | 58 | 3264 | 1.23 | 69 | 18.62 ± 0.20 |
| 14 | 45 | 46 | 2119 | 1.0 | 47 | 18.70 ± 0.20 |
| 15 | 27 | 43 | 3028 | 1.6 | 112 | 18.62 ± 0.48 |
| 16 | 81 | 84 | 4410 | 1.04 | 54 | 18.64 ± 0.31 |
| 17 | 27 | 37 | 2187 | 1.4 | 84 | 17.91 ± 0.60 |
| 18 | 13 | 21 | 1290 | 1.9 | 99 | 17.00 ± 1.00 |
| 19 | 62 | 89 | 3452 | 1.4 | 56 | 21.10 ± 1.12 |
| 20 | 55 | 87 | 4499 | 1.6 | 82 | 17.67 ± 1.80 |
| 21 | 26 | 23 | 2060 | 0.9 | 79 | 16.32 ± 0.35 |

$K_i$ values were calculated from the IC$_{50}$ values of a dose-response curve using the Cheng-Prusoff equation. 6 to 9 concentrations were tested and the IC$_{50}$ was calculated from an average of at least two duplicates. The standard errors are less than 10%.

The structural modification of 1 was first taken on the tail chain where the bismethylene group were replaced by an acetylene one to enhance the rigidity of the molecule. The NOS inhibition studies revealed that compounds 2 and 3 display a decrease in both rat and human nNOS potency, with more significant effect on human species where the hnNOS/rnNOS $K_i$ ratio is ca. 2. Compound 3 with a tertiary amino group in the tail chain exhibits lower potencies than those of the secondary amine analog (2), in which the potencies of 3 drop of more than 2-fold and 4-fold for rat and human nNOS, respectively, compared to those of 1, while the potencies of 2 are only slightly diminished. Despite the reduction in the potency, 3 has an excellent permeability with $P_e$ values of $18.8 \times 10^{-6}$ cm·s$^{-1}$, indicating that reduction in the flexibility of 1 potentially helps to enhance its cell membrane permeability.

To enhance the lipophilicity of 1 and therefore potentially increase its permeability, compounds 4-9 with a pyrrolidine ring at the tail chain were designed to introduce more hydrocarbon groups into the lead molecule. Studies on rat and human nNOS inhibition of 4-9 showed that all compounds exhibit excellent potency to rat nNOS ($K_i$=~30 nM) except for 8 ($K_i$=65 nM) and 9 ($K_i$=128 nM), analogs that carry a fluorine atom on the pyrrolidine ring. The reduction in rnNOS inhibitory activities of 8 and 9 is possibly a result of a hinderance or a decrease in the pKa of the tail amino group, which is also observed in our previous report.[24] Compounds 4-7 maintain moderate hnNOS potencies compared to 1, while 8 and 9 display a significant drop in their activity (4-fold and 7-fold less than 1, respectively). There is only a slight difference in the activity of the two enantiomeric pairs, in which 4 and 5 show similar $K_i$ values for both rnNOS and hnNOS compared to those of 6 and 7, respectively. The selectivity of these compounds over murine iNOS, however, is slightly enhanced when switching from (R)-isomers (4, 5) to (S)-isomers (6, 7). In PAMPA-BBB assay, compounds with a tertiary amino group in the tail exhibit a tendency to permeate the lipid membrane more than their corresponding secondary amine analogs (5, 7 and 9 versus 4, 6 and 8, respectively). Furthermore, the additional fluorine atom on the pyrrolidine ring helps to improve the permeability of nNOS inhibitors, e.g., 8 and 9 exhibit a higher $P_e$ value than 4 and 5, respectively. The presence of both the tertiary amino group and the additional fluorine atom resulted in an excellent permeability of $18.9 \times 10^{-6}$ cm·s$^{-1}$ for compound 9, which is significantly higher than that of 1 ($P_e$=$14.8 \times 10^{-6}$ cm·s$^{-1}$). However, despite of its high $P_e$ value, 9 expresses a dramatic decrease in nNOS potency and selectivity.

Another modification direction to enhance the cell membrane permeability of 1 was achieved through the incorporation of additional fluorine atoms onto the middle fluorobenzene linker of our nNOS inhibitors. Compounds (10-14) bearing di- and tri-fluorobenzene linkers, wherein fluorine atoms are arranged at different relative positions to each other, were designed and synthesized. The results of biological activity studies revealed that the relative positions between fluorine atoms on the middle benzene ring have a certain effect on the nNOS inhibitory activity and selectivity of the five resulting modified compounds. Particularly, analogs containing an ortho-(10) and a meta-(11) difluorobenzene linker exhibit higher potency against both rnNOS and hnNOS than those of the analogs containing the para-difluorobenzene linker (12). Compared with lead compound 1, analog 12 exhibits a loss of more than half the original potency, while 10 displays a slightly better potency toward both rnNOS and hnNOS. Compounds 13 and 14, which contain a trifluorobenzene middle linker, exhibit a moderate decrease in both rat and human nNOS potency compared to 1 and 10. The addition of fluorine atoms to the middle linker, however, reduces the rat nNOS/murine iNOS selectivity for both di- and tri-fluorobenzene analogs. On the other hand, PAMPA-BBB assay indicates that the incorporation of one additional fluorine in 10-12 helps to increase the $P_e$ value of these new analogs though slightly compared to that of 1. These difluorobenzene-containing analogs show similar effective permeability of ca. $16 \times 10^{-6}$ cm·s$^{-1}$, regardless the different positional arrangements between the two fluorine atoms. Further incorporation of more fluorine into the middle linker, as found in trifluorobenzene-containing analogs 13 and 14, resulted in a significant improvement in cell membrane permeability. Notably, the $P_e$ value of 13 and 14 is approximately the same as that of 9, an analog with a fluoropyrrolidine group at the tail chain. These permeability studies by PAMPA-BBB assay, therefore, support the appropriate direction of our modification by incorporating additional fluorine atoms into the middle linker to enhance the permeability while retaining a sufficient nNOS inhibition and isoform selectivity of modified compounds.

The middle linker associated with the ortho-difluorobenzene ring in 10 was then taken to construct new analogs owing to its excellent nNOS inhibition and improvement in permeability shown in PAMPA-BBB assay. The new analogs were designed with an alkyne amino group (15, 16) and a pyrrolidine ring (17, 18) incorporated to the tail chain to reduce the number of rotatable bonds or further increase their lipophilicity, respectively. These two modification directions are expected to help enhance the permeability of the resulting analogs. Our biological studies on nNOS inhibition of these new compounds reveals that the incorporation of the alkyne group causes a drop in the nNOS potency of 15 and 16, in which compound 16 with a tertiary amino group in its tail chain inhibits more losses in potency than analog 15 with a secondary amine tail chain. Interestingly, 15 enables to restore the selectivity toward rnNOS over murine iNOS, which was previously diminished by the introduction of the difluorobenzene linker. It is also worth noting that a similar trend was also observed with compounds carrying an alkyne tail chain and a fluorobenzene middle linker (2, 3), in which the secondary-amine analog (2) exhibits better performance in both nNOS inhibition and selectivity than the tertiary-amine analog (3). In PAMPA-BBB assay, both 15 and 16 show an enhancement in their permeability with $P_e$ values ca. $18 \times 10^{-6}$ cm·s$^{-1}$. Interestingly, there is surprisingly negligible difference in the cell membrane permeability between the two analogs 15 and 16 regardless the fact that 15 carries one extra hydrogen bond donor, which often plays an important role in cell membrane permeability of CNS drugs, compared to 16. This observation suggests the significant effect of structural rigidity on the permeability of an analog. However, on account of the diminishments in nNOS potency and isoform activity, modification of nNOS inhibitors using this rigid alkyne-containing tail chain has not been favored for further studies.

Analogs 17 and 18 were obtained through a combined modification of using both a difluorobenzene middle linker and a pyrrolidine ring in the tail chain. The hemoglobin NO capture assays revealed that both compounds exhibit excellent potency in nNOS inhibition, in which the (S)-isomer 18 displays higher potency and selectivity than its counterpart (R)-isomer 17. Promisingly, analog 18 shows an enhancement in rat and human nNOS inhibition compared the lead compound 1, where inhibitory activities of 18 toward rNOS and hNOS are respectively around 2-fold and 1.5-fold better than those of 1. Cell membrane permeability studies by PAMPA-BBB assay of 17 and 18 indicates that both compounds exhibit enhanced permeability with $P_e$ values close to $18.0 \times 10^{-6}$ cm·s$^{-1}$. These results support our proposed direction to improve cell membrane permeability of nNOS inhibitors by increasing the lipophilicity and/or rigidity of the lead molecule.

We then carried out further modification based on the structural scaffold of 18 on account of its excellence on nNOS activity, selectivity and cell membrane permeability. Various heterocycles including morpholine, (4-ethoxy)pyrrolidine, and azetidine as found in compounds 19, 20, and 21, respectively, were utilized to modulate the basicity of the tertiary amino group of the pyrrolidine ring, which could potentially enhance its permeability and protect it from metabolism.[26] Biological studies revealed that the replacement of the pyrrolidine ring in 18 by a morpholine ring in 19 resulted in a loss of more than half inhibitory activity of this compound against both rat and human nNOS. Similarly, the introduction of an ethoxy group at C4 of the pyrrolidine ring caused a decrease in the nNOS potency of 20. In contrast, the use of an azetidine ring in place of the pyrrolidine ring led to a high nNOS inhibition of the resulting compound 21, which has comparable rnNOS and hnNOS $K_i$ values as well as isoform selectivity to those of 18. Regarding cell membrane permeability, despite the loss in nNOS inhibitory activity, 19 exhibits a significant improvement in permeability with $P_e$ value of $21.1 \times 10^{-6}$ cm·s$^{-1}$, which is the highest permeability value we have obtained for our nNOS inhibitors based on the 2-aminopyridine scaffold and is comparable to the positive control compound, verapamil ($P_e = 20.2 \times 10^{-6}$ cm·s$^{-1}$). On the other hand, the PAMPA-BBB studies on the two analogs 20 and 21 reveal that our structural modification by replacing the pyrrolidine ring in 18 with (4-ethoxy)pyrrolidine (20) and azetidine (21) retains the permeability of these analogs, indicating by little changes in the effective permeability of 20 ($P_e = 17.7 \times 10^{-6}$ cm·s$^{-1}$) and 21 ($P_e = 16.3 \times 10^{-6}$ cm·s$^{-1}$), compared to that of 18.

Besides our efforts to enhance the cell membrane permeability of nNOS inhibitors, we have also aimed to obtain the isoform selectivity of our nNOS inhibitors using all human NOS isoforms to provide a precise comparison in the selectivity. While bovine eNOS and murine iNOS were previously used for the isoform selectivity, our recent success in the preparation of hiNOS enzyme allows us to perform this selectivity study on all human NOS for the first time. Based on the above biological activity studies, six compounds (10, 14, 15, 17, 18 and 21) with excellent human nNOS inhibitory activity, as well as their structural diversity, were selected for the selectivity study over human eNOS (heNOS) and human iNOS (hiNOS), and the results of isoform selectivity on inhibiting human NOS for these compounds are summarized in Table 2. The data reveal that most the selected compounds display excellent selectivity for hnNOS over heNOS with a hnNOS/heNOS ratio in the 900-1200 range with the exception of analog 15, which has a 394 hnNOS/heNOS selective ratio. For human iNOS, the use of difluorobenzene linker tends to result in a decrease in selectivity of the selected analogs compared to lead compound 1, which is consistent with the observation for rnNOS selectivity over murine iNOS (Table 1). Unlike other analogs, 18 and 21 display some retainability for the hnNOS/hiNOS selectivity with a selective ratio of 106 and 77, respectively. Consequently, these two compounds have been selected for other studies, including P-gp substrate liability, to evaluate their potential of becoming a CNS drug.

TABLE 2

Potency and selectivity of selective compounds on human NOSes

| Compound | $K_i$ (nM) | | | Selectivity | |
| --- | --- | --- | --- | --- | --- |
| | human nNOS | human eNOS | human iNOS | hnNOS/ heNOS | hnNOS/ hiNOS |
| 1 | 30 | 83976 | 3501 | 2756 | 117 |
| 10 | 29 | 35028 | 1312 | 1208 | 45 |
| 14 | 46 | 50280 | 2509 | 1093 | 54 |
| 15 | 43 | 16960 | 3059 | 394 | 71 |
| 17 | 37 | 35758 | 1635 | 966 | 44 |
| 18 | 21 | 25548 | 2222 | 1216 | 106 |
| 21 | 23 | 21980 | 1780 | 956 | 77 |

P-Gp Substrate Liability

P-glycoprotein (P-gp) is an efflux transporter that is highly expressed at the BBB to quickly wash any harmful molecules, as well as potential drugs, out the brain.[5, 27] Evaluation the potential of a compound as a P-gp substrate, therefore, is one of crucial steps in CNS drug development. The P-gp substrate liability of a compound can be evaluated through an efflux ratio (ER) obtained from a Caco-2 bidirectional assay,[28] which measures the ability of compounds to cross a monolayer of colon cells with expressed P-gp from two directions, either from apical to basal (A→B) or from basal to apical (B→A) wells. An ER ratio is then determined by a ratio of the apparent permeability ($P_{app}$) of B→A over A→B. If compounds with an ER larger than 3 are often considered as a substrate of P-gp with limited penetration into the brain.[3]

In our previous study, the main detriment of the lead compound 1 for further studies in CNS drug development is the undesired high efflux ratio (ER=5.9) of this compound, as revealed in Caco-2 bidirectional assay. Therefore, reducing the ER of 1 is a crucial step for our 2-aminopyridine nNOS inhibitors before these compounds can be advanced to a next stage in drug development, i.e., animal studies. On account of the excellent potency, retained isoform selectivity, and high cell membrane permeability by PAMPA-BBB assay, analogs 18 and 21 have selected for evaluating their ER in Caco-2 bidirectional assay. The results summarized in Table 3 reveal that the two compounds express exceedingly promising efflux ratios. Analog 18 displays an ER of 2.1, which is much lower than that of lead compound 1 (ER=5.9) and more importantly within the regime of the efflux ratios (less than 2.5) required for a molecule to be likely a CNS(+) drug. More interestingly, compound 21 shows an ER of as low as 0.8, an indication of a very low liability to become a P-gp substrate. These results suggest a great potential of the two analogs to cross the BBB and penetrate the brain. It is worth noting that, for an unknown reason, 18 exhibits a low permeability in Caco-2 assay with $P_{app}$ (A→B) of only $1.1 \times 10^{-6}$ cm·s$^{-1}$. Nevertheless, our most promising compound, analog 21, exhibits not only excellent nNOS inhibition and selectivity, but also great potential in its ability to cross the BBB to penetrate the brain as indicated by both PAMPA-BBB and Caco-2 assays. The $P_{app}$ (A→B) value of $17.0 \times 10^{-6}$ cm·s$^{-1}$ in Caco-2 assay of 21 is also shown an excellent consistency with the effective permeability ($P_e = 16.3 \times 10^{-6}$ cm·s$^{-1}$) obtained from the PAMPA-BBB results.

TABLE 3

Caco-2 apparent permeability and efflux ratio (ER) of selected nNOS inhibitors with control compounds

| Compound | Apparent permeability ($P_{app}$, $10^{-6}$ cm·s$^{-1}$)[a] | | Efflux ratio |
|---|---|---|---|
| | mean A→B | mean B→A | |
| 1 | 9.2 ± 0.3 | 54.2 ± 17.6 | 5.9 |
| 18 | 1.1 ± 0.1 | 2.3 ± 0.2 | 2.1 |
| 21 | 17.05 ± 0.08 | 13.71 ± 0.07 | 0.8 |
| Metoprolol[b] | 37.18 | 20.39 | 0.55 |
| Atenolol[c] | 0.39 | 0.58 | 1.47 |
| Erythromycin[d] | <0.17 | 13.39 | >78.76 |

[a]Apparent permeability value.
[b]High permeability control.
[c]Low permeability control.
[d]High efflux control.

CONCLUSION

In summary, we report our optimization of nNOS inhibitors bearing a 2-aminopyridine scaffold with emphasis on improving the cell membrane permeability of these inhibitors to be able to cross the blood brain barrier, while retaining their excellent inhibition activity and high isoform selectivity. A new series of potent and selective human nNOS inhibitors have been designed and synthesized by employing various medicinal chemistry approaches involving enhancing the lipophilicity, increasing molecular rigidity, and modulating the pKa of the basic amino tail group of the lead molecule 1. NO hemoglobin capture and PAMPA-BBB assays have been used to understand the effects of structural modification on nNOS inhibition potency and isoform selectivity, and cell membrane permeability of the new analogs. We found that the introduction of one additional fluorine atom into the fluorobenzene middle linker and the use of an azetidine ring in the tail chain have led to the discovery of compound 21, which not only displays an excellent inhibition for human nNOS ($K_i$=23 nM) and high selectivity over human eNOS (hn/he=956) and human iNOS (hn/hi=77), but also exhibits a great potential of brain penetration. Caco-2 bidirectional assay reveals that 21 has an efflux of only 0.8, which is significantly lower than the lead compound 1 (ER=5.9) and the required ER<2.5 for CNS(+) drugs. The Caco-2 bidirectional assay also revealed that 21 has high cell membrane permeability with the $P_{app}$ value of 17.0×10$^{-6}$ cm·s$^{-1}$, which is in good agreement with the effective permeability ($P_e$=16.3×10$^{-6}$ cm·s$^{-1}$) determined by PAMPA-BBB assay. Our results herein provide the basis for further exploration of the 2-aminopyridine nNOS inhibitors in CNS drug development and additional insights into the strategies to overcome the BBB using medicinal chemistry approaches.

REFERENCES FOR EXAMPLE 1

1. Gribkoff, V. K.; Kaczmarek, L. K. The need for new approaches in CNS drug discovery: Why drugs have failed, and what can be done to improve outcomes. *Neuropharmacology* 2017, 120, 11-19.
2. Nutt, D. J.; Attridge, J. CNS drug development in Europe Past progress and future challenges. *Neurobiology of Disease* 2014, 61, 6-20.
3. Di, L.; Rong, H.; Feng, B. Demystifying Brain Penetration in Central Nervous System Drug Discovery. *Journal of Medicinal Chemistry* 2013, 56, 2-12.
4. Banks, W. A. From blood-brain barrier to blood-brain interface: new opportunities for CNS drug delivery. *Nature Reviews Drug Discovery* 2016, 15, 275.
5. Loscher, W.; Potschka, H. Drug resistance in brain diseases and the role of drug efflux transporters. *Nature Reviews Neuroscience* 2005, 6, 591.
6. Di, L. K., E. H. Drug-like Properties: Concepts, Structure Design, and Methods from ADME to Toxicity Optimization. *Elsevier: Amsterdam* 2016, Second Edition, 329.
7. Rankovic, Z. CNS Drug Design: Balancing Physicochemical Properties for Optimal Brain Exposure. *Journal of Medicinal Chemistry* 2015, 58, 2584-2608.
8. Maccallini, C.; Amoroso, R. Targeting neuronal nitric oxide synthase as a valuable strategy for the therapy of neurological disorders. *Neural Regeneration Research* 2016, 11, 1731-1734.
9. Drechsel, D. A.; Estevez, A. G.; Barbeito, L.; Beckman, J. S. Nitric oxide-mediated oxidative damage and the progressive demise of motor neurons in ALS. *Neurotoxicity research* 2012, 22, 251-264.
10. de la Torre, J. C.; Stefano, G. B. Evidence that Alzheimer's disease is a microvascular disorder: the role of constitutive nitric oxide. *Brain Research Reviews* 2000, 34, 119-136.
11. J Garthwaite, a.; Boulton, C. L. Nitric Oxide Signaling in the Central Nervous System. *Annual Review of Physiology* 1995, 57, 683-706.
12. Uehara, T.; Nakamura, T.; Yao, D.; Shi, Z.-Q.; Gu, Z.; Ma, Y.; Masliah, E.; Nomura, Y.; Lipton, S. A. S-Nitrosylated protein-disulphide isomerase links protein misfolding to neurodegeneration. *Nature* 2006, 441, 513-517.
13. Torreilles, F.; Salman-Tabcheh, S. d.; Guerin, M.-C.; Torreilles, J. Neurodegenerative disorders: the role of peroxynitrite. *Brain Research Reviews* 1999, 30, 153-163.
14. Bolanos, J. P.; Almeida, A.; Stewart, V.; Peuchen, S.; Land, J. M.; Clark, J. B.; Heales, S. J. R. Nitric oxide-mediated mitochondrial damage in the brain: Mechanisms and implications for neurodegenerative diseases. *Journal of Neurochemistry* 1997, 68, 2227-2240.
15. Mukherjee, P.; Cinelli, M. A.; Kang, S.; Silverman, R. B. Development of nitric oxide synthase inhibitors for neurodegeneration and neuropathic pain. *Chemical Society Reviews* 2014, 43, 6814-6838.
16. Silverman, R. B. Design of Selective Neuronal Nitric Oxide Synthase Inhibitors for the Prevention and Treatment of Neurodegenerative Diseases. *Accounts of Chemical Research* 2009, 42, 439-451.
17. ALDERTON, W. K.; COOPER, C. E.; KNOWLES, R. G. Nitric oxide synthases: structure, function and inhibition. *Biochemical Journal* 2001, 357, 593-615.
18. Moore, P. K.; Handy, R. L. C. Selective inhibitors of neuronal nitric oxide synthase—is no NOS really good NOS for the nervous system? *Trends in Pharmacological Sciences* 1997, 18, 204-211.
19. Li, H.; Wang, H.-Y.; Kang, S.; Silverman, R. B.; Poulos, T. L. Electrostatic Control of Isoform Selective Inhibitor Binding in Nitric Oxide Synthase. *Biochemistry* 2016, 55, 3702-3707.
20. Barbanti, P.; Egeo, G.; Aurilia, C.; Fofi, L.; Della-Morte, D. Drugs targeting nitric oxide synthase for migraine treatment. *Expert Opinion on Investigational Drugs* 2014, 23, 1141-1148.
21. Ji, H.; Stanton, B. Z.; Igarashi, J.; Li, H.; Martisek, P.; Roman, L. J.; Poulos, T. L.; Silverman, R. B. Minimal Pharmacophoric Elements and Fragment Hopping, an Approach Directed at Molecular Diversity and Isozyme Selectivity. Design of Selective Neuronal Nitric Oxide 22. Kang, S.; Li, H.; Tang, W.; Martisek, P.; Roman, L. J.; Poulos, T. L.; Silverman, R. B. 2-Aminopyridines with a Truncated Side Chain To Improve Human Neuronal Nitric Oxide Synthase Inhibitory Potency and Selectivity. *Journal of Medicinal Chemistry* 2015, 58, 5548-5560.
23. Wang, H.-Y.; Qin, Y.; Li, H.; Roman, L. J.; Martisek, P.; Poulos, T. L.; Silverman, R. B. Potent and Selective Human Neuronal Nitric Oxide Synthase Inhibition by Optimization of the 2-Aminopyridine-Based Scaffold with a Pyridine Linker. *Journal of Medicinal Chemistry* 2016, 59, 4913-4925.
24. Do, H. T.; Wang, H.-Y.; Li, H.; Chreifi, G.; Poulos, T. L.; Silverman, R. B. Improvement of Cell Permeability of Human Neuronal Nitric Oxide Synthase Inhibitors Using Potent and Selective 2-Aminopyridine-Based Scaffolds with a Fluorobenzene Linker. *Journal of Medicinal Chemistry* 2017, 60, 9360-9375.
25. Wager, T. T.; Hou, X.; Verhoest, P. R.; Villalobos, A. Moving beyond Rules: The Development of a Central Nervous System Multiparameter Optimization (CNS MPO) Approach To Enable Alignment of Druglike Properties. *ACS Chemical Neuroscience* 2010, 1, 435-449.
26. St. Jean, D. J.; Fotsch, C. Mitigating Heterocycle Metabolism in Drug Discovery. *Journal of Medicinal Chemistry* 2012, 55, 6002-6020.
27. Feng, B.; Mills, J. B.; Davidson, R. E.; Mireles, R. J.; Janiszewski, J. S.; Troutman, M. D.; de Morais, S. M. In Vitro P-glycoprotein Assays to Predict the in Vivo Interactions of P-glycoprotein with Drugs in the Central Nervous System. *Drug Metabolism and Disposition* 2008, 36, 268-275.
28. Patil, A. G.; D'Souza, R.; Dixit, N.; Damre, A. Validation of quinidine as a probe substrate for the in vitro P-gp inhibition assay in Caco-2 cell monolayer. *European Journal of Drug Metabolism and Pharmacokinetics* 2011, 36, 115.
29. Hevel, J. M.; Marletta, M. A. [25] Nitric-oxide synthase assays. *Methods in Enzymology* 1994, 233, 250-258.
30. Roman, L. J.; Sheta, E. A.; Martasek, P.; Gross, S. S.; Liu, Q.; Masters, B. S. High-level expression of functional rat neuronal nitric oxide synthase in *Escherichia coli*. *Proceedings of the National Academy of Sciences* 1995, 92, 8428-8432.
31. Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. *Acta Crystallographica Section D: Biological Crystallography* 2014, 70, 2667-2674.
32. Hevel, J. M.; White, K. A.; Marletta, M. A. Purification of the inducible murine macrophage nitric oxide synthase. Identification as a flavoprotein. *Journal of Biological Chemistry* 1991, 266, 22789-91.
33. Li, H.; Raman, C. S.; Glaser, C. B.; Blasko, E.; Young, T. A.; Parkinson, J. F.; Whitlow, M.; Poulos, T. L. Crystal Structures of Zinc-free and -bound Heme Domain of Human Inducible Nitric-oxide Synthase: IMPLICATIONS FOR DIMER STABILITY AND COMPARISON WITH ENDOTHELIAL NITRIC-OXIDE SYNTHASE. *Journal of Biological Chemistry* 1999, 274, 21276-21284.
34. Fischmann, T. O.; Hruza, A.; Niu, X. D.; Fossetta, J. D.; Lunn, C. A.; Dolphin, E.; Prongay, A. J.; Reichert, P.; Lundell, D. J.; Narula, S. K.; Weber, P. C. Structural characterization of nitric oxide synthase isoforms reveals striking active-site conservation. *Nature Structural Biology* 1999, 6, 233.
35. Yung-Chi, C.; Prusoff, W. H. Relationship between the inhibition constant (KI) and the concentration of inhibitor which causes 50 percent inhibition (I50) of an enzymatic reaction. *Biochemical Pharmacology* 1973, 22, 3099-3108.
36. Leber, A.; Hemmens, B.; Klosch, B.; Goessler, W.; Raber, G.; Mayer, B.; Schmidt, K. Characterization of Recombinant Human Endothelial Nitric-oxide Synthase Purified from the Yeast *Pichia pastoris*. *Journal of Biological Chemistry* 1999, 274, 37658-37664.
37. Fossetta, J. D.; Niu, X. D.; Lunn, C. A.; Zavodny, P. J.; Narula, S. K.; Lundell, D. Expression of human inducible nitric oxide synthase in *Escherichia coli*. *FEBS Letters* 1996, 379, 135-138.
38. Müller, J.; Essö, K.; Dargó, G.; Könczöl, Á.; Balogh, G. T. Tuning the predictive capacity of the PAMPA-BBB model. *European Journal of Pharmaceutical Sciences* 2015, 79, 53-60.
39. Cinelli, M. A.; Li, H.; Chreifi, G.; Poulos, T. L.; Silverman, R. B. Nitrile in the Hole: Discovery of a Small Auxiliary Pocket in Neuronal Nitric Oxide Synthase Leading to the Development of Potent and Selective 2-Aminoquinoline Inhibitors. *Journal of Medicinal Chemistry* 2017, 60, 3958-3978.
40. Cinelli, M. A.; Li, H.; Pensa, A. V.; Kang, S.; Roman, L. J.; Martisek, P.; Poulos, T. L.; Silverman, R. B. Phenyl Ether- and Aniline-Containing 2-Aminoquinolines as Potent and Selective Inhibitors of Neuronal Nitric Oxide Synthase. *Journal of Medicinal Chemistry* 2015, 58, 8694-8712.
41. McPhillips, T. M.; McPhillips, S. E.; Chiu, H.-J.; Cohen, A. E.; Deacon, A. M.; Ellis, P. J.; Garman, E.; Gonzalez, A.; Sauter, N. K.; Phizackerley, R. P.; Soltis, S. M.; Kuhn, P. Blu-Ice and the Distributed Control System: software for data acquisition and instrument control at macromolecular crystallography beamlines. *Journal of Synchrotron Radiation* 2002, 9, 401-406.
42. Battye, T. G. G.; Kontogiannis, L.; Johnson, O.; Powell, H. R.; Leslie, A. G. W. iMOSFLM: a new graphical interface for diffraction-image processing with MOSFLM. *Acta Crystallographica Section D: Biological Crystallography* 2011, 67, 271-281.
43. Kabsch, W. XDS. *Acta Crystallographica Section D: Biological Crystallography* 2010, 66, 125-132.
44. Evans, P. Scaling and assessment of data quality. *Acta Crystallographica Section D* 2006, 62, 72-82.
45. Murshudov, G. N.; Vagin, A. A.; Dodson, E. J. Refinement of Macromolecular Structures by the Maximum-Likelihood Method. *Acta Crystallographica Section D* 1997, 53, 240-255.
46. Emsley, P.; Cowtan, K. Coot: model-building tools for molecular graphics. *Acta Crystallographica Section D* 2004, 60, 2126-2132.
47. Adams, P. D.; Afonine, P. V.; Bunkoczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. PHENIX: a comprehensive Python-based system for macromolecular structure solution. *Acta Crystallographica Section D* 2010, 66, 213-221.
48. Li, H.; Jamal, J.; Plaza, C.; Pineda, S. H.; Chreifi, G.; Jing, Q.; Cinelli, M. A.; Silverman, R. B.; Poulos, T. L. Structures of human constitutive nitric oxide synthases. *Acta Crystallographica Section D* 2014, 70, 2667-2674.

49. McCoy, A. J.; Grosse-Kunstleve, R. W.; Adams, P. D.; Winn, M. D.; Storoni, L. C.; Read, R. J. Phaser crystallographic software. *Journal of Applied Crystallography* 2007, 40, 658-674.
50. Winn, M. D.; Isupov, M. N.; Murshudov, G. N. Use of TLS parameters to model anisotropic displacements in macromolecular refinement. *Acta Crystallographica Section D* 2001, 57, 122-133.
51. Liebschner, D.; Afonine, P. V.; Moriarty, N. W.; Poon, B. K.; Sobolev, O. V.; Terwilliger, T. C.; Adams, P. D. Polder maps: improving OMIT maps by excluding bulk solvent. *Acta Crystallographica. Section D, Structural Biology* 2017, 73, 148-157.

Example 2

The following example provides supporting information for the information disclosed in Example 1 as follows.

Reference is made to the supporting information for the manuscript: Do et al., "Optimization of Blood-Brain Barrier Permeability with Potent and Selective Human Neuronal Nitric Oxide Synthase Inhibitors Having a 2-Aminopyridine Scaffold," J. Med. Chem. 2019, 62, 5, 2690-2707, published Feb. 25, 2019, the content of which is incorporated herein by reference in its entirety.

General Procedures. All reagents unless specified were obtained from Sigma-Aldrich, Combi-blocks and Oakwood Chemical. Anhydrous solvents (THF, $CH_2Cl_2$, MeCN, and DMF) were purified before use by passing through a column composed of activated alumina and a supported copper redox catalyst. Sonogashira coupling was carried out in the Biotage Initiator microwave using Biotage microwave vials (0.5-2 mL, 2-5 mL and 10-20 mL). Thin layer chromatography (TLC) was performed on silica gel 60 F254 pre-coated plates (0.25 mm) from Silicycle, and components were visualized by ultraviolet light (254 nm) and/or $KMnO_4$ or ninhydrin stain. Flash column chromatography was performed on an Agilent 971-FP automated flash purification system with a Varian column station and various Silicycle cartridges (4-80 g, 40-63 μm, 60 Å). $^1H$ and $^{13}C$ NMR spectra were recorded on a Bruker Avance-III NMR spectrometer at 500 MHz and 126 MHz, respectively, in $CDCl_3$ or $CD_3OD$. Chemical shifts were reported in ppm, multiplicities are indicated by s=singlet, d=doublet, t=triplet, q=quartet, sep=septet, dd=doublet of doublet, dt=doublet of triplet, m=multiplet, br=broad resonance. Coupling constants 'J' were reported in Hz. High resolution mass spectral data were obtained on an Agilent 6210 LC-TOF spectrometer in the positive ion mode using electrospray ionization with an Agilent G1312A HPLC pump and an Agilent G1367B autoinjector at the Integrated Molecular Structure Education and Research Center (IMSERC), Northwestern University. The purity of compounds was tested by using a reserved-phase analytical Agilent Infinity 1260 HPLC with an Agilent Poroshell 120 EC-C18 column, detecting with UV absorbance at 254 nm. All compounds undergoing biological tested had >95% purity.

General Procedure A: Pyrrole deprotection: In a microwave vial, starting materials 26b or 41 (1 equiv.) and $NH_2OH·HCl$ (3-4 equiv.) were added. They are diluted with EtOH/water (2:1) to form a 0.16 M solution. The microwave vial was capped, and the reaction mixture was run at 100° C. for 20 h. The cap was removed, and the reaction mixture was concentrated under reduced pressure. The crude product mixture was purified by reversed flash chromatography to give final products 3 or 16.

General Procedure B: Boc and pyrrole deprotection: Starting material 26a or 39 (1 equiv.) was dissolved in $CH_2Cl_2$ (0.1 M), followed by an addition of TFA (1.1 equiv.) at 0° C., and the reaction was run at RT After stirring at RT for 1 hour, the crude product was concentrated under reduced pressure, diluted back with $CH_2Cl_2$, and washed with sat. $NaHCO_3$. The organic layer was dried over $Na_2SO_4$ and concentrated to give crude products which were submitted to the pyrrole deprotection following the protocol in general procedure A to give 2 or 15.

General Procedure C: Alkyne reduction and pyrrole deprotection: Starting material 38a-e (1 equiv.) was dissolved in MeOH (0.1 M). The solution was degassed for 5 min and 10% wt. Pd/C was added. The reaction was run at RT for 20 h under a hydrogen balloon (1 atm). The crude mixture was then filtered through a pad of celite, and the filtrate was concentrated under reduced pressure. Without any purification, the crude product was submitted to the pyrrole deprotection following the protocol in general procedure A to give 10-14.

General Procedure D: Boc deprotection, alkyne reduction, reductive amination, pyrrole deprotection: Starting material (33a-c, 42, 43, or 45a) was dissolved in $CH_2Cl_2$ (0.1 M) and TFA (1.1 equiv.) was added at 0° C. The reaction was run at RT for 1 h. After that, the solvent and TFA were removed under reduced pressure. The crude mixture was diluted back with $CH_2Cl_2$ and washed with saturated $Na_2CO_3$. The organic layer was then concentrated, and a crude product was carried out to an alkyne reduction without any purification. The crude product (1 equiv.) was dissolved in MeOH (0.1 M) and the solution was degassed for 5 min, followed by an addition of 10% wt. Pd/C. The reaction was run at RT for 20 hours under a hydrogen balloon (1 atm). The crude mixture was then filtered through a pad of celite, and the filtrate was concentrated under reduced pressure. The crude reduction product was diluted with MeOH (0.24 M), followed by an addition of HCHO 37% in $H_2O$ (3 equiv.). The reaction was run at RT for 5 min. After that, the reaction was brought to 0° C. and $NaBH_4$ (3 equiv.) was added slowly. The reaction was further run for 2 hours at RT Upon completion, the reaction was quenched with water, and the methanol was removed under reduced pressure. The aqueous mixture was extracted with ethyl acetate three times, and the organic layers were combined, dried over $Na_2SO_4$, and concentrated to give the crude product, which was submitted to a pyrrole deprotection without any purification. The crude products were then submitted to the pyrrole deprotection following the protocol in general procedure A to give 5, 7, 9, 17, 18, and 19. For compound 4, 6, and 8 which carry only the secondary amine in the tail, their syntheses are followed the same protocol, except the reductive amination with HCHO was omitted.

General Procedure E: Cbz deprotection, reductive amination, pyrrole deprotection: Starting material 45b-c (1 equiv.) was dissolved in MeOH (0.1 M). The solution was degassed for 5 min and 10% of $Pd(OH)_2/C$ was added. The reaction was run at RT for 24 hours under a hydrogen balloon (1 atm). After completion, the reaction mixture was filtered through a pad of celite and the filtrate was concentrated under reduced pressure to give the crude product, which was submitted to a reductive amination with formaldehyde and a pyrrole deprotection following the same protocols described in General Procedure D to give 20-21.

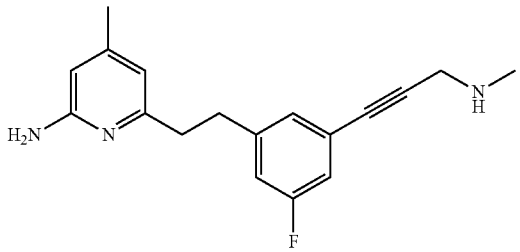 [SMILES: CNCC#Cc1cc(F)cc(CCc2cc(C)cc(N)n2)c1]

6-(3-fluoro-5-(3-(methylamino)prop-1-yn-1-yl)phenethyl)-4-methylpyridin-2-amine (2). Compound 2 (74 mg, 50% for 2 steps) was prepared from 26b (237 mg, 0.5 mmol) according to general procedure B. $^1$H NMR (500 MHz, CD$_3$OD) δ 7.08 (s, 1H), 6.98-6.91 (m, 2H), 6.29 (s, 1H), 6.27 (s, 1H), 3.58 (s, 2H), 2.92 (dd, J=6.5, 9.4 Hz, 2H), 2.79 (dd, J=6.3, 9.2 Hz, 2H), 2.48 (s, 3H), 2.17 (s, 3H). $^{13}$C NMR (126 MHz, CD$_3$OD) δ 162.4 (d, J$_{C-F}$=246.2 Hz), 157.6, 154.4, 147.9, 143.2 (d, J$_{C-F}$=8.1 Hz), 127.8 (d, J$_{C-F}$=2.9 Hz), 123.1 (d, J$_{C-F}$=10.1 Hz), 116.5 (d, J$_{C-F}$=21.5 Hz), 116.3 (d, J$_{C-F}$=23.5 Hz), 113.6, 109.6, 86.5 (d, J$_{C-F}$=3.6 Hz), 79.3, 38.0, 33.7, 33.6, 31.5, 20.6. HRMS-ESI: calculated for C$_{18}$H$_{20}$FN$_3$ [M+H]$^+$ 298.1714, found 298.1716.

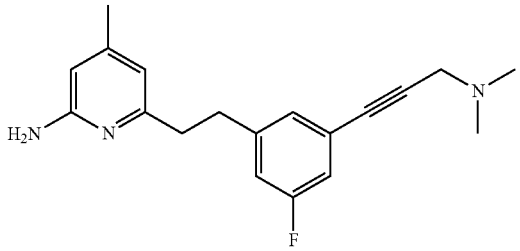 [SMILES: Cc1cc(N)nc(CCc2cc(F)cc(C#CCN(C)C)c2)c1]

6-(3-(3-(dimethylamino)prop-1-yn-1-yl)-5-fluorophenethyl)-4-methylpyridin-2-amine (3). Compound 3 (132 mg, 90%) was prepared from 26b (184 mg, 0.47 mmol) according to general procedure A. $^1$H NMR (500 MHz, CD$_3$OD) δ 7.34 (s, 1H), 7.23-7.14 (m, 2H), 6.69 (s, 1H), 6.62 (s, 1H), 4.36 (s, 2H), 3.38-3.28 (m, 2H), 3.13-2.97 (m, 8H), 2.36 (s, 3H). $^{13}$C NMR (126 MHz, CD$_3$OD) δ 166.4 (d, J$_{C-F}$=246.4 Hz), 161.6, 158.4, 151.9, 147.2 (d, J$_{C-F}$=8.1 Hz), 131.8 (d, J$_{C-F}$=2.8 Hz), 126.7 (d, J$_{C-F}$=10.2 Hz), 120.8 (d, J$_{C-F}$=21.8 Hz), 120.4 (d, J$_{C-F}$=23.7 Hz), 117.5, 113.5, 92.1 (d, J$_{C-F}$=3.5 Hz), 81.8, 69.4, 45.5 (2C), 37.6, 37.5, 24.5. HRMS-ESI: calculated for C$_{19}$H$_{22}$FN$_3$ [M+H]$^+$ 312.1871, found 312.1874.

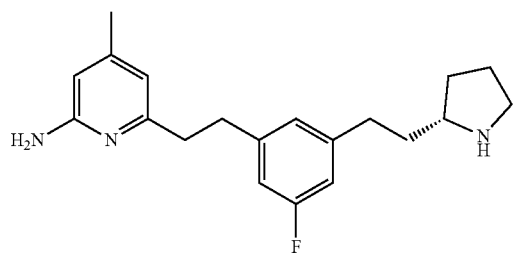 [SMILES: Cc1cc(N)nc(CCc2cc(F)cc(CC[C@@H]3CCCN3)c2)c1]

(R)-6-(3-fluoro-5-(2-(pyrrolidin-2-yl)ethyl)phenethyl)-4-methylpyridin-2-amine (4). Compound 4 (78 mg, 33% for 3 steps) was prepared from 33a (362 mg, 0.7 mmol) according to general procedure D. $^1$H NMR (500 MHz, CD$_3$OD) δ 7.06 (s, 1H), 6.94-6.86 (m, 2H), 6.68 (s, 1H), 6.63 (s, 1H), 3.56-3.50 (m, 1H), 3.36-3.34 (m, 1H), 3.23 (q, J=7.3 Hz, 1H), 3.11-2.98 (m, 4H), 2.76 (t, J=8.0 Hz, 2H), 2.36 (s, 3H), 2.31-2.22 (m, 1H), 2.17-1.94 (m, 4H), 1.79-1.66 (m, 1H). $^{13}$C NMR (126 MHz, CD$_3$OD) δ 161.5 (d, J$_{C-F}$=244.8 Hz), 156.1, 152.9, 146.8, 141.8 (d, J$_{C-F}$=7.8 Hz), 141.0 (d, J$_{C-F}$=7.9 Hz), 122.7, 112.1, 111.4 (d, J$_{C-F}$=21.6 Hz), 111.3 (d, J$_{C-F}$=21.4 Hz), 107.9, 58.5, 43.3, 32.5, 32.4, 31.9, 30.5, 28.2, 21.6, 19.0. HRMS-ESI: calculated for C$_{20}$H$_{26}$FN$_3$ [M+H]$^+$ 328.2184, found 328.2185.

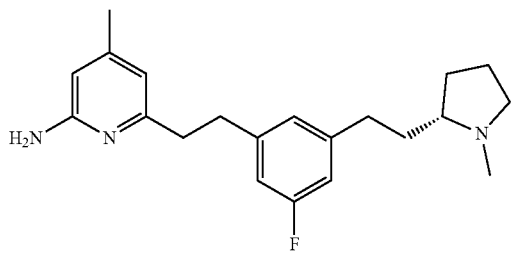 [SMILES: Cc1cc(N)nc(CCc2cc(F)cc(CC[C@@H]3CCCN3C)c2)c1]

(R)-6-(3-fluoro-5-(2-(1-methylpyrrolidin-2-yl)ethyl)phenethyl)-4-methylpyridin-2-amine (5). Compound 5 (41 mg, 15% for 4 steps) was prepared from 33a (401 mg, 0.8 mmol) according to general procedure D. $^1$H NMR (500 MHz, CD$_3$OD) δ 7.06 (s, 1H), 6.91 (dd, J=9.6, 20.1 Hz, 2H), 6.68 (s, 1H), 6.63 (s, 1H), 3.72-3.68 (m, 1H), 3.37-3.36 (m, 1H), 3.23-3.12 (m, 1H), 3.09-2.99 (m, 4H), 2.94 (s, 3H), 2.84-2.67 (m, 2H), 2.47-2.38 (m, 1H), 2.36 (s, 3H), 2.34-2.27 (m, 1H), 2.22-2.03 (m, 2H), 1.97-1.78 (m, 2H). $^{13}$C NMR (126 MHz, CD$_3$OD) δ 163.1 (d, J$_{C-F}$=244.7 Hz), 157.7, 154.4, 148.4, 143.3 (d, J$_{C-F}$=7.5 Hz), 142.6 (d, J$_{C-F}$=7.8 Hz), 124.2, 113.6, 113.0 (d, J$_{C-F}$=21.4 Hz), 112.8 (d, J$_{C-F}$=21.6 Hz), 109.5, 68.7, 55.9, 38.5, 34.0, 33.9, 31.9, 31.7, 29.2, 21.1, 20.5. HRMS-ESI: calculated for C$_{21}$H$_{28}$FN$_3$ [M+H]$^+$ 342.2340, found 342.2342.

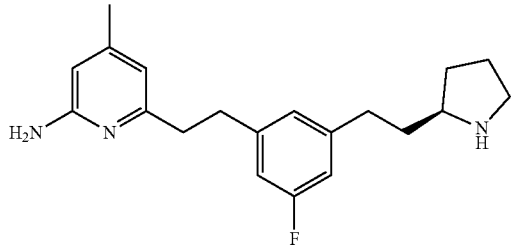 [SMILES: Cc1cc(N)nc(CCc2cc(F)cc(CC[C@H]3CCCN3)c2)c1]

(S)-6-(3-fluoro-5(2-pyrrolidi 2-yl)ethyl)phenethyl)-4-methylpyridin-2-amine (6). Compound 6 (47 mg, 28% for 3 steps) was prepared from 33b (257 mg, 0.5 mmol) according to general procedure D. $^1$H NMR (500 MHz, CD$_3$OD) δ 7.05 (s, 1H), 6.89 (t, J=10.9 Hz, 2H), 6.68 (s, 1H), 6.63 (s, 1H), 3.59-3.45 (m, 2H), 3.40-3.34 (m, 1H), 3.10-2.98 (m, 4H), 2.76 (t, J=8.0 Hz, 2H), 2.36 (s, 3H), 2.32-2.23 (m, 1H), 2.18-1.91 (m, 4H), 1.79-1.62 (m, 1H). $^{13}$C NMR (126 MHz, CD$_3$OD) δ 163.1 (d, J$_{C-F}$=244.9 Hz), 157.7, 154.4, 148.4, 143.4 (d, J$_{C-F}$=7.8 Hz), 142.6 (d, J$_{C-F}$=7.8 Hz), 124.2, 113.6, 112.9 (d, J$_{C-F}$=21.8 Hz), 112.8 (d, J$_{C-F}$=21.6 Hz), 109.4, 60.1, 44.9, 34.0, 33.9, 33.4, 32.0, 29.7, 23.1, 20.5. HRMS-ESI. calculated for C$_{20}$H$_{26}$FN$_3$ [M+H]$^+$ 328.2184, found 328.2180.

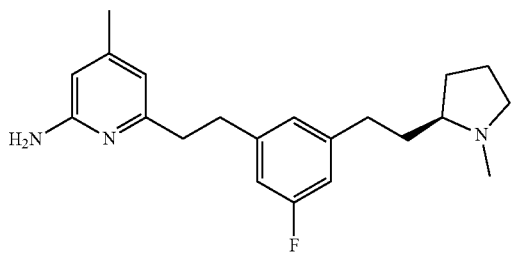 [SMILES: Cc1cc(N)nc(CCc2cc(F)cc(CC[C@H]3CCCN3C)c2)c1]
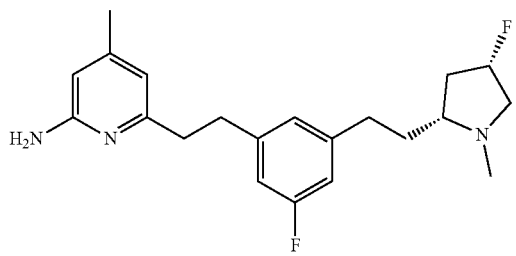

(S)-6-(3-fluoro-5-(2-(1-methylpyrrolidin-2-yl)ethyl)phenethyl)-4-methylpyridin-2-amine (7). Compound 7 (42 mg, 24% for 4 steps) was prepared from 33b (257 mg, 0.5 mmol) according to general procedure D. $^1$H NMR (500 MHz, CD$_3$OD) δ 7.07 (s, 1H), 6.95-6.88 (m, 2H), 6.70 (s, 1H), 6.63 (s, 1H), 3.71 (ddd, J=5.0, 8.0, 11.5 Hz, 1H), 3.34-3.30 (m, 1H), 3.17 (dt, J=8.4, 11.4 Hz, 1H), 3.05 (s, 4H), 2.94 (s, 3H), 2.84-2.67 (m, 2H), 2.45-2.38 (m, 1H), 2.36 (s, 3H), 2.33-2.26 (m, 1H), 2.21-2.04 (m, 2H), 1.98-1.80 (m, 2H). $^{13}$C NMR (126 MHz, CD$_3$OD) δ 163.0 (d, $J_{C-F}$=244.7 Hz), 157.6, 154.4, 148.3, 143.4 (d, $J_{C-F}$=7.8 Hz), 142.6 (d, $J_{C-F}$=7.8 Hz), 124.2, 113.6, 113.0 (d, $J_{C-F}$=21.4 Hz), 112.8 (d, $J_{C-F}$=21.6 Hz), 109.5, 68.7, 55.9, 38.5, 34.1, 33.9, 31.9, 31.7, 29.3, 21.1, 20.6. HRMS-ESI. calculated for C$_{21}$H$_{28}$FN$_3$ [M+H]$^+$ 342.2340, found 342.2341.

6-(3-fluoro-5-(2-((2R,4S)-4-fluoro-1-methylpyrrolidin-2-yl)ethyl)phenethyl)-4-methylpyridin-2-amine (9). Compound 9 (30 mg, 24% for 4 steps) was prepared from 33c (180 mg, 0.35 mmol) according to general procedure D. $^1$H NMR (500 MHz, CD$_3$OD) δ 7.08 (s, 1H), 6.94 (d, J=9.9 Hz, 1H), 6.90 (d, J=9.7 Hz, 1H), 6.68 (s, 1H), 6.64 (s, 1H), 5.45 (dd, J=5.1, 52.5 Hz, 1H), 3.94 (t, J=15.0 Hz, 1H), 3.58-3.46 (m, 2H), 3.07-3.03 (m, 4H), 3.02 (s, 3H), 2.97-2.69 (m, 3H), 2.36 (s, 3H), 2.24-2.09 (m, 2H), 2.01-1.94 (m, 1H). $^{13}$C NMR (126 MHz, CD$_3$OD) δ 163.1 (d, $J_{C-F}$=244.7 Hz), 157.6, 154.4, 148.3, 143.0 (d, $J_{C-F}$=7.7 Hz), 142.7 (d, $J_{C-F}$=7.7 Hz), 124.2, 113.6, 113.0 (d, $J_{C-F}$=21.4 Hz), 112.9 (d, $J_{C-F}$=21.6 Hz), 109.5, 90.6 (d, $J_{C-F}$=176.0 Hz), 67.5, 61.6 (d, $J_{C-F}$=23.5 Hz), 38.4, 36.8 (d, $J_{C-F}$=22.7 Hz), 34.1, 33.9, 32.6, 31.5, 20.5. HRMS-ESI: calculated for C$_{21}$H$_{27}$F$_2$N$_3$ [M+H]$^+$ 360.2246, found 360.2246.

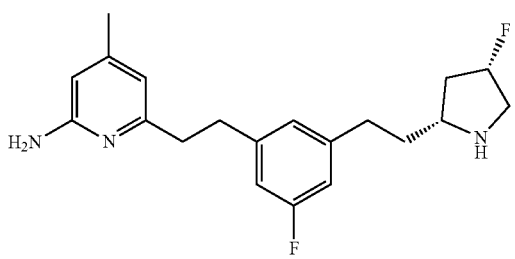 [SMILES: Cc1cc(N)nc(CCc2cc(F)cc(CC[C@@H]3C[C@H](F)CN3)c2)c1]

6-(3-fluoro-5-(2-((2R,4S)-4-fluoropyrrolidin-2-yl)ethyl)phenethyl)-4-methylpyridin-2-amine (8). Compound 8 (62 mg, 30% for 3 steps) was prepared from 33c (310 mg, 0.6 mmol) according to general procedure D. $^1$H NMR (500 MHz, CD$_3$OD) δ 7.08 (s, 1H), 6.88 (dd, J=17.5, 9.6 Hz, 2H), 6.69 (s, 1H), 6.61 (s, 1H), 5.44 (dt, J=3.4, 52.3 Hz, 1H), 3.89-3.80 (m, 1H), 3.71 (ddd, J=3.9, 13.9, 34.7 Hz, 1H), 3.64-3.49 (m, 1H), 3.09-2.99 (m, 4H), 2.85-2.71 (m, 2H), 2.60-2.48 (m, 1H), 2.34 (s, 3H), 2.20 (ddt, J=7.0, 9.3, 14.0 Hz, 1H), 2.14-1.91 (m, 2H). $^{13}$C NMR (126 MHz, CD$_3$OD) δ 162.9 (d, $J_{C-F}$=244.5 Hz), 157.5, 154.2, 148.2, 143.0 (d, $J_{C-F}$=7.4 Hz), 142.4 (d, $J_{C-F}$=7.6 Hz), 124.1, 113.5, 112.9 (d, $J_{C-F}$=21.6 Hz), 112.8 (d, $J_{C-F}$=21.8 Hz), 109.4, 91.9 (d, $J_{C-F}$=175.9 Hz), 58.5, 51.0 (d, $J_{C-F}$=24.7 Hz), 37.5 (d, $J_{C-F}$=20.9 Hz), 33.9, 33.8, 32.9, 31.9, 20.5. HRMS-ESI: calculated for C$_{20}$H$_{25}$F$_2$N$_3$ [M+H]$^+$ 346.2089, found 346.2088.

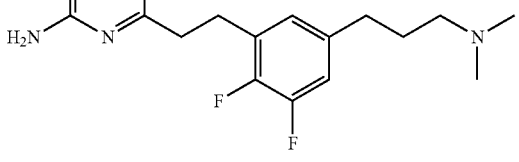

6-(5-(3-(dimethylamino)propyl)-2,3-difluorophenethyl)-4-methylpyridin-2-amine (10). Compound 10 (25 mg, 39% for 2 steps) was prepared from 38a (80 mg, 0.2 mmol) according to general procedure C. $^1$H NMR (500 MHz, CD$_3$OD) δ 7.13-7.06 (m, 2H), 6.71 (s, 1H), 6.60 (s, 1H), 3.21-3.15 (m, 2H), 3.15-3.03 (m, 4H), 2.92 (s, 6H), 2.70 (t, J=7.7 Hz, 2H), 2.36 (s, 3H), 2.11-2.01 (m, 2H). $^{13}$C NMR (126 MHz, CD$_3$OD) δ 157.6, 154.4, 150.1 (dd, $J_{C-F}$ 246.6, 13.3 Hz), 147.9, 147.3 (dd, $J_{C-F}$=244.4, 12.6 Hz), 137.4-137.2 (m), 128.7 (d, $J_{C-F}$=12.5 Hz), 125.3 (t, $J_{C-F}$=3.0 Hz), 115.3 (d, $J_{C-F}$=17.5 Hz), 113.6, 109.6, 56.9, 42.1, 32.7, 31.1, 27.5, 25.7, 20.5. HRMS-ESI: calculated for C$_{19}$H$_{25}$F$_2$N$_3$ [M+H]$^+$ 334.2089, found 334.2089.

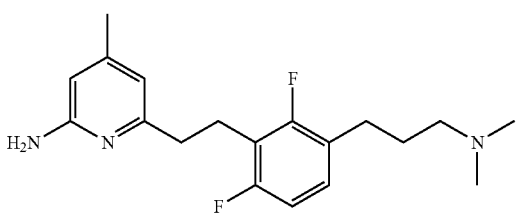

6-(3-(3-(dimethylamino)propyl)-2,6-difluorophenethyl)-4-methylpyridin-2-amine (11). Compound 11 (35 mg, 35% for 2 steps) was prepared from 38b (122 mg, 0.3 mmol) according to general procedure C $^1$H NMR (500 MHz, CD$_3$OD) δ 7.27 (q, J=7.9 Hz, 1H), 6.91 (t, J=8.8 Hz, 1H), 6.73 (s, 1H), 6.49 (s, 1H), 3.24-3.19 (m, 2H), 3.14 (t, J=7.3 Hz, 2H), 3.02 (t, J=7.3 Hz, 2H), 2.92 (s, 6H), 2.73 (t, J=7.7 Hz, 2H), 2.32 (s, 3H), 2.04 (t, J=8.2 Hz, 2H). $^{13}$C NMR (126 MHz, CD$_3$OD) δ 160.0 (dd, J$_{C-F}$=244.8, 8.2 Hz), 159.2 (dd, J$_{C-F}$=245.6, 8.2 Hz), 157.5, 154.4, 147.8, 129.3 (dd, J=6.6, 10.0 Hz), 123.0 (dd, J=3.7, 17.0 Hz), 114.4 (t, J=20.6 Hz), 113.7, 110.7 (dd, J=3.6, 22.3 Hz), 109.7, 56.9, 42.1, 31.9, 25.1 (d, J=2.4 Hz), 24.8, 21.4, 20.5. HRMS-ESI: calculated for C$_{19}$H$_{25}$F$_2$N$_3$ [M+H]$^+$ 334.2089, found 334.2090.

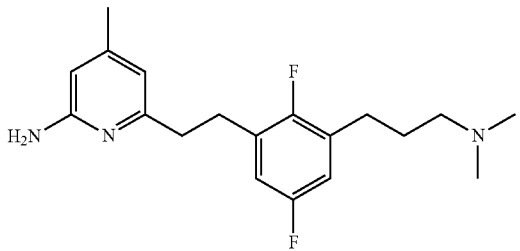

6-(3-(3-(dimethylamino)propyl)-2,5-difluorophenethyl)-4-methylpyridin-2-amine (12). Compound 12 (32 mg, 42% for 2 steps) was prepared from 38c (93 mg, 0.23 mmol) according to general procedure C $^1$H NMR (500 MHz, CD$_3$OD) δ 7.11-6.92 (m, 2H), 6.72 (s, 1H), 6.59 (s, 1H), 3.25-3.18 (m, 2H), 3.14-3.01 (m, 4H), 2.92 (s, 6H), 2.75 (t, J=7.9 Hz, 2H), 2.36 (s, 3H), 2.13-2.01 (m, 2H). $^{13}$C NMR (126 MHz, CD$_3$OD) δ 158.4 (d, J$_{C-F}$=242 Hz), 157.6, 155.2 (d, J$_{C-F}$=241 Hz), 154.4, 147.9, 128.9 (dd, J=8.1, 19.2 Hz), 128.2 (dd, J=8.2, 19.3 Hz), 115.0 (ddd, J=4.7, 20.3, 24.5 Hz, 2C), 113.6, 109.6, 56.9, 42.1, 32.5, 27.7, 25.4, 24.5, 20.6. HRMS-ESI: calculated for C$_{19}$H$_{25}$F$_2$N$_3$ [M+H]$^+$ 334.2089, found 334.2092.

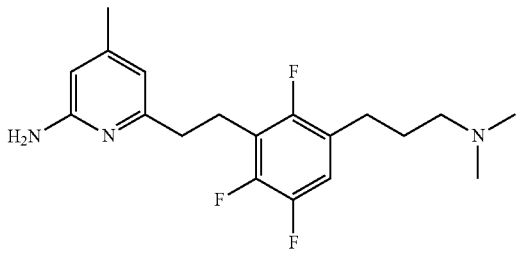

6-(3-(3-(dimethylamino)propyl)-2,5,6-trifluorophenethyl)-4-methylpyridin-2-amine (13). Compound 13 (10 mg, 24% for 2 steps) was prepared from 38d (50 mg, 0.12 mmol) according to general procedure C $^1$H NMR (500 MHz, CD$_3$OD) δ 7.24 (ddd, J=6.9, 8.8, 10.6 Hz, 1H), 6.71 (s, 1H), 6.54 (s, 1H), 3.23-3.13 (m, 4H), 3.03 (t, J=7.4 Hz, 2H), 2.91 (s, 6H), 2.73 (t, J=7.8 Hz, 2H), 2.34 (s, 3H), 2.08-1.96 (m, 2H). $^{13}$C NMR (126 MHz, CD$_3$OD) δ 156.1, 153.0, 152.9 (ddd, J$_{C-F}$=1.3, 5.0, 242.0 Hz), 146.0, 145.8 (ddd, J$_{C-F}$=8.8, 13.9, 245.7 Hz), 145.1 (ddd, J$_{C-F}$=2.5, 12.6, 244.4 Hz), 121.9 (dt, J$_{C-F}$=5.1, 19.2 Hz), 115.2 (dd, J$_{C-F}$=16.6, 23.1 Hz), 114.5 (dd, J$_{C-F}$=5.9, 19.5 Hz), 112.2, 108.3, 55.3, 40.6, 30.2, 23.3, 23.0, 20.2, 19.0. HRMS-ESI: calculated for C$_{19}$H$_{24}$F$_3$N$_3$ [M+H]$^+$ 352.1995, found 352.1996.

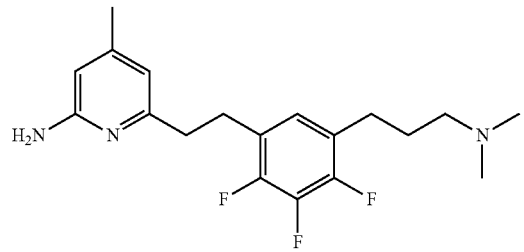 [SMILES: Cc1cc(N)nc(CCc2cc(CCCN(C)C)cc(F)c2F)c1]

6-(5-(3-(dimethylamino)propyl)-2,3,4-trifluorophenethyl)-4-methylpyridin-2-amine (14). Compound 14 (48 mg, 36% for 2 steps) was prepared from 38e (160 mg, 0.37 mmol) according to general procedure C $^1$H NMR (500 MHz, CD$_3$OD) δ 7.15 (td, J=7.6, 2.4 Hz, 1H), 6.64 (s, 1H), 6.58 (s, 1H), 3.24-3.16 (m, 2H), 3.12-2.98 (m, 4H), 2.91 (s, 6H), 2.77 (t, J=7.7 Hz, 2H), 2.34 (s, 3H), 2.11-2.01 (m, 2H). $^{13}$C NMR (126 MHz, CD$_3$OD) δ 156.5, 155.2, 149.3, 148.1 (dd, J$_{C-F}$=245.7, 10.1 Hz, 2C), 139.6 (td, J$_{C-F}$=250.7, 16.4 Hz), 124.8 (dd, J$_{C-F}$=7.6, 3.8 Hz), 124.3 (dd, J$_{C-F}$=13.9, 5.0 Hz), 124.0 (dd, J$_{C-F}$=13.9, 3.8 Hz), 113.6, 109.2, 56.8, 42.1, 33.4, 27.4, 24.7, 24.6, 20.4. HRMS-ESI. calculated for C$_{19}$H$_{24}$F$_3$N$_3$ [M+H]$^+$ 352.1995, found 352.1997.

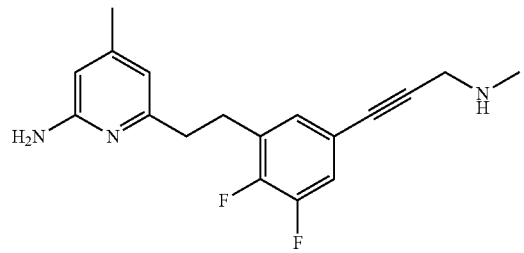

6-(2,3-difluoro-5-(3-(methylamino)prop-1-yn-1-yl)phenethyl)-4-methylpyridin-2-amine (15). Compound 15 (80 mg, 63% for 2 steps) was prepared from 39 (198 mg, 0.4 mmol) according to general procedure B. $^1$H NMR (500 MHz, CD$_3$OD) δ 7.42-7.33 (m, 2H), 6.72 (s, 1H), 6.59 (s, 1H), 4.18 (s, 2H), 3.16 (dd, J=6.3, 9.0 Hz, 2H), 3.06 (dd, J=6.2, 9.0 Hz, 2H), 2.85 (s, 3H), 2.35 (s, 3H). $^{13}$C NMR (126 MHz, CD$_3$OD) δ 157.6, 154.5, 149.9 (dd, J$_{C-F}$=248.4, 13.6 Hz), 149.6 (dd, J$_{C-F}$=250.6, 13.0 Hz), 147.5, 129.8 (d, J$_{C-F}$=13.5 Hz), 129.6-129.4 (m), 118.9 (d, J$_{C-F}$=19.3 Hz), 117.9-117.8 (m), 113.6, 109.8, 85.7, 79.1, 38.0, 32.4, 31.5, 27.2, 20.5. HRMS-ESI. calculated for C$_{18}$H$_{19}$F$_2$N$_3$ [M+H]$^+$ 316.1620, found 316.1618.

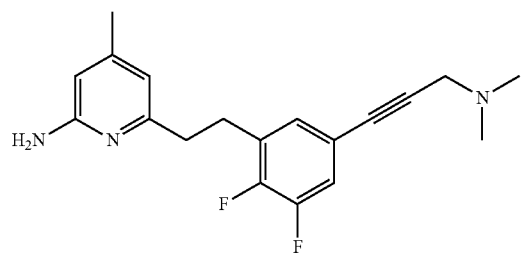

6-(5-(3-(dimethylamino)prop-1-yn-1-yl)-2,3-difluorophenethyl)-4-methylpyridin-2-amine (16). Compound 16 (65 mg, 66%) was prepared from 41 (122 mg, 0.3 mmol)

according to general procedure A. $^1$H NMR (500 MHz, CD$_3$OD) δ 7.45-7.38 (m, 2H), 6.70 (s, 1H), 6.60 (s, 1H), 4.35 (s, 2H), 3.15 (t, J=7.7 Hz, 2H), 3.10-2.98 (m, 8H), 2.36 (s, 3H). $^{13}$C NMR (126 MHz, CD$_3$OD) δ 157.7, 154.5, 150.0 (dd, $J_{C-F}$=248.8, 13.7 Hz), 149.8 (dd, $J_{C-F}$=250.9, 12.9 Hz), 147.6, 129.8 (d, $J_{C-F}$=13.5 Hz), 129.7 (t, $J_{C-F}$=3.5 Hz), 119.1 (d, $J_{C-F}$=19.5 Hz), 117.5 (dd, $J_{C-F}$=8.8, 4.7 Hz), 113.6, 109.8, 87.4, 77.7, 46.9, 41.5 (2C), 32.4, 27.2, 20.5. HRMS-ESI: calculated for C$_{19}$H$_{21}$F$_2$N$_3$ [M+H]$^+$ 330.1776, found 330.1777.

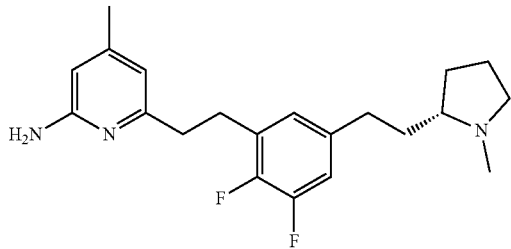 [SMILES: Cc1cc(N)nc(CCc2cc(CC[C@@H]3CCCN3C)cc(F)c2F)c1]

(R)-6-(2,3-difluoro-5-(2-(1-methylpyrrolidin-2-yl)ethyl) phenethyl)-4-methylpyridin-2-amine (17). Compound 17 (55 mg, 46% for 4 steps) was prepared from 42 (173 mg, 0.33 mmol) according to general procedure D. $^1$H NMR (500 MHz, MeOD) δ 7.18-7.06 (m, 2H), 6.71 (s, 1H), 6.60 (s, 1H), 3.77-3.67 (m, 1H), 3.35-3.30 (m, 1H), 3.21-3.15 (m, 1H), 3.15-3.02 (m, 4H), 2.95 (s, 3H), 2.79-2.65 (m, 2H), 2.47-2.38 (m, 1H), 2.36 (s, 3H), 2.33-2.24 (m, 1H), 2.22-2.03 (m, 2H), 1.95-1.80 (m, 2H). $^{13}$C NMR (126 MHz, MeOD) δ 157.6, 154.4, 150.1 (dd, $J_{C-F}$=246.9, 13.0 Hz), 147.9, 147.3 (dd, $J_{C-F}$=244.4, 13.9 Hz), 137.8-137.1 (m), 128.7 (d, $J_{C-F}$=12.4 Hz), 125.3 (d, $J_{C-F}$=3.2 Hz), 115.2 (d, $J_{C-F}$=17.3 Hz), 113.6, 109.6, 68.6, 55.9, 38.5, 32.7, 31.9, 31.2, 29.2, 27.5, 21.1, 20.5. HRMS-ESI: calculated for C$_{21}$H$_{27}$F$_2$N$_3$ [M+H]$^+$ 360.2246 found 360.2247.

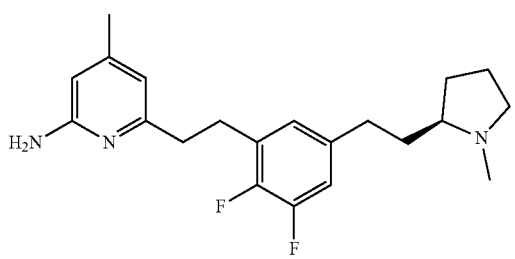 [SMILES: Cc1cc(N)nc(CCc2cc(CC[C@H]3CCCN3C)cc(F)c2F)c1]

(S)-6-(2,3-difluoro-5-(2-(1-methylpyrrolidin-2-yl)ethyl) phenethyl)-4-methylpyridin-2-amine (18). Compound 18 (64 mg, 38% for 4 steps) was prepared from 43 (244 mg, 0.47 mmol) according to general procedure D. $^1$H NMR (500 MHz, CD$_3$OD) δ 7.15-7.07 (m, 2H), 6.70 (s, 1H), 6.60 (s, 1H), 3.71 (ddd, J=5.0, 8.0, 11.6 Hz, 1H), 3.21-3.09 (m, 4H), 3.05 (dd, J=6.6, 9.3 Hz, 2H), 2.95 (s, 3H), 2.80-2.63 (m, 2H), 2.46-2.38 (m, 1H), 2.34-2.24 (m, 1H), 2.21-2.04 (m, 2H), 1.94-1.80 (m, 2H). $^{13}$C NMR (126 MHz, CD$_3$OD) δ 157.7, 154.4, 150.1 (dd, $J_{C-F}$=246.8, 13.4 Hz), 147.9, 147.3 (dd, $J_{C-F}$=244.4, 13.9 Hz), 137.5, 128.7 (d, $J_{C-F}$=12.5 Hz), 125.2, 115.2 (d, $J_{C-F}$=17.3 Hz), 113.6, 109.6, 68.7, 55.9, 38.5, 32.7, 31.9, 31.2, 29.2, 27.5, 21.1, 20.5. HRMS-ESI: calculated for C$_{21}$H$_{27}$F$_2$N$_3$ [M+H]$^+$ 360.2246, found 360.2245.

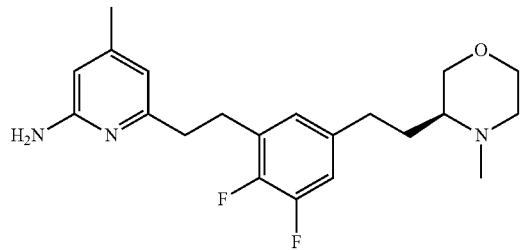 [SMILES: Cc1cc(N)nc(CCc2cc(CC[C@H]3COCCN3C)cc(F)c2F)c1]

(S)-6-(2,3-difluoro-5-(2-(4-methylmorpholin-3-yl)ethyl) phenethyl)-4-methylpyridin-2-amine (19). Compound 19 (68 mg, 28% for 4 steps) was prepared from 45a (346 mg, 0.65 mmol) according to general procedure D. $^1$H NMR (500 MHz, CD$_3$OD) δ 7.19-7.03 (m, 2H), 6.70 (s, 1H), 6.59 (s, 1H), 4.15 (dd, J=13.2, 3.5 Hz, 1H), 4.09-4.01 (m, 1H), 3.93-3.77 (m, 1H), 3.63 (dd, J=13.2, 10.4 Hz, 1H), 3.50 (dd, J=12.9, 2.2 Hz, 1H), 3.30-3.25 (m, 1H), 3.17-3.02 (m, 4H), 2.99 (s, 3H), 2.80-2.59 (m, 2H), 2.36 (s, 3H), 2.32-2.23 (m, 1H), 1.93-1.78 (m, 1H). $^{13}$C NMR (126 MHz, CD$_3$OD) δ 157.7, 154.4, 150 (dd, $J_{C-F}$=248.2, 13.9 Hz), 147.9, 147.4 (dd, $J_{C-F}$=244.4, 12.6 Hz), 137.2 (d, $J_{C-F}$=5.0 Hz), 128.8 (d, $J_{C-F}$=12.5 Hz), 125.3 (d, $J_{C-F}$=3.3 Hz), 115.3 (d, $J_{C-F}$=17.8 Hz), 113.6, 109.6, 67.6, 63.7, 63.3, 54.0, 39.9, 32.7, 30.1, 28.0, 27.5, 20.5. HRMS-ESI. calculated for C$_{21}$H$_{27}$F$_2$N$_3$O [M+H]$^+$ 376.2195, found 376.2197.

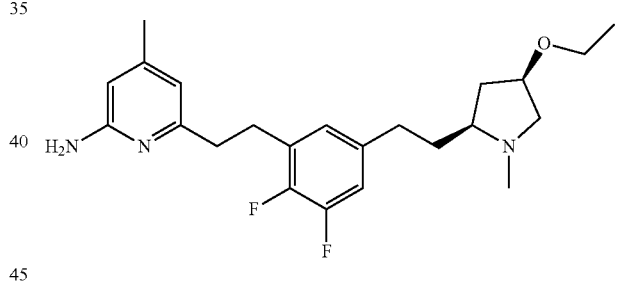

6-(5-(2-((2S,4R)-4-ethoxy-1-methylpyrrolidin-2-yl) ethyl)-2,3-difluorophenethyl)-4-methylpyridin-2-amine (20). Compound 20 (22 mg, 41% for 3 steps) was prepared from 45b (75 mg, 0.13 mmol) according to general procedure E. $^1$H NMR (500 MHz, CD$_3$OD) δ 6.96 (ddd, J=11.3, 7.3, 2.2 Hz, 1H), 6.82 (t, J=5.1, 2.2 Hz, 1H), 6.28 (s, 1H), 6.27 (s, 1H), 3.98 (td, J=6.6, 6.1, 3.5 Hz, 1H), 3.47 (q, J=6.9 Hz, 2H), 3.18 (d, J=11.0 Hz, 1H), 3.00 (t, J=7.8 Hz, 2H), 2.82 (d, J=7.8 Hz, 2H), 2.68-2.59 (m, 1H), 2.54-2.47 (m, 1H), 2.42 (dt, J=13.5, 7.4 Hz, 1H), 2.35 (dd, J=11.0, 5.8 Hz, 1H), 2.31 (s, 3H), 2.17 (s, 3H), 2.06-1.97 (m, 1H), 1.60-1.51 (m, 2H), 1.19 (t, J=7.0 Hz, 3H). $^{13}$C NMR (126 MHz, CD$_3$OD) δ 159.3, 157.5, 150.1 (dd, $J_{C-F}$=245.6, 13.3 Hz), 149.7, 147.0 (dd, $J_{C-F}$=242.9, 12.8 Hz), 138.3 (d, $J_{C-F}$=5.2 Hz), 130.3 (d, $J_{C-F}$=12.7 Hz), 125.1 (t, $J_{C-F}$=3.3 Hz), 114.2 (d, $J_{C-F}$=17.3 Hz), 113.2, 106.7, 76.3, 65.4, 63.9, 62.2, 39.0, 38.4, 37.3, 34.4, 31.6, 28.6, 19.6, 14.3. HRMS-ESI. calculated for C$_{23}$H$_{31}$F$_2$N$_3$O [M+H]$^+$ 404.2508, found 404.2510.

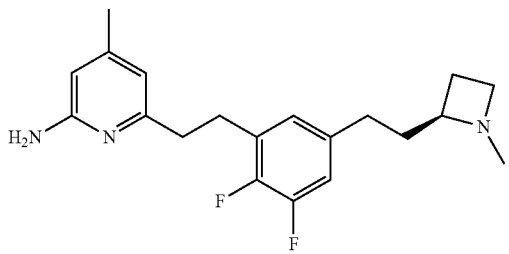 [SMILES: Cc1cc(N)nc(CCc2cc(CC[C@H]3CCN3C)cc(F)c2F)c1]

(S)-6-(2,3-difluoro-5-(2-(1-methylazetidin-2-yl)ethyl)phenethyl)-4-methylpyridin-2-amine (21). Compound 21 (15 mg, 11% for 3 steps) was prepared from 45c (213 mg, 0.4 mmol) according to general procedure E. $^1$H NMR (500 MHz, CD$_3$OD) δ 6.93 (ddd, J=11.3, 7.3, 2.2 Hz, 1H), 6.79 (d, J=6.1 Hz, 1H), 6.27 (s, 2H), 3.38 (td, J=7.7, 2.3 Hz, 1H), 3.05 (qd, J=7.9, 5.9 Hz, 1H), 2.99 (t, J=7.8 Hz, 2H), 2.89-2.84 (m, 1H), 2.82 (d, J=7.8 Hz, 2H), 2.58-2.45 (m, 2H), 2.32 (s, 3H), 2.17 (s, 3H), 2.08-2.01 (m, 1H), 1.93-1.84 (m, 1H), 1.83-1.67 (m, 2H). $^{13}$C NMR (126 MHz, CD$_3$OD) δ 159.4, 157.6, 150.1 (dd, $J_{C-F}$=245.6, 13.2 Hz), 149.6, 147.0 (dd, $J_{C-F}$=242.9, 12.8 Hz), 138.2-138.1 (m), 130.3 (d, $J_{C-F}$=12.7 Hz), 125.1 (t, $J_{C-F}$=3.2 Hz), 114.2 (d, $J_{C-F}$=17.1 Hz), 113.2, 106.7, 68.0, 52.4, 43.4, 37.3, 37.2, 30.5, 28.6, 23.6, 19.6. HRMS-ESI: calculated for C$_{20}$H$_{25}$F$_2$N$_3$ [M+H]$^+$ 346.2089, found 346.2091.

General Procedure SA: Sonogashira Coupling. In a microwave vial, aryl bromide 24 or 37a-e (1 equiv.) and alkyne 25a-b, 32a-c, or 44a-c (1.5-2 equiv.) were added. The mixture was diluted with Et$_3$N/DMF (9:1) to form 0.16 M solution. After the mixture was degassed for 5 min, Pd(PPh$_3$)$_4$ (5-10 mol %) and CuI (5-10 mol %) were added in one portion. The microwave vial was capped, and the reaction mixture was run for 30-40 min at 120° C. in a Biotage microwave reactor. The cap was removed, and the reaction mixture was filtered through a pack of celite. The filtrate was diluted with ethyl acetate and washed with water, ammonium chloride, and brine, dried with Na$_2$SO$_4$, and concentrated under reduced pressure. The crude product mixture was purified by flash column chromatography to give 26a-b, 33a-c, 38a-e, 39, 41, 42, 43, or 45a-c.

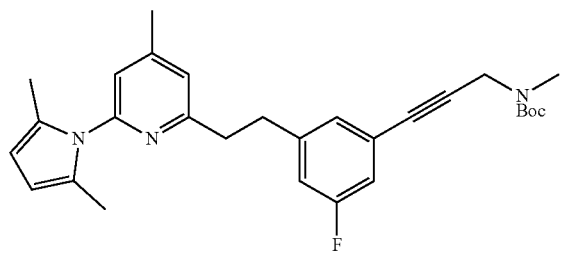 [SMILES: Cc1cc(CCc2cc(F)cc(C#CCN(C)C(=O)OC(C)(C)C)c2)nc(-n2c(C)ccc2C)c1]

tert-butyl (3-(3-(2-(6-(2,5-dimethyl-1H-pyrrol-1-yl)-4-methylpyridin-2-yl)ethyl)-5-fluorophenyl)prop-2-yn-1-yl)(methyl)carbamate (26a). Compound 26a was synthesized according to general procedure SA using aryl bromide 24 (200 mg, 0.65 mmol), alkyne 25a (164 mg, 0.97 mmol), Pd(PPh$_3$)4 (38 mg, 0.0325 mmol), and CuI (6.2 mg, 0.0325 mmol). 26a was isolated as a yellow oil (250 mg, 81%) after flash column chromatography with 10% ethyl acetate/hexane. $^1$H NMR (500 MHz, CDCl$_3$): δ 7.02 (s, 1H), 6.91 (d, J 9.0 Hz, 1H), 6.88 (s, 1H), 6.84 (s, 1H), 6.81 (d, J 9.5 Hz, 1H), 5.86 (s, 2H), 4.24 (brs, 2H), 3.04-3.02 (m, 4H), 2.94 (s, 3H), 2.35 (s, 3H), 2.10 (s, 6H), 1.47 (s, 9H). $^{13}$C NMR (125 MHz, CDCl$_3$): δ 162.4 (d, $J_{C-F}$=244.5 Hz), 160.1, 155.3, 151.7, 149.6, 144.1 (d, $J_{C-F}$=7.5 Hz), 128.5, 127.8 (d, $J_{C-F}$=2.4 Hz), 124.4 (d, $J_{C-F}$=10.0 Hz), 122.7, 120.3, 116.1 (d, $J_{C-F}$=22.9 Hz), 115.8 (d, $J_{C-F}$=21.0 Hz), 106.7, 85.4, 82.5 (d, $J_{C-F}$=3.4 Hz), 80.2, 39.0, 35.1, 35.0, 33.6, 28.4, 21.0, 13.2.

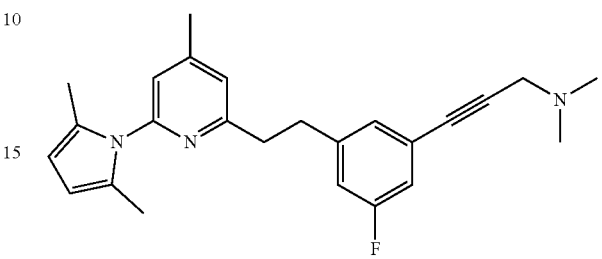

3-(3-(2-(6-(2,5-dimethyl-1H-pyrrol-1-yl)-4-methylpyridin-2-yl)ethyl)-5-fluorophenyl)-N,N-dimethylprop-2-yn-1-amine (26b). Compound 26b was synthesized according to general procedure SA using aryl bromide 24 (194 mg, 0.5 mmol), alkyne 25b (63 mg, 0.75 mmol), Pd(PPh$_3$)4 (29 mg, 0.025 mmol), and CuI (4.7 mg, 0.025 mmol). 26b was isolated as a yellow oil (183 mg, 94%) after flash column chromatography with 5% methanol/dichloromethane. $^1$H NMR (500 MHz, CDCl$_3$): δ 7.03 (s, 1H), 6.93 (d, J 9.0 Hz, 1H), 6.87 (s, 1H), 6.84 (s, 1H), 6.80 (d, J 9.5 Hz, 1H), 5.87 (s, 2H), 3.43 (s, 2H), 3.04-3.02 (m, 4H), 2.35 (s, 3H), 2.34 (s, 6H), 2.10 (s, 6H). $^{13}$C NMR (125 MHz, CDCl$_3$): δ 162.4 (d, $J_{C-F}$=244.4 Hz), 160.2, 151.8, 149.6, 144.1 (d, $J_{C-F}$=8.0 Hz), 128.5, 127.8 (d, $J_{C-F}$=2.4 Hz), 124.7 (d, $J_{C-F}$=10.0 Hz), 122.7, 120.3, 116.1 (d, $J_{C-F}$=22.8 Hz), 115.5 (d, $J_{C-F}$=21.0 Hz), 106.8, 85.4, 84.3 (d, $J_{C-F}$=3.4 Hz), 48.5, 44.3, 39.1, 35.1, 21.0, 13.2. MS ESI [M+H]$^+$=390.04.

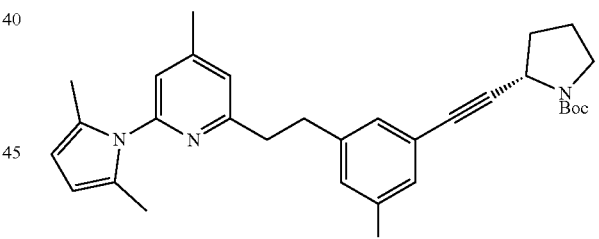

tert-butyl (S)-2-((3-(2-(6-(2,5-dimethyl-1H-pyrrol-1-yl)-4-methylpyridin-2-yl)ethyl)-5-fluorophenyl)ethynyl)pyrrolidine-1-carboxylate (33a). Compound 33a was synthesized according to general procedure SA using aryl bromide 24 (387 mg, 1 mmol), alkyne 32a (292 mg, 1.5 mmol), Pd(PPh$_3$)$_4$ (58 mg, 0.05 mmol), and CuI (9.5 mg, 0.05 mmol). 33a was isolated as a yellow oil (374 mg, 75%) after flash column chromatography with 10% ethyl acetate/hexane. $^1$H NMR (500 MHz, CDCl$_3$) δ 6.99 (s, 1H), 6.93-6.82 (m, 3H), 6.78 (d, J=9.5 Hz, 1H), 5.87 (s, 2H), 4.80-4.49 (m, 1H), 3.56-3.21 (m, 2H), 3.08-2.95 (m, 4H), 2.35 (s, 3H), 2.20-2.00 (m, 9H), 1.91 (s, 1H), 1.47 (s, 9H). $^{13}$C NMR (126 MHz, CDCl$_3$) δ 162.3 (d, $J_{C-F}$=245.5 Hz), 160.2, 154.1, 151.7, 149.6, 144.0, 128.5, 127.6, 124.8 (d, $J_{C-F}$=10.0 Hz), 122.6, 120.3, 115.9 (d, $J_{C-F}$=21.9 Hz), 115.5 (d, $J_{C-F}$=20.8 Hz), 106.7, 90.7, 80.6, 79.7, 48.7, 45.6, 39.1, 35.1, 33.8, 28.6, 23.8, 21.0, 13.2.

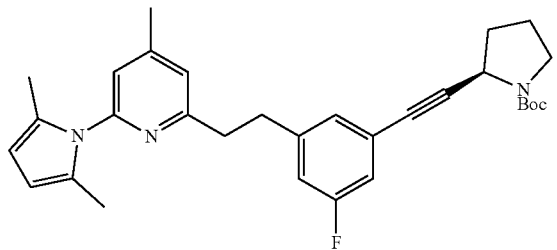 [SMILES: Cc1cc(CCc2cc(F)cc(C#C[C@H]3CCCN3C(=O)OC(C)(C)C)c2)nc(-n2c(C)ccc2C)c1]

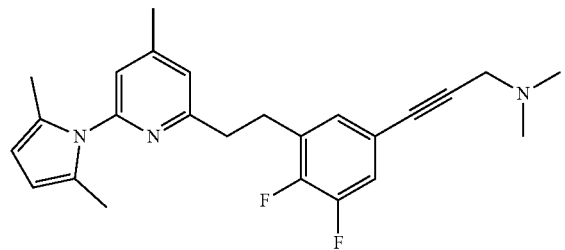

tert-butyl (R)-2-((3-(2-(6-(2,5-dimethyl-1H-pyrrol-1-yl)-4-methylpyridin-2-yl)ethyl)-5-fluorophenyl)ethynyl)pyrrolidine-1-carboxylate (33b). Compound 33b was synthesized according to general procedure SA using aryl bromide 24 (387 mg, 1 mmol), alkyne 32b (292 mg, 1.5 mmol), Pd(PPh$_3$)$_4$ (58 mg, 0.05 mmol), and CuI (9.5 mg, 0.05 mmol). 33b was isolated as a yellow oil (258 mg, 51%) after flash column chromatography with 10% ethyl acetate/hexane. $^1$H NMR (500 MHz, CDCl$_3$) δ 6.99 (s, 1H), 6.93-6.82 (m, 3H), 6.78 (d, J=9.4 Hz, 1H), 5.87 (s, 2H), 4.80-4.50 (m, 1H), 3.58-3.23 (m, 2H), 3.11-2.95 (m, 4H), 2.34 (s, 3H), 2.14-2.00 (m, 9H), 1.91 (s, 1H), 1.47 (s, 9H). $^{13}$C NMR (126 MHz, CDCl$_3$) δ 162.3 (d, J$_{C-F}$=246.3 Hz), 160.2, 154.1, 151.7, 149.6, 144.1, 128.5, 127.6, 124.8 (d, J$_{C-F}$=9.6 Hz), 122.6, 120.3, 115.9 (d, J$_{C-F}$=21.5 Hz), 115.5 (d, J$_{C-F}$=21.0 Hz), 106.7, 90.6, 80.5, 79.7, 48.7, 45.6, 39.1, 35.1, 33.8, 28.5, 23.8, 21.0, 13.2.

3-(3-(2-(6-(2,5-dimethyl-1H-pyrrol-1-yl)-4-methylpyridin-2-yl)ethyl)-4,5-difluorophenyl)-N,N-dimethylprop-2-yn-1-amine (38a). Compound 38a was synthesized according to general procedure SA using aryl bromide 37a (103 mg, 0.5 mmol), alkyne 25b (83 mg, 1 mmol), Pd(PPh$_3$)$_4$ (58 mg, 0.05 mmol), and CuI (9.5 mg, 0.05 mmol). 38a was isolated as a yellow oil (156 mg, 77%) after flash column chromatography with 10% methanol/dichloromethane. $^1$H NMR (500 MHz, CDCl$_3$) δ 7.04 (ddd, J=2.1, 7.1, 10.5 Hz, 1H), 6.97 (dd, J=3.0, 4.9 Hz, 1H), 6.88 (s, 1H), 6.84 (s, 1H), 5.87 (s, 2H), 3.40 (s, 2H), 3.12-2.99 (m, 4H), 2.35 (s, 3H), 2.32 (s, 6H), 2.10 (s, 6H). $^{13}$C NMR (126 MHz, CDCl$_3$) δ 159.9, 151.7, 150.0 (dd, J$_{C-F}$=13.9, 248.2 Hz), 149.6, 149.1 (dd, J$_{C-F}$=12.6, 249.5 Hz), 132.1 (d, J$_{C-F}$=9.9 Hz), 130.9 (d, J$_{C-F}$=13.4 Hz), 129.0, 128.5, 122.6, 120.3, 118.2 (d, J$_{C-F}$=18.5 Hz), 106.7, 85.0, 83.4, 48.5, 44.3, 37.8, 28.6, 21.0, 13.2. MS ESI [M+H]$^+$=408.88.

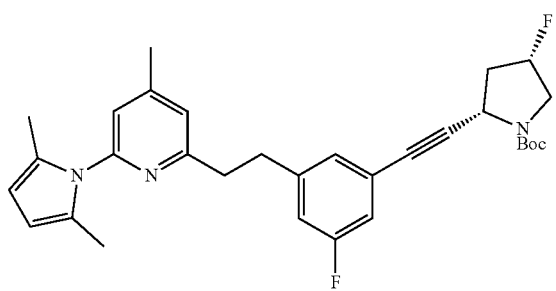 [SMILES: Cc1cc(CCc2cc(F)cc(C#C[C@@H]3C[C@H](F)CN3C(=O)OC(C)(C)C)c2)nc(-n2c(C)ccc2C)c1]

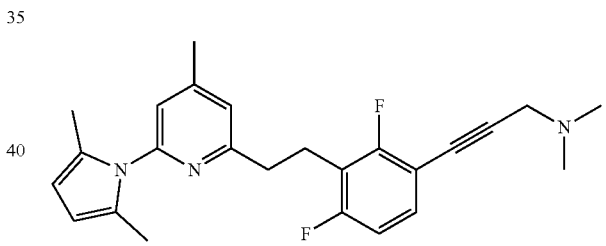

tert-butyl (2S,4S)-2-((3-(2-(6-(2,5-dimethyl-1H-pyrrol-1-yl)-4-methylpyridin-2-yl)ethyl)-5-fluorophenyl)ethynyl)-4-fluoropyrrolidine-1-carboxylate (33c). Compound 33c was synthesized according to general procedure SA using aryl bromide 24 (235 mg, 0.6 mmol), alkyne 32c (194 mg, 0.9 mmol), Pd(PPh$_3$)$_4$ (35 mg, 0.03 mmol), and CuI (5.7 mg, 0.03 mmol). 33c was isolated as a yellow oil (180 mg, 58%) after flash column chromatography with 20% ethyl acetate/hexane. $^1$H NMR (500 MHz, CDCl$_3$) δ 7.00 (s, 1H), 6.90 (d, J=9.5 Hz, 1H), 6.86 (s, 1H), 6.84 (s, 1H), 6.78 (d, J=9.5 Hz, 1H), 5.86 (s, 2H), 5.26 (dt, J=4.2, 52.6 Hz, 1H), 4.83 (d, J=58.0 Hz, 1H), 3.88-3.72 (m, 1H), 3.62 (ddd, J=4.4, 13.2, 35.2 Hz, 1H), 3.05-2.98 (m, 4H), 2.47 (t, J=16.2 Hz, 1H), 2.41-2.23 (m, 4H), 2.10 (s, 6H), 1.48 (s, 9H). $^{13}$C NMR (126 MHz, CDCl$_3$) δ 162.9 (d, J$_{C-F}$=245.5 Hz), 160.2, 154.1, 151.7, 149.6, 144.0, 128.5, 127.6, 124.8 (d, J$_{C-F}$=11.0 Hz), 122.7, 120.3, 115.9 (d, J$_{C-F}$=21.6 Hz), 115.5 (d, J$_{C-F}$=20.1 Hz), 106.7, 90.5 (d, J$_{C-F}$=174.3 Hz), 90.7, 80.4, 79.7, 58.5, 51.0, 39.1, 35.1, 28.5, 23.8, 21.0, 13.2. MS ESI [M+H]$^+$=520.07.

3-(3-(2-(6-(2,5-dimethyl-1H-pyrrol-1-yl)-4-methylpyridin-2-yl)ethyl)-2,4-difluorophenyl)-N,N-dimethylprop-2-yn-1-amine (38b). Compound 38b was synthesized according to general procedure SA using aryl bromide 37b (405 mg, 1 mmol), alkyne 25b (166 mg, 2 mmol), Pd(PPh$_3$)$_4$ (115 mg, 0.1 mmol), and CuI (19 mg, 0.1 mmol). 38b was isolated as a yellow oil (245 mg, 60%) after flash column chromatography with 10% methanol/dichloromethane. $^1$H NMR (500 MHz, CDCl$_3$) δ 7.24-7.19 (m, 1H), 6.84 (s, 2H), 6.75 (td, J=1.4, 8.7 Hz, 1H), 5.86 (s, 2H), 3.48 (s, 2H), 3.11-2.98 (m, 4H), 2.35 (s, 6H), 2.33 (s, 3H), 2.09 (s, 6H). $^{13}$C NMR (126 MHz, CDCl$_3$) δ 161.7 (dd, J$_{C-F}$=8.8, 252.0 Hz), 161.1 (dd, J$_{C-F}$=7.6, 249.5 Hz), 160.1, 151.7, 149.4, 131.3 (dd, J$_{C-F}$=2.7, 10.0 Hz), 128.5, 122.4, 120.2, 117.2 (t, J$_{C-F}$=20.5 Hz), 111.0 (dd, J$_{C-F}$=3.9, 23.4 Hz), 107.7 (dd, J$_{C-F}$=3.8, 17.6 Hz), 106.6, 89.2, 78.1, 48.6, 44.1, 37.3, 22.7, 20.9, 13.2.

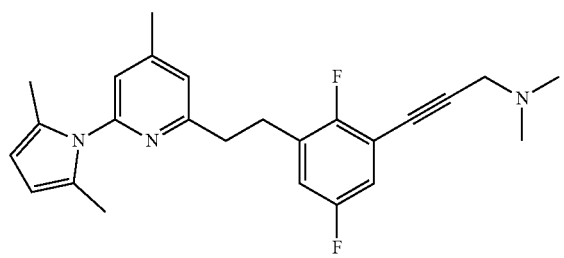 [SMILES: Cc1cc(CCc2cc(F)cc(C#CCN(C)C)c2F)nc(-n2c(C)ccc2C)c1]

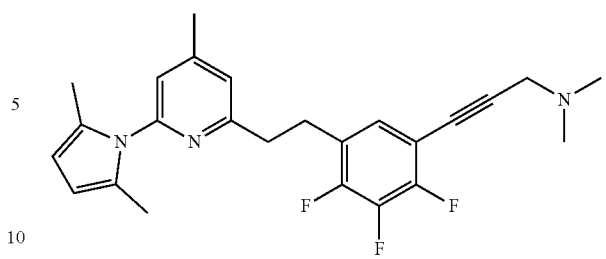

3-(3-(2-(6-(2,5-dimethyl-1H-pyrrol-1-yl)-4-methylpyridin-2-yl)ethyl)-2,5-difluorophenyl)-N,N-dimethylprop-2-yn-1-amine (38c). Compound 38c was synthesized according to general procedure SA using aryl bromide 37c (203 mg, 0.5 mmol), alkyne 25b (83 mg, 1 mmol), Pd(PPh$_3$)$_4$ (58 mg, 0.05 mmol), and CuI (9.5 mg, 0.05 mmol). 38c was isolated as a yellow oil (191 mg, 94%) after flash column chromatography with 10% methanol/dichloromethane. $^1$H NMR (500 MHz, CDCl$_3$) δ 6.92 (ddd, J=3.2, 5.1, 8.3 Hz, 1H), 6.88 (s, 1H), 6.85 (s, 1H), 6.76 (ddd, J=3.2, 5.5, 8.6 Hz, 1H), 5.87 (s, 2H), 3.50 (s, 2H), 3.09-3.00 (m, 4H), 2.35 (s, 6H), 2.35 (s, 3H), 2.09 (s, 6H). $^{13}$C NMR (126 MHz, CDCl$_3$) δ 159.9, 157.6 (ddd, J$_{C-F}$=3.8, 18.9, 243.2 Hz), 151.7, 149.6, 131.2 (ddd, J$_{C-F}$=8.2, 18.5, 234.4 Hz), 128.5 (d, J$_{C-F}$=12.6 Hz), 128.5, 122.6, 120.3, 117.3, 117.1, 112.5 (dd, J$_{C-F}$=10.4, 19.6 Hz), 106.7, 90.8 (d, J$_{C-F}$=3.8 Hz), 78.1 (d, J$_{C-F}$=2.7 Hz), 48.6, 44.2, 37.6, 29.0, 21.0, 13.2.

3-(5-(2-(6-(2,5-dimethyl-1H-pyrrol-1-yl)-4-methylpyridin-2-yl)ethyl)-2,3,4-trifluorophenyl)-N,N-dimethylprop-2-yn-1-amine (38e). Compound 38e was synthesized according to general procedure SA using aryl bromide 37e (411 mg, 0.97 mmol), alkyne 25b (161 mg, 1.94 mmol), Pd(PPh$_3$)$_4$ (112 mg, 0.097 mmol), and CuI (18 mg, 0.097 mmol). 38e was isolated as a yellow oil (380 mg, 92%) after flash column chromatography with 40% ethylacetate/dichloromethane. $^1$H NMR (500 MHz, CDCl$_3$) δ 6.94 (td, J=7.3, 2.4 Hz, 1H), 6.88 (s, 1H), 6.85 (s, 1H), 5.87 (s, 2H), 3.47 (s, 2H), 3.08-2.98 (m, 4H), 2.35 (s, 3H), 2.33 (s, 6H), 2.09 (s, 6H). $^{13}$C NMR (126 MHz, CDCl$_3$) δ 159.7, 151.8, 151.4-149.2 (m), 150.7-148.5 (m), 149.7, 140.0 (dt, J$_{C-F}$=251.0, 15.8 Hz), 128.5, 127.6 (t, J$_{C-F}$=4.3 Hz), 125.4 (dd, J$_{C-F}$=13.9, 4.1 Hz), 122.6, 120.4, 108.6 (dd, J$_{C-F}$=12.7, 4.0 Hz), 106.8, 90.7 (2×C), 48.5, 44.1, 37.7, 28.3, 21.0, 13.2. MS ESI [M+H]$^+$=426.46.

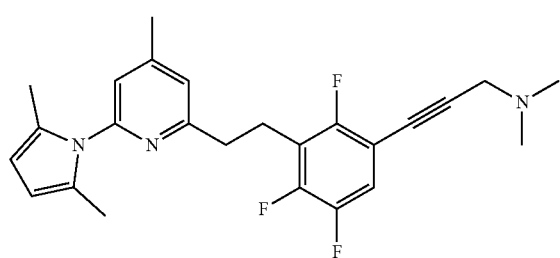 [SMILES: Cc1cc(CCc2c(F)c(F)cc(C#CCN(C)C)c2F)nc(-n2c(C)ccc2C)c1]

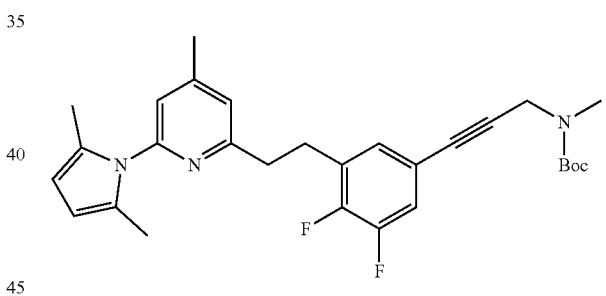

3-(3-(2-(6-(2,5-dimethyl-1H-pyrrol-1-yl)-4-methylpyridin-2-yl)ethyl)-2,4,5-trifluorophenyl)-N,N-dimethylprop-2-yn-1-amine (38d). Compound 38d was synthesized according to general procedure SA using aryl bromide 37d (211 mg, 0.5 mmol), alkyne 25b (83 mg, 1 mmol), Pd(PPh$_3$)$_4$ (58 mg, 0.05 mmol), and CuI (9.5 mg, 0.05 mmol). 38d was isolated as a yellow oil (106 mg, 50%) after flash column chromatography with 50% ethylacetate/dichloromethane. $^1$H NMR (500 MHz, CDCl$_3$) δ 7.06 (ddd, J=6.5, 8.6, 10.0 Hz, 1H), 6.89-6.80 (m, 2H), 5.86 (s, 2H), 3.47 (s, 2H), 3.14-2.98 (m, 4H), 2.34 (s, 3H), 2.34 (s, 6H), 2.09 (s, 6H). $^{13}$C NMR (126 MHz, CDCl$_3$) δ 162.5, 159.7, 159.7-158.2 (m), 151.8, 150.1-147.7 (m), 149.5, 146.4 (ddd, J$_{C-F}$=244.2, 13.1, 2.5 Hz), 128.5, 122.4, 120.4, 119.2 (dd, J$_{C-F}$=21.8, 17.4 Hz), 117.9 (d, J$_{C-F}$=20.6 Hz), 106.7, 90.5 (2×C), 48.6, 44.2, 37.1, 23.0, 20.9, 13.2.

tert-butyl (3-(3-(2-(6-(2,5-dimethyl-1H-pyrrol-1-yl)-4-methylpyridin-2-yl)ethyl)-4,5-difluorophenyl)prop-2-yn-1-yl)(methyl)carbamate (39). Compound 39 was synthesized according to general procedure SA using aryl bromide 37a (203 mg, 0.5 mmol), alkyne 25a (169 mg, 1 mmol), Pd(PPh$_3$)$_4$ (58 mg, 0.05 mmol), and CuI (9.5 mg, 0.05 mmol). 39 was isolated as a yellow oil (197 mg, 80%) after flash column chromatography with 20% ethyl acetate/hexane. $^1$H NMR (500 MHz, CDCl$_3$) δ 7.03 (ddd, J=2.0, 7.2, 9.9 Hz, 1H), 6.97 (dt, J=1.8, 6.0 Hz, 1H), 6.88 (s, 1H), 6.85 (s, 1H), 5.87 (s, 2H), 4.22 (s, 2H), 3.11-3.00 (m, 4H), 2.92 (s, 3H), 2.35 (s, 3H), 2.10 (s, 6H), 1.46 (s, 9H). $^{13}$C NMR (126 MHz, CDCl$_3$) δ 159.9, 155.3, 151.7, 149.9 (dd, J$_{C-F}$=14.0, 248.6 Hz), 149.6, 149.1 (dd, J$_{C-F}$=12.4, 249.7 Hz), 132.1 (d, J$_{C-F}$=9.8 Hz), 131.0 (d, J$_{C-F}$=13.9 Hz), 129.1, 128.5, 122.6, 120.4, 118.2 (d, J$_{C-F}$=18.8 Hz), 106.7, 85.0, 81.7, 80.2, 39.7, 37.7, 33.6, 28.6, 28.4, 21.0, 13.2.

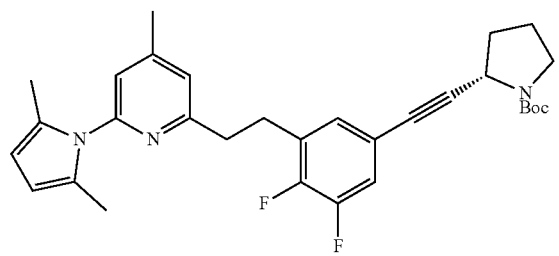 [SMILES: Cc1cc(CCc2cc(C#C[C@@H]3CCCN3C(=O)OC(C)(C)C)cc(F)c2F)nc(-n2c(C)ccc2C)c1]

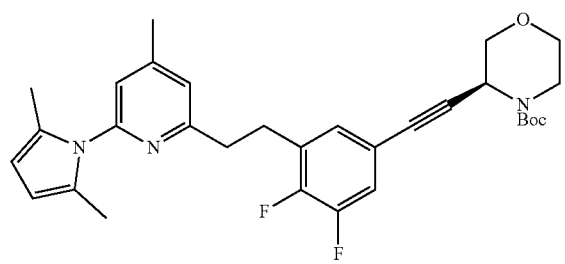

tert-butyl (S)-2-((3-(2-(6-(2,5-dimethyl-1H-pyrrol-1-yl)-4-methylpyridin-2-yl)ethyl)-4,5-difluorophenyl)ethynyl)pyrrolidine-1-carboxylate (42). Compound 42 was synthesized according to general procedure SA using aryl bromide 37a (203 mg, 0.5 mmol), alkyne 32a (195 mg, 1 mmol), Pd(PPh$_3$)$_4$ (58 mg, 0.05 mmol), and CuI (9.5 mg, 0.05 mmol). 42 was isolated as a yellow oil (170 mg, 66%) after flash column chromatography with 15% ethyl acetate/hexane. $^1$H NMR (500 MHz, Chloroform-d) δ 7.00 (s, 1H), 6.95 (s, 1H), 6.88 (s, 1H), 6.84 (s, 1H), 5.87 (s, 2H), 4.63 (d, J=65.1 Hz, 1H), 3.40 (d, J=69.7 Hz, 2H), 3.13-2.96 (m, 4H), 2.35 (s, 3H), 2.10 (s, 6H), 2.08-1.84 (m, 4H), 1.46 (s, 9H). $^{13}$C NMR (126 MHz, CDCl$_3$) δ 160.0, 154.1, 151.8, 149.8 (dd, J$_{C-F}$=13.4, 248.6 Hz), 149.6, 149.0 (dd, J$_{C-F}$=12.4, 249.7 Hz), 132.0 (d, J$_{C-F}$=9.5 Hz), 131.0 (d, J$_{C-F}$=13.9 Hz), 129.0, 128.5, 122.5, 120.3, 118.2 (d, J$_{C-F}$=18.5 Hz), 106.7, 90.6, 80.5, 79.7, 48.5, 45.6, 37.8, 33.6, 33.1, 28.6, 28.5, 21.0, 13.2.

tert-butyl (S)-3-((3-(2-(6-(2,5-dimethyl-1H-pyrrol-1-yl)-4-methylpyridin-2-yl)ethyl)-4,5-difluorophenyl)ethynyl)morpholine-4-carboxylate (45a). Compound 45a was synthesized according to general procedure SA using aryl bromide 37a (460 mg, 1.1 mmol), alkyne 44a (286 mg, 1.3 mmol), Pd(PPh$_3$)$_4$ (130 mg, 0.011 mmol), and CuI (21 mg, 0.011 mmol). 45a was isolated as a yellow oil (435 mg, 72%) after flash column chromatography with 20% ethyl acetate/hexane. $^1$H NMR (500 MHz, CDCl$_3$) δ 7.06 (ddd, J=10.4, 7.1, 2.0 Hz, 1H), 7.01 (dt, J=6.0, 1.8 Hz, 1H), 6.88 (s, 1H), 6.85 (s, 1H), 5.86 (s, 2H), 4.89 (s, 1H), 3.94 (d, J=11.3 Hz, 1H), 3.90 (dd, J=11.8, 3.1 Hz, 1H), 3.72 (d, J=12.9 Hz, 1H), 3.63 (dd, J=11.3, 3.2 Hz, 1H), 3.47 (td, J=11.8, 2.7 Hz, 1H), 3.32 (t, J=11.7 Hz, 1H), 3.11-2.99 (m, 4H), 2.35 (s, 3H), 2.10 (s, 6H), 1.47 (s, 9H). $^{13}$C NMR (126 MHz, CDCl$_3$) δ 159.9, 154.4, 151.8, 149.8 (dd, J$_{C-F}$=13.0, 248.5 Hz), 149.6, 149.0 (dd, J$_{C-F}$=13.0, 245.5 Hz), 130.9 (d, J$_{C-F}$=13.2 Hz), 129.3 (t, J$_{C-F}$=3.4 Hz), 128.5, 122.6, 120.4, 118.7-118.6 (m), 118.5, 118.4, 106.7 (2×C), 86.3, 81.9, 80.9, 70.0, 66.9, 60.4, 37.8, 28.7, 28.4, 21.0, 13.2. MS ESI [M+H]$^+$=536.11.

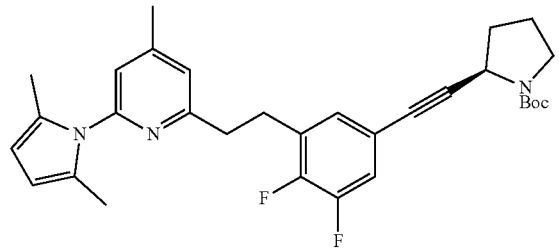 [SMILES: Cc1cc(CCc2cc(C#C[C@H]3CCCN3C(=O)OC(C)(C)C)cc(F)c2F)nc(-n2c(C)ccc2C)c1]

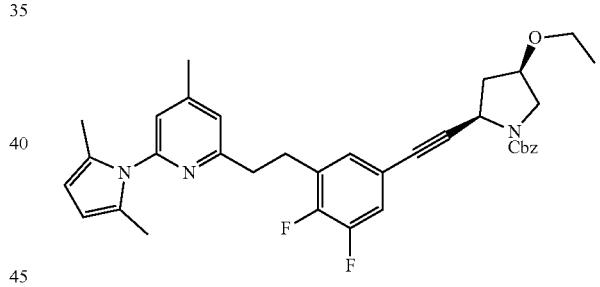

tert-butyl (R)-2-((3-(2-(6-(2,5-dimethyl-1H-pyrrol-1-yl)-4-methylpyridin-2-yl)ethyl)-4,5-difluorophenyl)ethynyl)pyrrolidine-1-carboxylate (43). Compound 43 was synthesized according to general procedure SA using aryl bromide 37a (297 mg, 0.7 mmol), alkyne 32b (205 mg, 1 mmol), Pd(PPh$_3$)$_4$ (81 mg, 0.07 mmol), and CuI (13 mg, 0.07 mmol). 43 was isolated as a yellow oil (242 mg, 67%) after flash column chromatography with 15% ethyl acetate/hexane. $^1$H NMR (500 MHz, CDCl$_3$) δ 7.00 (s, 1H), 6.95 (s, 1H), 6.88 (s, 1H), 6.84 (s, 1H), 5.87 (s, 2H), 4.63 (d, J=64.7 Hz, 1H), 3.40 (d, J=70.6 Hz, 2H), 3.10-2.95 (m, 4H), 2.35 (s, 3H), 2.10 (s, 6H), 2.07-1.88 (m, 4H), 1.46 (s, 9H). $^{13}$C NMR (126 MHz, CDCl$_3$) δ 160.0, 154.1, 151.8, 149.8 (dd, J$_{C-F}$=12.4, 249.5 Hz), 149.6, 149.0 (dd, J$_{C-F}$=13.0, 248.5 Hz), 132.0 (d, J$_{C-F}$=9.4 Hz), 131.0 (d, J$_{C-F}$=13.1 Hz), 129.0, 128.5, 122.5, 120.4, 118.2 (d, J$_{C-F}$=18.4 Hz), 106.7, 90.2, 80.5, 79.7, 48.6, 45.6, 37.8, 33.8, 33.2, 28.6, 28.5, 21.0, 13.2.

Benzyl (2R,4R)-2-((3-(2-(6-(2,5-dimethyl-1H-pyrrol-1-yl)-4-methylpyridin-2-yl)ethyl)-4,5-difluorophenyl)ethynyl)-4-ethoxypyrrolidine-1-carboxylate (45b). Compound 45b was synthesized according to general procedure SA using aryl bromide 37a (300 mg, 0.74 mmol), alkyne 44b (223 mg, 0.81 mmol), Pd(PPh$_3$)$_4$ (85 mg, 0.074 mmol), and CuI (14 mg, 0.074 mmol). 45b was isolated as a yellow oil (221 mg, 50%) after flash column chromatography with 25% ethyl acetate/hexane. $^1$H NMR (500 MHz, CDCl$_3$) δ 7.43-7.24 (m, 5H), 7.02 (d, J=17.7 Hz, 1H), 6.95-6.90 (m, 1H), 6.87 (s, 1H), 6.84 (s, 1H), 5.87 (s, 2H), 5.24 (d, J=12.4 Hz, 1H), 5.08 (d, J=12.9 Hz, 1H), 4.81-4.71 (m, 1H), 4.10 (q, J=7.2 Hz, 2H), 4.08 (m, 1H), 3.66-3.46 (m, 2H), 3.11-2.95 (m, 4H), 2.35 (s, 3H), 2.29 (m, 2H), 2.10 (s, 6H), 1.24 (t, J=7.1 Hz, 3H). $^{13}$C NMR (126 MHz, CDCl$_3$) δ 160.0, 154.4, 151.8, 149.8 (dd, J$_{C-F}$=13.0, 248.5 Hz), 149.6, 149.0 (dd, J$_{C-F}$=12.9, 248.0 Hz), 136.7 (d, J$_{C-F}$=11.9 Hz), 130.8, 129.0 (d, J$_{C-F}$=24.5 Hz), 128.5, 128.4, 128.2-127.9 (m, 1C), 127.7, 122.5, 120.3, 119.2, 118.3 (d, J$_{C-F}$=18.6 Hz), 106.7, 89.8, 80.5, 76.3, 67.1, 64.3, 60.4, 52.1, 47.1, 37.8, 28.6, 21.1, 15.4, 13.2.

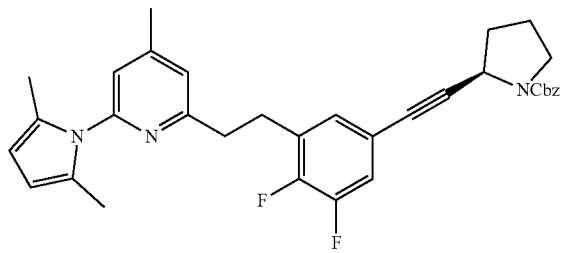 [SMILES: Cc1cc(CCc2cc(C#C[C@H]3CCCN3C(=O)OCc3ccccc3)cc(F)c2F)nc(-n2c(C)ccc2C)c1]

Benzyl (R)-2-((3-(2-(6-(2,5-dimethyl-1H-pyrrol-1-yl)-4-methylpyridin-2-yl)ethyl)-4,5-difluorophenyl)ethynyl)azetidine-1-carboxylate (45c). Compound 45c was synthesized according to general procedure SA with some modifications. Aryl bromide 37a (122 mg, 0.3 mmol) and alkyne 44c (71 mg, 0.33 mmol) were dissolved in DEA:DMF (1:1) and the mixture was degassed for 5 min. Pd(PPh$_3$)$_2$Cl$_2$ (10.5 mg, 0.015 mmol), CuI (3 mg, 0.015 mmol) and PPh$_3$ (16 mg, 0.06 mmol) were added subsequently. The reaction was run at 120° C. in 20 min in microwave reactor. 45c was isolated as a yellow oil (123 mg, 76%) after flash column chromatography with 25% ethyl acetate/hexane. $^1$H NMR (500 MHz, CDCl$_3$) δ 7.40-7.24 (m, 5H), 7.06-6.96 (m, 2H), 6.88 (s, 1H), 6.85 (s, 1H), 5.87 (s, 2H), 5.19 (d, J=12.6 Hz, 1H), 5.07 (d, J=12.4 Hz, 1H), 5.00 (dd, J=8.8, 6.0 Hz, 1H), 4.05 (td, J=8.7, 5.6 Hz, 1H), 3.95 (td, J=8.7, 6.5 Hz, 1H), 3.12-2.98 (m, 4H), 2.66-2.56 (m, 1H), 2.42-2.31 (m, 1H), 2.35 (s, 3H), 2.10 (s, 6H). $^{13}$C NMR (126 MHz, CDCl$_3$) δ 159.9, 156.0, 151.8, 150.0 (dd, J$_{C-F}$=13.8, 248.6 Hz), 149.6, 149.0 (dd, J$_{C-F}$=12.8, 249.0 Hz) 136.6, 134.7 (d, J$_{C-F}$=6.6 Hz), 131.0 (d, J$_{C-F}$=13.7 Hz), 130.1 (d, J$_{C-F}$=11.3 Hz), 129.2, 128.5, 128.4, 128.0, 122.5, 120.4, 118.4 (d, J$_{C-F}$=18.9 Hz), 106.7, 88.0, 83.7, 66.7, 51.0, 47.1, 37.8, 28.6, 24.4, 21.0, 13.2. MS ESI [M+H]$^+$=540.07.

General Procedure SB: Pyrrolyl-lutidine and Aryl Bromide Coupling. In a flame-dry round bottom flask, n-BuLi 1.6 M/THF (1.1-1.2 equiv.) was added and diluted with THF to form 0.8 M solution. At −78° C., 22 (1 M in THF, 1 equiv.) was added dropwise to the n-BuLi solution. The reaction was then run at −20° C. for 15 min. After that, the reaction was brought back to −78° C. and aryl bromide 23 or 36a-e (1 M in THF, 1.1-1.2 equiv.) was added dropwise to the reaction mixture. The reaction was run for 20 min at −20° C. before quenching with saturated NH$_4$Cl solution. The crude reaction mixture was partitioned between ethyl acetate and water, and the organic layer was washed with H$_2$O and brine, dried with Na$_2$SO$_4$, and concentrated under reduced pressure. The crude product was purified by flash column chromatography to give 24 or 37a-e.

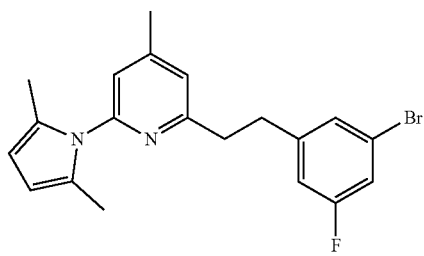 [SMILES: Cc1cc(CCc2cc(F)cc(Br)c2)nc(-n2c(C)ccc2C)c1]

2-(3-bromo-5-fluorophenethyl)-6-(2,5-dimethyl-1H-pyrrol-1-yl)-4-methylpyridine (24). Compound 24 was synthesized according to general procedure SB using 22 (2 g, 10 mmol) and 23 (3.08 g, 11 mmol). 24 was isolated as a light-yellow oil (2.55 g, 66%) after flash column chromatography 5% ethyl acetate/hexanes. $^1$H NMR (500 MHz, CDCl$_3$) δ 7.10 (t, J=1.6 Hz, 1H), 7.06 (dt, J=8.2, 2.1 Hz, 1H), 6.90 (s, 1H), 6.87 (s, 1H), 6.82 (dt, J=9.4, 2.2 Hz, 1H), 5.89 (s, 2H), 3.05-2.98 (m, 4H), 2.37 (s, 3H), 2.12 (s, 6H). $^{13}$C NMR (126 MHz, CDCl$_3$) δ 162.6 (d, J$_{C-F}$=0.9, 151.250.1 Hz), 1598, 149.7, 145.6 (d, J$_{C-F}$=7.8 Hz), 128.5, 127.6 (d, J$_{C-F}$=2.9 Hz), 122.7, 122.3 (d, J$_{C-F}$=10.1 Hz), 120.4, 116.7 (d, J$_{C-F}$=24.5 Hz), 114.4 (d, J$_{C-F}$=20.9 Hz), 106.8, 39.0, 35.0, 21.0, 13.2.

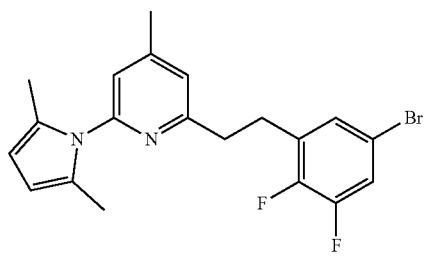 [SMILES: Cc1cc(CCc2cc(Br)cc(F)c2F)nc(-n2c(C)ccc2C)c1]

2-(5-bromo-2,3-difluorophenethyl)-6-(2,5-dimethyl-1H-pyrrol-1-yl)-4-methylpyridine (37a). Compound 37a was synthesized according to general procedure SB using 22 (1 g, 5 mmol) and 36a (1.57 g, 5.5 mmol). 37a was isolated as a light-yellow oil (1.14 g, 56%) after flash column chromatography 5% ethyl acetate/hexanes. $^1$H NMR (500 MHz, CDCl$_3$) δ 7.14 (ddd, J=2.5, 6.7, 9.3 Hz, 1H), 7.01 (dd, J=2.6, 5.0 Hz, 1H), 6.88 (s, 1H), 6.86 (s, 1H), 5.88 (s, 2H), 3.17-2.87 (m, 4H), 2.36 (s, 3H), 2.10 (s, 6H). $^{13}$C NMR (126 MHz, CDCl$_3$) δ 159.6, 151.8, 150.5 (dd, J$_{C-F}$=13.9, 252.0 Hz), 149.7, 132.5 (d, J$_{C-F}$=13.8 Hz), 148.4 (dd, J$_{C-F}$=11.3, 245.7 Hz), 128.5, 128.4, 122.6, 120.4, 118.5 (d, J$_{C-F}$=20.2 Hz), 106.8, 37.6, 28.6, 21.0, 13.2.

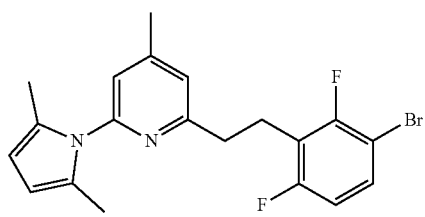 [SMILES: Cc1cc(CCc2c(F)ccc(Br)c2F)nc(-n2c(C)ccc2C)c1]

2-(3-bromo-2,6-difluorophenethyl)-6-(2,5-dimethyl-1H-pyrrol-1-yl)-4-methylpyridine (37b). Compound 37b was synthesized according to general procedure SB using 22 (500 mg, 2.5 mmol) and 36b (786 mg, 2.75 mmol). 37b was isolated as a light-yellow oil (725 mg, 71%) after flash column chromatography 5% ethyl acetate/hexanes. $^1$H NMR (500 MHz, CDCl$_3$) δ 7.37-7.30 (m, 1H), 6.87-6.83 (m, 2H), 6.74 (td, J=1.7, 8.7 Hz, 1H), 5.86 (s, 2H), 3.15-3.08 (m, 2H), 3.07-2.97 (m, 2H), 2.34 (s, 3H), 2.10 (s, 6H). $^{13}$C NMR (126 MHz, CDCl$_3$) δ 160.6 (dd, J$_{C-F}$=7.6, 248.2 Hz), 159.9, 157.7 (dd, J$_{C-F}$=9.1, 247.3 Hz), 151.7, 149.5, 130.8 (d, J$_{C-F}$=9.6 Hz), 128.5, 122.4, 120.3, 118.6 (t, J$_{C-F}$=21.3 Hz), 112.2 (dd, J$_{C-F}$=3.8, 23.9 Hz), 106.7, 103.7 (dd, J$_{C-F}$=4.0, 22.3 Hz), 37.2, 23.2, 20.9, 13.2.

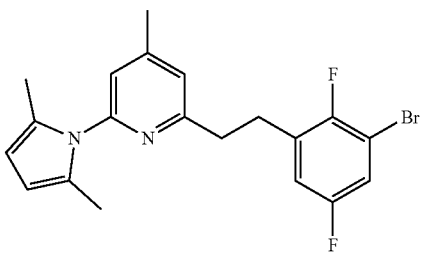 [SMILES: Cc1cc(CCc2cc(F)cc(Br)c2F)nc(-n2c(C)ccc2C)c1]

2-(3-bromo-2,5-difluorophenethyl)-6-(2,5-dimethyl-1H-pyrrol-1-yl)-4-methylpyridine (37c). Compound 37c was synthesized according to general procedure SB using 22 (1 g, 5 mmol) and 36c (1.57 g, 5.5 mmol). 37c was isolated as a light-yellow oil (1.27 g, 63%) after flash column chromatography 5% ethyl acetate/hexanes. $^1$H NMR (500 MHz, CDCl$_3$) δ 7.10 (ddd, J=3.1, 5.1, 7.8 Hz, 1H), 6.89 (s, 1H), 6.86 (s, 1H), 6.79 (ddd, J=3.1, 5.3, 8.5 Hz, 1H), 5.88 (s, 2H), 3.15-3.01 (m, 4H), 2.36 (s, 3H), 2.10 (s, 6H). $^{13}$C NMR (126 MHz, CDCl$_3$) δ 159.7, 157.9 (dd, J$_{C-F}$=2.8, 246.1 Hz), 154.0 (dd, J$_{C-F}$=3.1, 241.7 Hz), 151.8, 149.7, 131.1 (dd, J$_{C-F}$=8.0, 19.4 Hz), 128.5, 122.6, 120.4, 118.0 (d, J$_{C-F}$=26.4 Hz), 116.3 (dd, J$_{C-F}$=4.3, 23.4 Hz), 109.0 (dd, J$_{C-F}$=10.7, 24.6 Hz), 106.8, 37.5, 29.3, 21.0, 13.2.

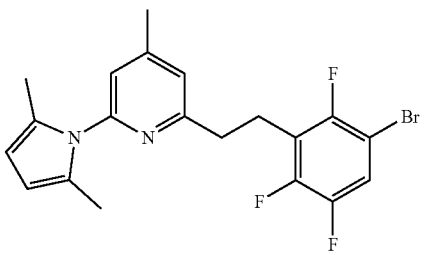 [SMILES: Cc1cc(CCc2c(F)c(F)cc(Br)c2F)nc(-n2c(C)ccc2C)c1]

2-(3-bromo-2,5,6-trifluorophenethyl)-6-(2,5-dimethyl-1H-pyrrol-1-yl)-4-methylpyridine (37d). Compound 37d was synthesized according to general procedure SB using 22 (1.06 g, 5.3 mmol) and 36d (1.77 g, 5.82 mmol). 37d was isolated as a light-yellow oil (1.45 g, 65%) after flash column chromatography 5% ethyl acetate/hexanes. $^1$H NMR (500 MHz, CDCl$_3$) δ 7.30-7.20 (m, 1H), 6.92-6.85 (m, 2H), 5.88 (s, 2H), 3.21-3.00 (m, 4H), 2.37 (s, 3H), 2.11 (s, 6H). $^{13}$C NMR (126 MHz, CDCl$_3$) δ 159.5, 159.3, 154.7-152.4 (m), 151.8, 149.7, 149.6, 148.2 (ddd, J$_{C-F}$=249.2, 13.5, 7.4 Hz), 146.8 (ddd, J$_{C-F}$=249.2, 14.3, 3.9 Hz), 128.5, 122.4, 120.4, 118.3 (d, J$_{C-F}$=21.8 Hz), 102.6 (ddd, J$_{C-F}$=24.2, 7.7, 4.4 Hz), 37.0, 23.5, 21.0, 13.2.

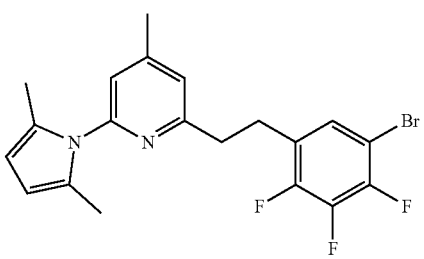 [SMILES: Cc1cc(CCc2cc(Br)c(F)c(F)c2F)nc(-n2c(C)ccc2C)c1]

2-(5-bromo-2,3,4-trifluorophenethyl)-6-(2,5-dimethyl-1H-pyrrol-1-yl)-4-methylpyridine (37e). Compound 37e was synthesized according to general procedure SB using 22 (1 g, 5 mmol) and 36e (1.67 g, 5.5 mmol). 37e was isolated as a light-yellow oil (1.19 g, 57%) after flash column chromatography 5% ethyl acetate/hexanes. $^1$H NMR (500 MHz, CDCl$_3$) δ 7.15 (ddd, J=9.3, 6.7, 2.5 Hz, 1H), 7.02 (dt, J=5.4, 2.1 Hz, 1H), 6.89 (s, 1H), 6.87 (s, 1H), 5.88 (s, 2H), 3.12-3.00 (m, 4H), 2.36 (s, 3H), 2.11 (s, 6H). $^{13}$C NMR (126 MHz, CDCl$_3$) δ 159.7, 151.8, 150.5 (dd, J$_{C-F}$=13.9, 243.2 Hz), 149.7, 148.4 (dd, J$_{C-F}$=10.1, 245.7 Hz), 128.5, 128.4 (t, J$_{C-F}$=3.5 Hz), 122.6, 120.5, 118.6, 118.5, 115.3 (dd, J$_{C-F}$=8.2, 4.4 Hz), 106.8, 37.6, 28.6, 21.0, 13.2. MS-ESI [M+H]$^+$=425.33.

General Procedure SC: Synthesis of alkynes 32a-c and 44a-c. Alkynes 32a-c and 44a-c are synthesized from their corresponding aldehydes following a previously reported protocol using Seyferth-Gilbert homologation.[1] In general, a dry round bottom flask was charged with p-toluenesulfonylazide (1.3 equiv.) and K$_2$CO$_3$ (4.5 equiv.). The mixture was dissolved in MeCN (0.1 M), followed by an addition of dimethyl-2-oxopropylphosphonate (1.2 mmol). The mixture was stirred for 2 h at RT, after which aldehyde (1.0 equiv.) dissolved in MeOH (0.1 M) was added dropwise. The reaction was then stirred for 15 h at RT. Upon completion, the reaction mixture was filtered through celite and solvents were removed under reduced pressure. The residue was partitioned in Et$_2$O and water, and the organic layer was washed with water, brine, and dried with anhydrous Na$_2$SO$_4$. The solvent was removed, and the crude mixture was purified by flash chromatography to provide alkyne 32a-c.

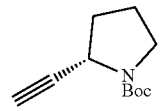

tert-Butyl (S)-2-ethynylpyrrolidine-1-carboxylate (32a). Compound 32a was synthesized according to general procedure SC from 30a (647 mg, 3.25 mmol). 32a (428 mg, 67%) was isolated with 10% ethyl acetate/hexane. $^1$H NMR (500 MHz, CDCl$_3$, mixture of rotamers) δ (4.49 (s)+4.33 (s), 1H), 3.47-3.28 (m, 2H), 2.16-2.01 (m, 1H), 1.88-1.64 (m, 4H), (1.42 (s)+1.38 (s), 9H). $^{13}$C NMR (126 MHz, CDCl$_3$, mixture of rotamers) δ 154.0, 84.4, 79.8, (69.8+69.4, 1C), (48.0+47.8, 1C), (45.9+45.5, 1C), (33.7+33.0, 1C), 28.5, (24.4+23.6, 1C).

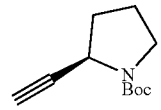

tert-Butyl (R)-2-ethynylpyrrolidine-1-carboxylate (32b). Compound 32b was synthesized according to general procedure SC from 30b (1 g, 5 mmol). 32b (821 mg, 84%) was isolated with 10% ethyl acetate/hexane. $^1$H NMR (500 MHz, CDCl$_3$, mixture of rotamers) δ (4.50 (s)+4.39 (s), 1H), 3.46-3.43 (m, 1H), 3.34-3.30 (m, 1H), 2.18 (brs, 1H), 2.04-1.99 (m, 3H), 1.87 brs, 1H) 1.45 (s, 9H). $^{13}$C NMR (126 MHz, CDCl$_3$, mixture of rotamers) δ 154.0, (84.4+84.1, 1C), 79.8, (69.8+69.4, 1C), (48.0+47.8, 1C), (45.9+45.5, 1C), (33.7+33.0, 1C), 28.5, (24.4+23.61C).

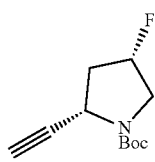

tert-Butyl (2S,4S)-2-ethynyl-4-fluoropyrrolidine-1-carboxylate (32c). Compound 32c was synthesized according to general procedure SC from 30c (1.57 g, 7.23 mmol). 32c (1 g, 67%) was isolated with 20% ethyl acetate/hexane. $^1$H NMR (500 MHz, CDCl$_3$) δ 5.27 (brs, 1H), 4.62 (brd, J=53.6 Hz, 1H), 3.79-3.73 (m, 1H), 3.58 (dd, J=35.5, 10.7 Hz, 1H), 2.42 (t, J=16.2 Hz, 1H) 2.29-2.22 (m, 2H), 1.46 (s, 9H). $^{13}$C NMR (126 MHz, CDCl$_3$, mixture of rotamers) δ 153.6, (93.0 (d, J$_{C-F}$=119.7 Hz)+91.5 (d, J$_{C-F}$=119.6 Hz), 1C), 83.2 (d, J$_{C-F}$=33.5 Hz), 80.5, 70.4 (d, J$_{C-F}$=45.7 Hz), 52.7, 46.5 (d, J$_{C-F}$=22.8 Hz), 39.4 (d, J$_{C-F}$=77.0 Hz), 28.4

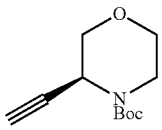

tert-Butyl (S)-3-ethynylmorpholine-4-carboxylate (44a). Compound 44a was synthesized according to general procedure SC from S1 (336 mg, 1.56 mmol). 44a (200 mg, 61%) was isolated with 20% ethyl acetate/hexane. $^1$H NMR (500 MHz, CDCl$_3$) δ 4.71 (s, 1H), 4.01-3.83 (m, 2H), 3.68 (d, J=13.0 Hz, 1H), 3.57 (dd, J=11.3, 3.2 Hz, 1H), 3.44 (td, J=11.8, 2.8 Hz, 1H), 3.29 (t, J=13.5 Hz, 1H), 2.28 (d, J=2.3 Hz, 1H), 1.46 (s, 9H). $^{13}$C NMR (126 MHz, CDCl$_3$) δ 154.4, 80.8, 80.4, 71.9, 69.9, 66.8, 44.4, 40.3, 28.3.

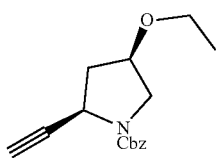 [SMILES: C#C[C@H]1C[C@@H](OCC)CN1C(=O)OCc1ccccc1]

Benzyl (2R,4R)-4-ethoxy-2-ethynylpyrrolidine-1-carboxylate (44b). Compound 44b was synthesized according to general procedure SC from S2 (480 mg, 1.73 mmol). 44b (220 mg, 45%) was isolated with 30% ethyl acetate/hexane. $^1$H NMR (500 MHz, CDCl$_3$) δ 7.32-7.13 (m, 5H), 5.15-4.94 (m, 2H), 4.56-4.44 (m, 1H), 3.96 (brs, 1H), 3.61-3.49 (m, 1H), 3.48-3.42 (m, 2H), 3.40-3.31 (m, 1H), 2.26-2.10 (m, 3H), 1.11 (t, J=7.0 Hz, 3H). $^{13}$C NMR (126 MHz, CDCl$_3$, mixture of rotamers) δ 154.4, (136.7+136.6, 1C), 128.4, 128.1, 127.9, 83.8, 83.4, 76.4, 70.5, 67.1, 64.4, (52.1+52.0, 1C), (46.9+46.5, 1C), (38.2+37.1, 1C), 15.2. MS-ESI [M+H]$^+$=274.28.

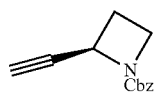

Benzyl (R)-2-ethynylazetidine-1-carboxylate (44c). Compound 44c was synthesized according to general procedure SC from S3 (926 mg, 4.23 mmol). 44c (500 mg, 55%) was isolated with 30% ethyl acetate/hexane. $^1$H NMR (500 MHz, CDCl$_3$) δ 7.28-7.16 (m, 5H), 5.01 (d, J=6.4 Hz, 2H), 4.70 (ddd, J=8.6, 5.9, 2.0 Hz, 1H), 3.92 (td, J=8.8, 5.8 Hz, 1H), 3.81 (td, J=8.7, 6.4 Hz, 1H), 2.49-2.41 (m, 1H), 2.43 (s, 1H), 2.25-2.17 (m, 1H). $^{13}$C NMR (126 MHz, CDCl$_3$) δ 156.0, 136.5, 128.4, 128.0, 127.9, 82.5, 73.8, 66.8, 50.3, 47.3, 24.1. MS-ESI [M+H]$^+$=216.04.

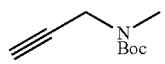

tert-Butyl-methyl(prop-2-ynyl)carbamate (25a). 25a was synthesized similarly to a previous report.[2] To a solution of N-methylpropargylamine (1 equiv.) in methanol was added slowly di-tert-butyl-dicarbonate (1.05 equiv.) at RT. The reaction was stirred at RT overnight. Upon completion, the reaction mixture was concentrated under reduced pressure to give 25a as a light-yellow oil (87%). $^1$H NMR (500 MHz, CDCl$_3$) δ 4.00 (brs, 2H), 2.86 (s, 3H), 2.17 (s, 1H), 1.42 (s, 9H). $^{13}$C NMR (125 MHz, CDCl$_3$) δ 155.2, 80.1, 79.2, 77.3, 71.6, 33.4, 28.3; MS ESI [M+H]$^+$=170.03.

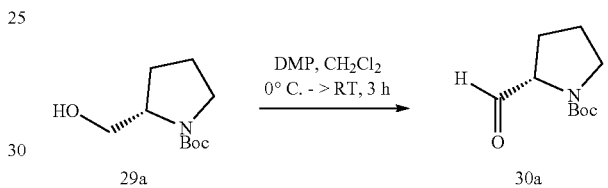

tert-Butyl (S)-2-formylpyrrolidine-1-carboxylate (30a). Aldehyde 30a were synthesized from a commercially available alcohol 29a using Dess-Martin periodinane (DMP) oxidation. A dry round bottom flask was charged with alcohol 29a (1 g, 4.97 mmol, 1 equiv.) and diluted with CH$_2$Cl$_2$ (0.3 M). At 0° C., DMP (2.3 g, 5.46 mmol, 1.1 equiv.) was added and the reaction was run at RT for 3 h. Upon completion, the reaction was diluted with CH$_2$Cl$_2$ and washed with saturated NaHCO$_3$ solution, brine and dried with Na$_2$SO$_4$. The organic layer was concentrated under reduced pressure and the crude mixture was purified by flash chromatography column with 30% ethyl acetate/hexane to yield 30a (0.84 g, 85%). $^1$H NMR (500 MHz, CDCl$_3$, mixture of rotamers) δ (9.52 (d, J=2.2 Hz)+9.43 (d, J=3.0 Hz), 1H), (4.17 (td, J=3.2, 6.1, 7.0 Hz)+4.01 (ddd, J=3.0, 6.3, 9.0 Hz), 1H), 3.47 (m, 2H), 2.16-1.76 (m, 4H), (1.44 (s)+1.39 (s), 9H).

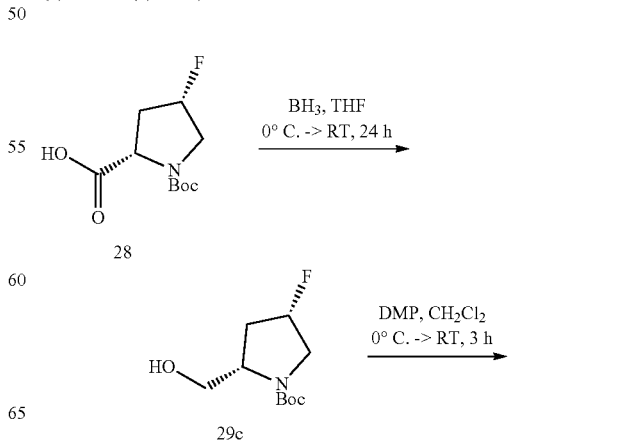

-continued

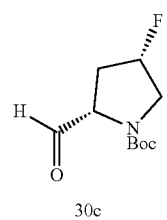

30c tert-Butyl (2S,4S)-4-fluoro-2-(hydroxymethyl)pyrrolidine-1-carboxylate (29c). In a dry round bottom flask was added 28 (2 g, 8.57 mmol, 1 equiv.) and diluted with THE (0.5 M). At 0° C., BH₃ 1M/THF (11 mL, 11 mmol, 1.3 equiv.) was added dropwise. The reaction was run at RT for 24 h before quenching with H₂O. The reaction mixture was extracted with ethyl acetate three times and the combined organic layer was washed with brine, dried with Na₂SO₄, and concentrated under reduced pressure. The crude product 29c (1.8 g, 97%) was carried to a next step without any purification.

tert-Butyl (2S,4S)-4-fluoro-2-formylpyrrolidine-1-carboxylate (30c). A dry round bottom flask was charged with alcohol 29c (1.8 g, 8.35 mmol, 1 equiv.) and diluted with CH₂Cl₂ (0.3 M). At 0° C., DMP (3.9 g, 9.2 mmol, 1.1 equiv.) was added and the reaction was run at RT for 3 h. Upon completion, the reaction was diluted with CH₂Cl₂ and washed with saturated NaHCO₃ solution, brine and dried with Na₂SO₄. The organic layer was concentrated under reduced pressure and the crude mixture was purified by flash chromatography column with 30% ethyl acetate/hexane to yield 30c (1.57 g, 87%). ¹H NMR (500 MHz, DMSO-d₆, mixture of rotamers) δ 9.50 (d, J=10.1 Hz, 1H), 5.31 (dt, J=3.2, 52.3 Hz, 1H), 4.26 (t, J=10.3 Hz, 1H), 3.71-3.47 (m, 2H), 2.47-2.18 (m, 2H), (1.44 (s)+1.38 (s), 9H). ¹³C NMR (126 MHz, DMSO-d₆, mixture of rotamers) δ (202.7+202.3, 1C), (154.4+153.6, 1C), (93.5 (d, $J_{C-F}$=121.9 Hz)+92.2 (d, $J_{C-F}$=121.7 Hz), 1C), 80.1, (63.9+63.7, 1C), (53.7 (d, $J_{C-F}$=22.1 Hz)+53.4 (d, $J_{C-F}$=22.0 Hz), 1C), (35.4 (d, $J_{C-F}$=20.8 Hz)+34.6 (d, $J_{C-F}$=20.4 Hz), 1C), (28.5+28.3, 1C).

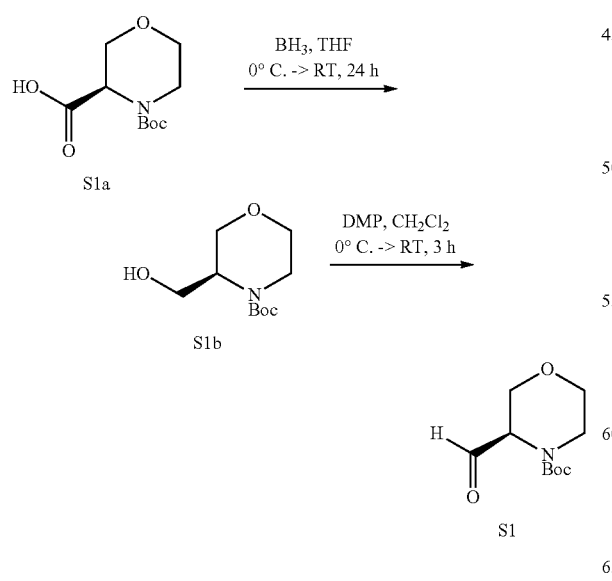

tert-Butyl (S)-3-(hydroxymethyl)morpholine-4-carboxylate (S1b). In a dry round bottom flask was added S1a (500 mg, 2.2 mmol, 1 equiv.) and diluted with THE (0.5 M). At 0° C., BH₃ 1M/THF (3 mL, 3 mmol, 1.3 equiv.) was added dropwise. The reaction was run at RT for 24 h before quenching with H₂O. The reaction mixture was extracted with ethyl acetate three times and the combined organic layer was washed with brine, dried with Na₂SO₄, and concentrated under reduced pressure. The crude product S1b (449 mg, 94%) was carried to a next step without any purification. ¹H NMR (500 MHz, CDCl₃) δ 3.98 (s, 1H), 3.90 (d, J=11.9 Hz, 1H), 3.87-3.77 (m, 3H), 3.74-3.69 (m, 1H), 3.54 (dd, J=11.8, 3.5 Hz, 1H), 3.44 (td, J=11.8, 3.1 Hz, 1H), 3.16 (t, J=13.4 Hz, 1H), 1.45 (s, 9H). ¹³C NMR (126 MHz, CDCl₃) δ 155.4, 80.5, 66.7, 66.4, 60.6, 52.1, 40.1, 28.4. MS-ESI [M+H]⁺=218.14.

tert-Butyl (R)-3-formylmorpholine-4-carboxylate (S1). A dry round bottom flask was charged with alcohol S1b (449 mg, 2 mmol, 1 equiv.) and diluted with CH₂Cl₂ (0.3 M). At 0° C., DMP (965 mg, 2.3 mmol, 1.1 equiv.) was added and the reaction was run at RT for 3 h. Upon completion, the reaction was diluted with CH₂Cl₂ and washed with saturated NaHCO₃ solution, brine and dried with Na₂SO₄. The organic layer was concentrated under reduced pressure and the crude mixture was purified by flash chromatography column with 30% ethyl acetate/hexane to yield S1 (336 mg, 75%). ¹H NMR (500 MHz, CDCl₃) δ 9.6 (s, 1H), 4.5-4.2 (m, 2H), 3.9-3.7 (m, 2H), 3.6 (dd, J=12.0, 4.2 Hz, 1H), 3.5 (dd, J=8.0, 4.2 Hz, 1H), 3.3-3.0 (m, 1H), 1.5 (s, 9H). ¹³C NMR (126 MHz, CDCl₃, mixture of rotamers) 6 (199.3+190.0, 1CH), (155.6+155.1, 1C), 81.03 (1C), (66.6+66.3, 1CH₂), (64.5+64.4, 1CH₂), (61.7+60.5, 1CH), (42.42+41.08, 1CH₂), 28.2

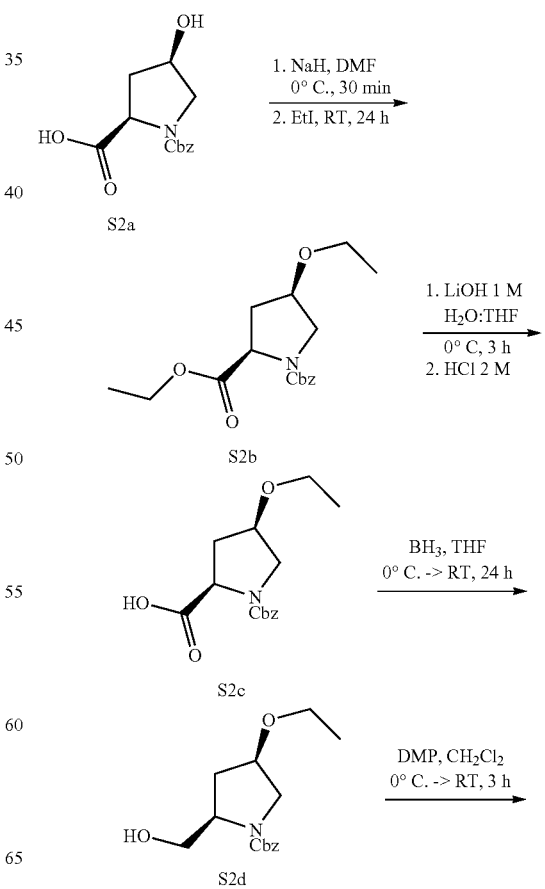

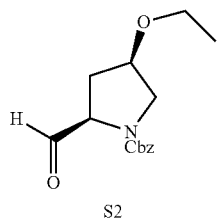

S2

1-Benzyl 2-ethyl (2R,4R)-4-ethoxypyrrolidine-1,2-dicarboxylate (S2b). In a dry bottom flask was added S2a (500 mg, 1.89 mmol, 1 equiv.) and diluted with DMF (0.25 M). At 0° C., NaH 60% in mineral oil (196 mg, 4.9 mmol, 2.6 equiv.) was added and the reaction was run at the same temperature for 30 min. After which, ethyl iodide (0.76 mL, 9.4 mmol, 5 equiv.) was added dropwise and the reaction was run at RT for 24 h before quenching with NH$_4$Cl. The reaction mixture was extracted with ethyl acetate and the combined organic layer was washed with brine, dried with Na$_2$SO$_4$, and concentrated under reduced pressure. The crude mixture was purified by flash chromatography column with 20% ethyl acetate/hexane to yield S2b (347 mg, 57%). $^1$H NMR (500 MHz, CDCl$_3$) δ 7.32-7.19 (m, 5H), 5.08 (s, 2H), 4.38 (dd, J=8.6, 3.7 Hz, 1H), 4.32 (dd, J=7.0, 5.3 Hz, 1H), 4.14-4.07 (m, 2H), 4.00 (q, J=7.1 Hz, 2H), 3.46 (ddd, J=14.9, 11.6, 2.9 Hz, 2H), 2.23-2.19 (m, 2H), 1.17 (t, J=7.2 Hz, 3H), 1.05 (t, J=7.0 Hz, 3H). MS-ESI [M+H]$^+$=322.47.

(2R,4R)-1-((benzyloxy)carbonyl)-4-ethoxypyrrolidine-2-carboxylic acid (S2c). A round bottom flask was charged with S2b (2.2 g, 7.18 mmol, 1 equiv.) and diluted with THF (0.25 M). At 0° C., LiOH 1 M (11 mL, 11 mmol, 1.5 equiv.) was added dropwise. The reaction was run at 0° C. for 3 h. Upon completion, THF was removed under vacuum and the reaction mixture was acidified with HCl 2 M until pH=1. The reaction mixture was extracted with ethyl acetate and the combined organic layer was washed with brine, dried with Na$_2$SO$_4$, and concentrated under reduced pressure. The crude product S2c (1.7 g, 80%) was carried to a next step without any purification. MS-ESI [M+H]$^+$=294.34.

Benzyl (2R,4R)-4-ethoxy-2-(hydroxymethyl)pyrrolidine-1-carboxylate (S2d). In a dry round bottom flask was added S2c (1.7 g, 5.8 mmol, 1 equiv.) and diluted with THF (0.5 M). At 0° C., BH$_3$ 1M/THF (8 mL, 8 mmol, 1.4 equiv.) was added dropwise. The reaction was run at RT for 24 h before quenching with H$_2$O. The reaction mixture was extracted with ethyl acetate and the combined organic layer was washed with brine, dried with Na$_2$SO$_4$, and concentrated under reduced pressure. The crude product S2d (1.26 g, 79%) was carried to a next step without any purification. $^1$H NMR (500 MHz, CDCl$_3$) δ 7.29-7.18 (m, 5H), 5.02 (d, J=6.0 Hz, 2H), 4.12-4.06 (m, 1H), 3.96-3.84 (m, 1H), 3.70-3.63 (m, 1H), 3.48 (dd, J=11.9, 5.1 Hz, 2H), 3.41 (d, J=10.6 Hz, 1H), 3.38-3.33 (m, 1H), 2.17-2.05 (m, 1H), 1.84-1.69 (m, 1H), 1.07 (t, J=7.2 Hz, 3H). $^{13}$C NMR (126 MHz, CDCl$_3$) δ 156.5, 136.4, 128.5, 128.1, 128.0, 76.8, 67.3, 66.4, 64.6, 59.6, 52.6, 34.4, 15.2. MS-ESI [M+H]$^+$=280.30.

Benzyl (2R,4R)-4-ethoxy-2-formylpyrrolidine-1-carboxylate (S2). A dry round bottom flask was charged with S2d (1.2 g, 4.5 mmol, 1 equiv.) and diluted with CH$_2$Cl$_2$ (0.3 M). At 0° C., DMP (2.1 g, 5 mmol, 1.1 equiv.) was added and the reaction was run at RT for 3 h. Upon completion, the reaction was diluted with CH$_2$Cl$_2$ and washed with saturated NaHCO$_3$ solution, brine and dried with Na$_2$SO$_4$. The organic layer was concentrated under reduced pressure and the crude product S2 (0.96 g, 77%) was carried to a next step without any purification. MS-ESI [M+H]$^+$=278.26.

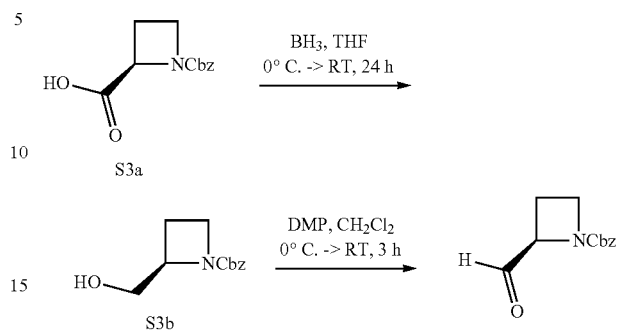

Benzyl (2R,4R)-4-ethoxy-2-(hydroxymethyl)pyrrolidine-1-carboxylate (S3b). In a dry round bottom flask was added S3a (2 g, 8.5 mmol, 1 equiv.) and diluted with THF (0.5 M). At 0° C., BH$_3$ 1M/THF (12 mL, 12 mmol, 1.4 equiv.) was added dropwise. The reaction was run at RT for 24 h before quenching with H$_2$O. The reaction mixture was extracted with ethyl acetate and the combined organic layer was washed with brine, dried with Na$_2$SO$_4$, and concentrated under reduced pressure. The crude product S3b (1.2 g, 64%) was carried to a next step without any purification. MS-ESI [M+H]$^+$=222.15.

Benzyl (2R,4R)-4-ethoxy-2-formylpyrrolidine-1-carboxylate (S3). A dry round bottom flask was charged with S3b (1.3 g, 5.8 mmol, 1 equiv.) and diluted with CH$_2$Cl$_2$ (0.3 M). At 0° C., DMP (2.7 g, 6.4 mmol, 1.1 equiv.) was added and the reaction was run at RT for 3 h. Upon completion, the reaction was diluted with CH$_2$Cl$_2$ and washed with saturated NaHCO$_3$ solution, brine and dried with Na$_2$SO$_4$. The organic layer was concentrated under reduced pressure and the crude mixture was purified by flash chromatography column with 40% ethyl acetate/hexane to yield S3 (0.92 g, 72%). $^1$H NMR (500 MHz, CDCl$_3$) δ 9.71 (s, 1H), 7.20-7.13 (m, 5H), 5.01 (d, J=6.5 Hz, 2H), 4.67-4.56 (m, 1H), 3.86-3.61 (m, 2H), 2.45-2.34 (m, 1H), 2.24-2.15 (m, 1H). MS-ESI [M+H]$^+$=220.04

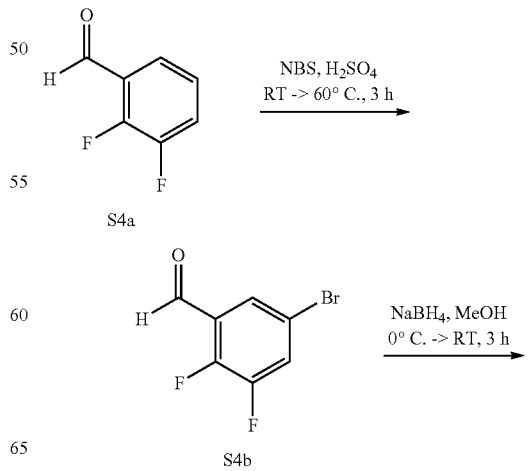

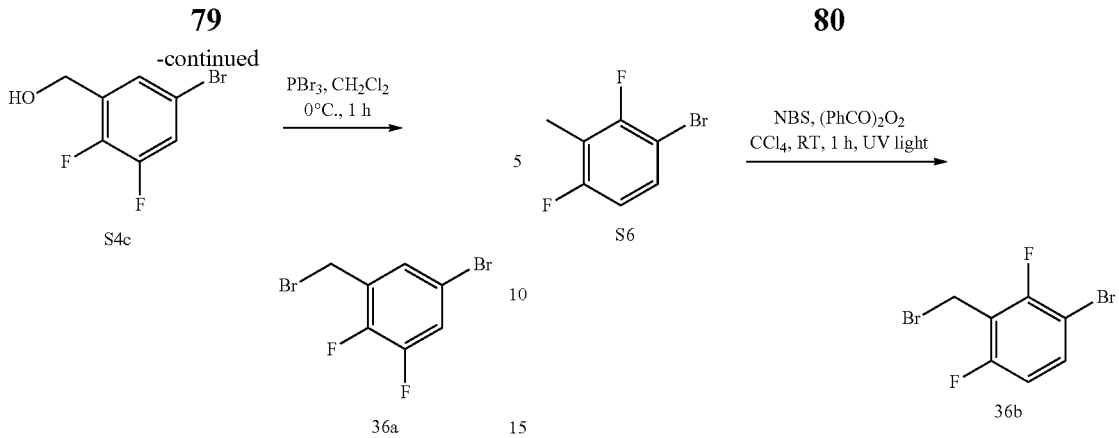

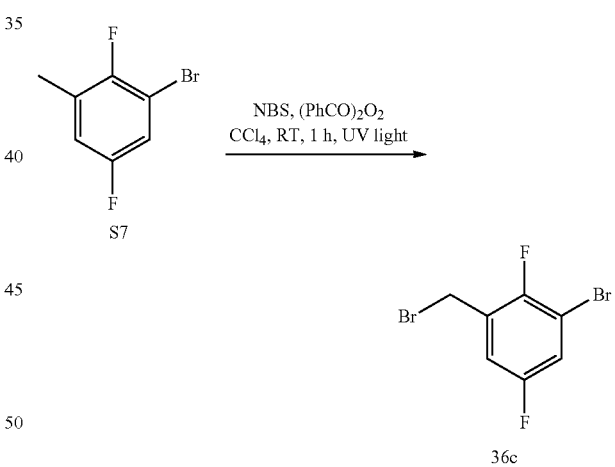

5-bromo-2,3-difluorobenzaldehyde (S4b). In a round bottom flask was added S4a (1.4 g, 10 mmol, 1 equiv.) and diluted with 5 mL $H_2SO_4$. NBS (2.1 g, 12 mmol, 1.2 equiv.) was added in three portions in 30 min and the reaction was run at 60° C. for 3 h. Upon completion, the reaction mixture was poured into ice water and the mixture was extracted with $Et_2O$. The combined organic layer was washed with brine, dried with $Na_2SO_4$, and concentrated under reduced pressure. The crude mixture was purified by flash chromatography column with 5% ethyl acetate/hexane to yield S4b (1.2 g, 44%). $^1$H NMR (500 MHz, $CDCl_3$) δ 10.30-10.20 (m, 1H), 7.80-7.70 (m, 1H), 7.60 (ddt, J=9.0, 7.1, 2.1 Hz, 1H). $^{13}$C NMR (126 MHz, $CDCl_3$) δ 184.4 (dd, $J_{C-F}$=6.3, 3.1 Hz), 151.9 (dd, $J_{C-F}$=261.7, 13.2 Hz), 150.6 (dd, $J_{C-F}$=256.7, 13.0 Hz), 126.6 (d, $J_{C-F}$=6.5 Hz), 126.3 (d, $J_{C-F}$=2.9 Hz), 126.2 (d, $J_{C-F}$=12.9 Hz), 125.8 (d, $J_{C-F}$=20.5 Hz).

(5-bromo-2,3-difluorophenyl)methanol (S4c). In a dry round bottom flask was added S4b (1.1 g, 5 mmol, 1 equiv.) and diluted with MeOH (0.2 M). At 0° C., $NaBH_4$ (265 mg, 7 mmol, 1.4 equiv.) was added. The reaction was run at RT for 3 h before quenching with $H_2O$. The reaction mixture was extracted with ethyl acetate and the combined organic layer was washed with brine, dried with $Na_2SO_4$, and concentrated under reduced pressure. The crude mixture was purified by flash chromatography column with 20% ethyl acetate/hexane to yield S4c (1 g, 81%). $^1$H NMR (500 MHz, $CDCl_3$) δ 7.35 (dt, J=2.2, 5.1 Hz, 1H), 7.24 (ddd, J=2.4, 7.1, 9.3 Hz, 1H), 4.73 (s, 2H), 2.15 (s, 1H). $^{13}$C NMR (126 MHz, $CDCl_3$) δ 150.1 (dd, $J_{C-F}$=13.6, 253.1 Hz), 147.4 (dd, $J_{C-F}$=12.9, 248.6 Hz), 131.7 (d, $J_{C-F}$=12.5 Hz), 126.5 (t, $J_{C-F}$=3.3 Hz), 119.8 (d, $J_{C-F}$=20.1 Hz), 115.9 (dd, $J_{C-F}$=4.4, 8.0 Hz), 58.3 (t, $J_{C-F}$=3.6 Hz).

5-bromo-1-(bromomethyl)-2,3-difluorobenzene (36a). In a dry round bottom flask was added S4c (1 g, 4.5 mmol, 1 equiv.) and diluted with $CH_2Cl_2$ (0.2 M). At 0° C., $PBr_3$ 1M/$CH_2Cl_2$ (5.4 mL, 5.4 mmol, 1.2 equiv.) was added dropwise. The reaction was run at 0° C. for 1 h before quenching with saturated $NaHCO_3$ solution. The reaction mixture was extracted with ethyl acetate and the combined organic layer was washed with brine, dried with $Na_2SO_4$, and concentrated under reduced pressure. The crude mixture was purified by flash chromatography column with 5% ethyl acetate/hexane to yield 36a (0.7 g, 60%). $^1$H NMR (500 MHz, $CDCl_3$) δ 7.29-7.19 (m, 2H), 4.37 (s, 2H). $^{13}$C NMR (126 MHz, $CDCl_3$) δ 150.4 (dd, $J_{C-F}$=13.5, 254.2 Hz), 148.0 (dd, $J_{C-F}$=13.1, 252.6 Hz), 129.0 (d, $J_{C-F}$=12.4 Hz), 128.8 (d, $J_{C-F}$=3.5 Hz), 121.0 (d, $J_{C-F}$=20.3 Hz), 115.8 (dd, $J_{C-F}$=4.8, 8.1 Hz), 23.4 (t, $J_{C-F}$=3.7 Hz).

1-bromo-3-(bromomethyl)-2,4-difluorobenzene (36b). In a dry round bottom flask was added S6 (2 g, 9.7 mmol, 1 equiv.), NBS (2 g, 12 mmol, 1.2 equiv.) and $(PhCO)_2O_2$ (75 mg, 0.3 mmol, 0.03 equiv.). The mixture was diluted with $CCl_4$ (0.125 M) and irradiated with mercury lamp at RT for 1 h. Upon completion, the reaction was filtered through a pack of celite and the filtrate was diluted with $CH_2Cl_2$ and washed with water, brine and concentrated under reduced pressure. The crude mixture was purified by flash chromatography column with 100% hexane to yield 36b (2.34 g, 85%). $^1$H NMR (500 MHz, $CDCl_3$) δ 7.48 (td, J=5.9, 8.3 Hz, 1H), 6.83 (td, J=1.8, 8.8 Hz, 1H), 4.50 (s, 2H). $^{13}$C NMR (126 MHz, $CDCl_3$) δ 160.0 (dd, $J_{C-F}$=5.8, 252.8 Hz), 157.3 (dd, $J_{C-F}$=7.2, 252.2 Hz), 133.5 (dd, $J_{C-F}$=1.8, 9.9 Hz), 116.1 (t, $J_{C-F}$=19.5 Hz), 112.7 (dd, $J_{C-F}$=4.1, 22.7 Hz), 104.2 (dd, $J_{C-F}$=4.1, 21.4 Hz), 17.5 (t, $J_{C-F}$=4.4 Hz).

1-bromo-3-(bromomethyl)-2,5-difluorobenzene (36c). In a dry round bottom flask was added S7 (3.4 g, 16.4 mmol, 1 equiv.), NBS (3.2 g, 18 mmol, 1.1 equiv.) and $(PhCO)_2O_2$ (120 mg, 0.5 mmol, 0.03 equiv.). The mixture was diluted with $CCl_4$ (0.125 M) and irradiated with mercury lamp at RT for 1 h. Upon completion, the reaction was filtered through a pack of celite and the filtrate was diluted with $CH_2Cl_2$ and washed with water, brine and concentrated under reduced pressure. The crude mixture was purified by flash chromatography column with 100% hexane to yield 36c (1.64 g, 35%). $^1$H NMR (500 MHz, $CDCl_3$) δ 7.24 (ddd, J=3.1, 5.4, 7.6 Hz, 1H), 7.07 (ddd, J=3.1, 5.3, 8.2 Hz, 1H), 4.43 (s, 2H). $^{13}$C NMR (126 MHz, $CDCl_3$) δ 159.0-156.4 (m), 153.5 (dd, $J_{C-F}$=2.7, 245.8 Hz), 127.5 (dd, $J_{C-F}$=8.4, 17.8 Hz), 120.7 (d, $J_{C-F}$=26.4 Hz), 116.8 (dd, $J_{C-F}$=2.5, 24.1 Hz), 109.8 (dd, $J_{C-F}$=10.4, 23.8 Hz), 24.4 (d, $J_{C-F}$=3.8 Hz).

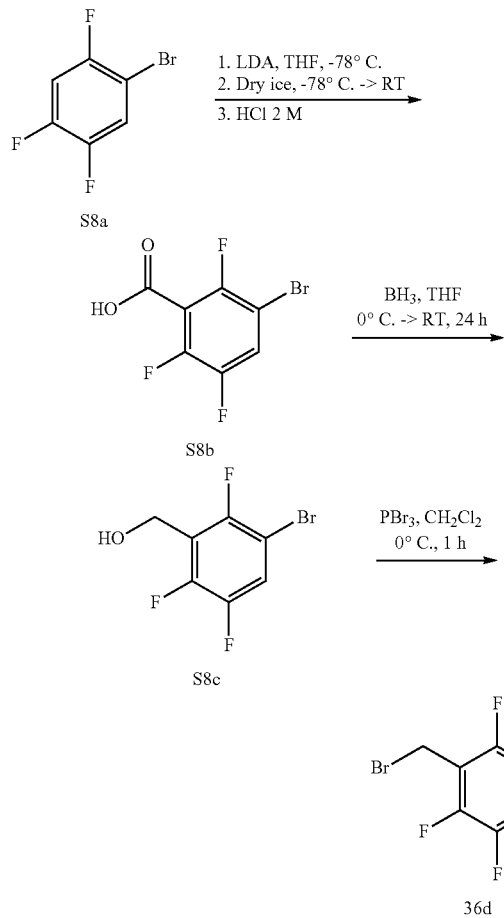

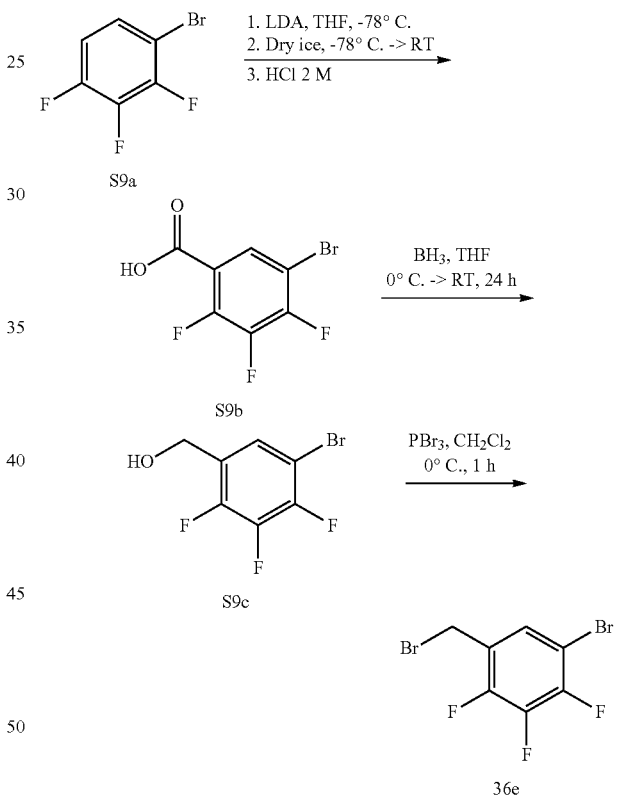

3-bromo-2,5,6-trifluorobenzoic acid (S8b). Making LDA: in a flame dry round bottom flask was added n-BuLi 1.6 M/THF (1.4 mL, 2.2 mmol, 1.1 equiv.) and diluted with 2 mL THF. At −78° C., DIPA (0.34 mL, 2.4 mmol, 1.2 equiv.) was added and the reaction was run at 0° C. for 15 min.

In another dry round bottom flask, S8a (422 mg, 2 mmol, 1 equiv.) was added and diluted with 4 mL THF (0.5 M). At −78° C., freshly made LDA was added dropwise via a cannula to S8a and the reaction was stirred at the same temperature for 10 min. Dry ice in Et$_2$O was then added and the reaction was let warm up to RT and run for 30 min before quenching with HCl 1 M. The reaction mixture was extracted with ethyl acetate and the combined organic layer was washed with brine, dried with Na$_2$SO$_4$, and concentrated under reduced pressure. The crude product (453 mg, 88%) was carried to a next step without any purification. $^1$H NMR (500 MHz, CDCl$_3$) δ 8.45 (s, broad, 1H), 7.59 (td, J=6.2, 8.4 Hz, 1H).

(3-bromo-2,5,6-trifluorophenyl)methanol (S8c). In a dry round bottom flask was added S8b (450 mg, 1.76 mmol, 1 equiv.) and diluted with THF (0.5 M). At 0° C., BH$_3$ 1M/THF (2.5 mL, 2.5 mmol, 1.4 equiv.) was added dropwise. The reaction was run at RT for 24 h before quenching with H$_2$O. The reaction mixture was extracted with ethyl acetate three times and the combined organic layer was washed with brine, dried with Na$_2$SO$_4$, and concentrated under reduced pressure. The crude product S8c (327 mg, 77%) was carried to a next step without any purification. $^1$H NMR (500 MHz, CDCl$_3$) δ 7.46-7.29 (m, 1H), 4.79 (s, 2H), 2.29 (s, 1H).

1-bromo-3-(bromomethyl)-2,4,5-trifluorobenzene (36d). In a dry round bottom flask was added S8c (241 mg, 1 mmol, 1 equiv.) and diluted with CH$_2$Cl$_2$ (0.2 M). At 0° C., PBr$_3$ 1M/CH$_2$Cl$_2$ (1.2 mL, 1.2 mmol, 1.2 equiv.) was added dropwise. The reaction was run at 0° C. for 1 h before quenching with saturated NaHCO$_3$ solution. The reaction mixture was extracted with ethyl acetate and the combined organic layer was washed with brine, dried with Na$_2$SO$_4$, and concentrated under reduced pressure. The crude mixture was purified by flash chromatography column with 100% hexane to yield 36d (273 mg, 90%). $^1$H NMR (500 MHz, CDCl$_3$) δ 7.25 (td, J=6.4, 8.6 Hz, 1H), 4.36 (t, J=1.5 Hz, 2H). $^{13}$C NMR (126 MHz, CDCl$_3$) δ 153.1 (dt, $J_{C-F}$=4.1, 248.8 Hz), 147.9 (ddd, $J_{C-F}$=6.3, 13.9, 255.8 Hz), 146.8 (ddd, $J_{C-F}$=5.0, 13.9, 250.7 Hz), 120.9 (d, $J_{C-F}$=21.5 Hz), 117.4 (dd, $J_{C-F}$=15.9, 21.3 Hz), 103.2 (ddd, $J_{C-F}$=4.8, 7.9, 23.8 Hz), 16.9 (t, $J_{C-F}$=3.3 Hz).

3-bromo-2,5,6-trifluorobenzoic acid (S9b). Making LDA: in a flame dry round bottom flask was added n-BuLi 1.6 M/THF (1.6 mL, 2.6 mmol, 1.1 equiv.) and diluted with 2.6 mL THF. At −78° C., DIPA (0.4 mL, 2.9 mmol, 1.2 equiv.) was added and the reaction was run at 0° C. for 15 min.

In another dry round bottom flask, S8a (500 mg, 2.4 mmol, 1 equiv.) was added and diluted with 4.8 mL THF (0.5 M). At −78° C., freshly made LDA was added dropwise via a cannula to S8a and the reaction was stirred at the same temperature for 10 min. Dry ice in Et$_2$O was then added and the reaction was let warm up to RT and run for 30 min before quenching with HCl 1 M. The reaction mixture was extracted with ethyl acetate and the combined organic layer was washed with brine, dried with $Na_2SO_4$, and concentrated under reduced pressure. The crude product (410 mg, 67%) was carried to a next step without any purification. $^1$H NMR (500 MHz, $CDCl_3$) δ 8.66 (broad, s, 2H), 8.05 (td, J=6.9, 2.4 Hz, 1H). $^{13}$C NMR (126 MHz, $CDCl_3$) δ 166.8 (t, $J_{C-F}$=3.3 Hz), 152.3 (ddd, $J_{C-F}$=258.9, 11.4, 3.1 Hz), 151.4 (ddd, $J_{C-F}$=268.2, 11.3, 2.8 Hz), 141.1 (dt, $J_{C-F}$=257.5, 15.9 Hz), 129.8 (d, $J_{C-F}$=3.9 Hz), 115.6 (dd, $J_{C-F}$=7.4, 4.0 Hz), 104.9 (dd, $J_{C-F}$=18.6, 4.6 Hz).

(3-bromo-2,5,6-trifluorophenyl)methanol (S9c). In a dry round bottom flask was added S9b (3.6 g, 14.12 mmol, 1 equiv.) and diluted with THF (0.5 M). At 0° C., $BH_3$ 1M/THF (19.8 mL, 19.8 mmol, 1.4 equiv.) was added dropwise. The reaction was run at RT for 24 h before quenching with $H_2O$. The reaction mixture was extracted with ethyl acetate three times and the combined organic layer was washed with brine, dried with $Na_2SO_4$, and concentrated under reduced pressure. The crude mixture was purified by flash chromatography column with 20% ethyl acetate/hexane to give S9c (3.16 g, 93%). $^1$H NMR (500 MHz, $CDCl_3$) δ 7.24 (td, J=6.9, 2.5 Hz, 1H), 4.56 (s, 2H), 3.70 (s, 1H). $^{13}$C NMR (126 MHz, $CDCl_3$) δ 148.2 (dt, $J_{C-F}$=250.2, 3.4 Hz), 148.1 (ddd, $J_{C-F}$=250.1, 5.0, 3.4 Hz), 140.2 (dt, $J_{C-F}$=255.7, 16.1 Hz), 129.7 (d, $J_{C-F}$=3.8 Hz), 125.8 (dd, $J_{C-F}$=12.8, 4.1 Hz), 125.6 (t, $J_{C-F}$=4.0 Hz), 104.5 (dd, $J_{C-F}$=18.1, 4.3 Hz), 58.0 (t, $J_{C-F}$=3.0 Hz).

1-bromo-3-(bromomethyl)-2,4,5-trifluorobenzene (36e). In a dry round bottom flask was added S9c (3.16 g, 13 mmol, 1 equiv.) and diluted with $CH_2Cl_2$ (0.2 M). At 0° C., $PBr_3$ 1M/$CH_2Cl_2$ (6.6 mL, 6.6 mmol, 0.5 equiv.) was added dropwise. The reaction was run at 0° C. for 1 h before quenching with saturated $NaHCO_3$ solution. The reaction mixture was extracted with ethyl acetate and the combined organic layer was washed with brine, dried with $Na_2SO_4$, and concentrated under reduced pressure. The crude mixture was purified by flash chromatography column with 100% hexane to yield 36e (1.68 g, 42%). $^1$H NMR (500 MHz, $CDCl_3$) δ 7.38 (td, J=6.9, 2.6 Hz, 1H), 4.42 (s, 2H). $^{13}$C NMR (126 MHz, $CDCl_3$) δ 148.9 (dd, $J_{C-F}$=2.5, 252.0 Hz), 148.8 (dd, $J_{C-F}$=2.5, 252.0 Hz), 140.5 (dt, $J_{C-F}$=256.7, 16.0 Hz), 127.8 (t, $J_{C-F}$=3.2 Hz), 123.6 (dd, $J_{C-F}$=12.7, 4.2 Hz), 104.7 (dd, $J_{C-F}$=18.4, 4.6 Hz), 23.2 (t, $J_{C-F}$=3.1 Hz).

NOS Enzyme Inhibition Assay. The NOS inhibitory activity of 2-21 was measured by the hemoglobin (Hb) NO capture assay following a protocol described previously.[24,29] Briefly, the assay was done in 100 mM HEPES buffer with 10% glycerol (pH 7.4) at 37° C. in the presence of 10 μM L-Arg, 10 μM $H_4B$, 100 μM NADPH, 0.83 mM $CaCl_2$), 320 units/mL of calmodulin, and 3 μM human oxyhemoglobin. The concentration of L-Arg, 10 μM, was used as it is sufficient not to cause NOS uncoupling and is close to the $K_m$ values of all three NOS isoforms where competitive inhibitors can be detected effectively. The assay was performed in 96-well plates using a Biotek Gen5™ microplate reader. NO production was kinetically monitored at 410 nm for 6 min. Rat nNOS,[30] human nNOS,[31] murine macrophage iNOS,[32] human iNOS[33] and human eNOS[34] are expressed in *E. coli* and purified as previously reported. The inhibition constants ($K_i$) for all NOSs were calculated from the $IC_{50}$ values of the dose-response curves using the Cheng-Prusoff equation: $K_i$=$IC_{50}$/(1+[S]/Km)[35] and $K_m$ (human nNOS: 1.6 μM; rat nNOS: 1.3 μM; murine iNOS: 8.2 μM; bovine eNOS: 1.7 μM; human eNOS: 3.9 μM; human iNOS: 8.0 μM).[36,37] Dose-response curves were constructed from seven to nine test concentrations (200 μM-50 nM), and $IC_{50}$ values were calculated by nonlinear regression using GraphPad Prism software. The calculated standard deviations from dose-response curves of the assays were less than 10% with all NOSs.

PAMPA-BBB Assay. The PAMPA-BBB assay was performed following a protocol described previously.[24] Briefly, the assay was done in 10 mM PBS buffer (pH=7.5) and compounds were tested at a concentration of 200 μM. The donor plate was first coated with 4 μL of porcine brain lipid (20 mg/mL in dodecane), followed by an addition of 250 μL of a test compound. The acceptor plate was filled with 250 μL of PBS and the donor plate was carefully placed on top of the acceptor plate to make a "sandwich". The plate was incubated at 25° C. for 17 h in a saturated humidity atmosphere with an orbital agitation at 100 rpm. Verapamil and theophylline were used as a positive and negative control, respectively. After incubation, 150 μL of test solution was taken from each well from both sides (donor and acceptor) and transferred to the UV plate for measurement. The effective permeability ($P_e$) was calculated using the following equation[38]:

$$P_e = \frac{2.303}{A \cdot (t - \tau_{ss})} \cdot \frac{V_A \cdot V_D}{(V_A + V_D)} \cdot lg\left[1 - \left(\frac{V_A + V_D}{(1-R) \cdot V_D}\right) \cdot \left(\frac{C_A(t)}{C_D(0)}\right)\right],$$

where $P_e$ is the effective permeability (cm/s), VA and VD are the volume of the acceptor and donor well (0.25 cm$^3$), respectively, $C_A$ (t) is the concentration of the acceptor well at time t, $C_D$ (0), CD (t) is the concentration of the donor well at to and t, respectively, A is the filter well area (0.21 cm$^2$). t is the incubation time (s). $\tau_{SS}$ is the time to reach a steady state (usually very short compared to the incubation time). R is the retention membrane factor and was calculated using the following equation:

$$R = \left[1 - \frac{C_D(t)}{C_D(0)} - \frac{V_A}{V_D} \cdot \frac{C_A(t)}{C_D(0)}\right].$$

$P_e$ was reported as an average of triplicate with a standard deviation.

Caco-2 Assay. The bidirectional Caco-2 assay was performed by Sai Life Sciences, Pune, India or Chempartner, Shanghai, China. Briefly, the assay was done in Hank's Balanced Salt Solution (HBSS) buffer (pH=7.4) in 90 min at 37° C. Compounds were tested at a concentration of 5 μM (0.1% DMSO). Studied compounds were applied to either the apical (A→B direction) or the basal side (B→A direction). The apparent permeability ($P_{app}$) was calculated using the following equation: $P_{app}$=(dQ/dt)/$C_0$.A, where dQ/dt is the change of test compound concentration in the receiver chamber over time, $C_0$ is the initial concentration of the compounds in the donor well, A is the filter well area (0.7 cm$^2$). The efflux ratio is defined by the ratio of the apparent permeability of B→A over that of A→B. An ER value above 3 indicates that a compound is possibly a substrate of P-gp or other active efflux transporters.

Inhibitor Complex Crystal Preparation. The sitting drop vapor diffusion method was used to grow crystals at 4° C. for the heme domains of rat nNOS (8 mg/mL containing 20 mM histidine), the human nNOS K301R/R354A/G357D mutant (10 mg/mL), and human eNOS (7 mg/mL). The crystal growth conditions were as described previously.[39] Fresh crystals were first passed stepwise through cryoprotectant solutions and then soaked with 5-10 mM inhibitor for 3-4 h at 4° C. before being flash cooled with liquid nitrogen and stored until data collection. The presence of an acetate ion near the heme active site in bovine eNOS caused interference in the binding mode of some inhibitors.[40] The high concentration of magnesium acetate in the heNOS growth conditions may also introduce an acetate near the active site that may influence the binding mode of inhibitors. To avoid having this acetate in the structure, the magnesium acetate in the cryoprotectant solution was replaced with $MgCl_2$.

X-ray Diffraction Data Collection, Data Processing, and Structural Refinement. The cryogenic (100 K) X-ray diffraction data were collected remotely at the Stanford Synchrotron Radiation Lightsource (SSRL) or Advanced Light Source (ALS) through the data collection control software Blu-Ice[41] and a crystal-mounting robot. When a CCD detector was used, 100-125° of data were typically collected with 0.50 per frame. If a Pilatus pixel array detector was used, 140-160° of fine-sliced data were collected with a 0.2° per frame. Raw CCD data frames were indexed, integrated, and scaled using iMOSFLM,[42] but the pixel array data were processed with XDS[43] and scaled with Aimless.[44] The binding of inhibitors was detected by initial difference Fourier maps calculated with REFMAC.[45] The inhibitor molecules were then modeled in Coot[46] and refined using REFMAC or PHENIX.[47] The crystal packing of the $MgCl_2$ soaked heNOS crystals was changed slightly, resulting in a symmetry change from the orthorhombic $P2_12_12_1$ reported previously[48] to monoclinic $P2_1$, with a R angle only 0.6-0.7° off compared to the original 90°. Therefore, a molecular replacement calculation with PHASER-MR[49] was needed to solve the structure. In the $P2_1$ space group, there are two heNOS dimers in the asymmetric unit. Disordering in portions of inhibitors bound in the NOS active sites was often observed, sometimes resulting in poor density quality. However, partial structural features were usually still visible if the contour level of the sigmaA weighted 2m|Fo|–D|Fc| map was dropped to 0.5 σ, which afforded the building of reasonable models into the disordered regions. Water molecules were added in PHENIX and checked by Coot. The TLS[50] protocol was implemented in the final stage of refinements with each subunit as one TLS group. The omit Fo-Fc density maps were calculated by removing inhibitor coordinates from the input PDB file before running one more round of TLS refinement in PHENIX (simulated annealing protocol with a 2000 K initial temperature). The resulting map coefficients DELFWT and PHDELWT were used to generate maps. For some recent structures, the Polder map facility in PHENIX was used to calculate the omit density map for the bound inhibitors.[51] The refined structures were validated in Coot before deposition in the Protein Data Bank.

REFERENCES

1. Müller, S.; Liepold, B.; Roth, G. J.; Bestmann, H. J. An Improved One-pot Procedure for the Synthesis of Alkynes from Aldehydes. *Synlett* 1996, 1996, 521-522.

2. Wang, H.-Y.; Qin, Y.; Li, H.; Roman, L. J.; Martisek, P.; Poulos, T. L.; Silverman, R. B. Potent and Selective Human Neuronal Nitric Oxide Synthase Inhibition by Optimization of the 2-Aminopyridine-Based Scaffold with a Pyridine Linker. *Journal of Medicinal Chemistry* 2016, 59, 4913-4925.

Example 3

In brain, nitric oxide (NO) produced by neuronal nitric oxide synthase (nNOS) participates in neuronal transmissions. The overproduction of NO by overactivated nNOS, however, is harmful and implicated in many neurodegenerative diseases including Parkinson's disease, Alzheimer's disease, amyotrophic lateral sclerosis, cerebral palsy, and ischemic stroke. Inhibition of nNOS, therefore, holds a promising therapeutic approach to develop a new drug for these diseases. In CNS drug development, effective delivery of therapeutic drugs into the human brain is one of the most challenging tasks because of the presence of the blood brain barrier (BBB), which excludes most potential molecules from entering the brain. In this work, we report our design and synthesis of novel human neuronal nitric oxide synthase (nNOS) inhibitors with a focus on enhancing their BBB penetration. We have developed several new analogs which not only exhibit excellent potency ($K_i$<30 nM) and high isoform selectivity in nNOS inhibition, but also display a significant improvement in brain penetration, indicated by high passive permeability in PAMPA-BBB assay and low efflux ratio in Caco-2 bidirectional assay.

Treatments for neurodegenerative diseases commonly known as Alzheimer's disease (AD), Parkinson's disease (PD) and amyotrophic lateral sclerosis (ALS) are still very limited. Current treatments only help to delay the symptoms. Additionally, the increase in the number of patients (more than 5 million people in America living with AD in 2017) as well as the immense cost of the treatment highlight the urgent medical need for these diseases. Inhibition of human nNOS holds a promise as a valuable therapeutic tool to treat these disorders. Human nNOS inhibitors presented in this invention not only display high potency and selectivity but also show an enhancement in brain penetration, indicating their high potential for further development into a novel therapeutic drug for neurodegeneration.

TABLE 4

Potency and selectivity of compounds on human NOSes and Caco-2 apparent permeability and efflux ratio (ER) of nNOS inhibitors.

| | | $K_i$ (nM) | | | | Selectivity nNOS | | Pe ($10^{-6}$ cm/s) |
|---|---|---|---|---|---|---|---|---|
| Compound | Structure | Rat nNOS | Human nNOS | iNOS | Human eNOS | n/i | human/rat | Human n/e | PAMPA-BBB |
| 47 | 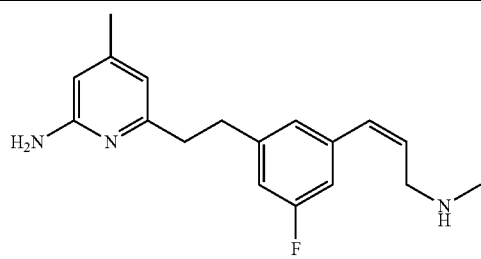 | 31 | 77 | 2278 | 24660 | 73 | 2.5 | 320 | 10.92 ± 0.02 |

TABLE 4-continued

Potency and selectivity of compounds on human NOSes and Caco-2 apparent permeability and efflux ratio (ER) of nNOS inhibitors.

| Compound | Structure | $K_i$ (nM) Rat nNOS | $K_i$ (nM) Human nNOS | $K_i$ (nM) iNOS | $K_i$ (nM) Human eNOS | Selectivity n/i | Selectivity nNOS human/rat | Selectivity Human n/e | $P_e$ ($10^{-6}$ cm/s) PAMPA-BBB |
|---|---|---|---|---|---|---|---|---|---|
| 48 | | 21 | 28 | 2725 | 20190 | 130 | 1.3 | 721 | 10.30 ± 0.02 |
| 49 | | 38 | 36 | 3760 | 22123 | 99 | 0.9 | 614 | No permeability |
| 50 | | 119 | 168 | 5782 | 26483 | 48 | 1.4 | 157 | 19.10 ± 0.5 |
| 51 | | 67 | 112 | 5876 | 29775 | 88 | 1.7 | 266 | 20 ± 0.85 |
| 52 | | 93 | 151 | 10022 | 27286 | 108 | 1.62 | 196 | 20.3 ± 0.16 |

TABLE 4-continued

Potency and selectivity of compounds on human NOSes and Caco-2 apparent permeability and efflux ratio (ER) of nNOS inhibitors.

| Compound | Structure | $K_i$ (nM) | | | | Selectivity nNOS | | | Pe ($10^{-6}$ cm/s) |
| --- | --- | --- | --- | --- | --- | --- | --- | --- | --- |
| | | Rat nNOS | Human nNOS | iNOS | Human eNOS | n/i | human/ rat | Human n/e | PAMPA-BBB |
| 53 | 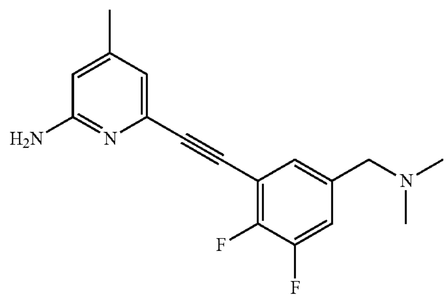 [SMILES: Cc1cc(N)nc(C#Cc2cc(CN(C)C)cc(F)c2F)c1] | 392 | ND | ND | ND | NA | NA | NA | ND |
| 54 | 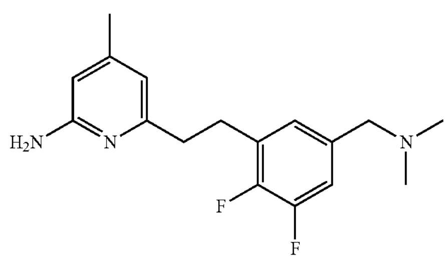 [SMILES: Cc1cc(N)nc(CCc2cc(CN(C)C)cc(F)c2F)c1] | 91 | ND | 76 | ND | NA | 0.8 | NA | ND |
| 55 | 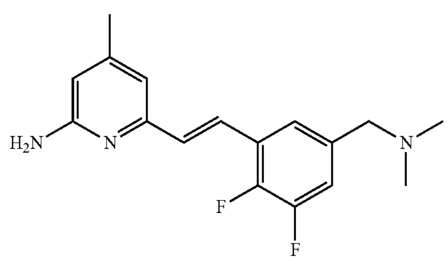 [SMILES: Cc1cc(N)nc(/C=C/c2cc(CN(C)C)cc(F)c2F)c1] | 129 | ND | ND | ND | NA | NA | NA | ND |
| 56 | 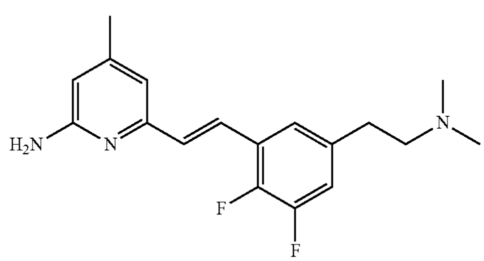 [SMILES: Cc1cc(N)nc(/C=C/c2cc(CCN(C)C)cc(F)c2F)c1] | 134 | ND | ND | ND | NA | NA | NA | ND |
| 57 | 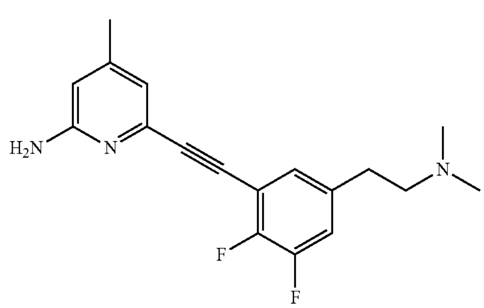 [SMILES: Cc1cc(N)nc(C#Cc2cc(CCN(C)C)cc(F)c2F)c1] | 293 | ND | ND | ND | NA | NA | NA | ND |

TABLE 4-continued

Potency and selectivity of compounds on human NOSes and Caco-2 apparent permeability and efflux ratio (ER) of nNOS inhibitors.

| Compound | Structure | $K_i$ (nM) | | | | Selectivity | | | $P_e$ ($10^{-6}$ cm/s) |
| --- | --- | --- | --- | --- | --- | --- | --- | --- | --- |
| | | Rat nNOS | Human nNOS | iNOS | Human eNOS | n/i | nNOS human/rat | Human n/e | PAMPA-BBB |
| 58 | (structure) | 23 | 24 | 1054 | 34719 | 46 | 1.0 | 1447 | 19.5 ± 1.4 |

The compounds of Table 4 were prepared using similar procedures as those outlined in Example 1 and Example 2. Similarly, the compounds were tested according to the procedure outlined in Exampled 1 and Example 2.

TABLE 5

Potency and selectivity of compounds on human NOSes and Caco-2 apparent permeability.

| Compound | Structure | $K_i$ (nM)$^{a,b}$ | | | | Selectivity | | | PAMBA-BBB $P_e$ ($10^{-6}$ $s^{-1}$)$^c$ |
| --- | --- | --- | --- | --- | --- | --- | --- | --- | --- |
| | | RnNOS | HnNOS | HiNOS | HeNOS | hn/rn | hn/hi | hn/he | |
| 58 | (structure, •2HCl) | 22 | 24 | 2181 | 14988 | 1.1 | 91 | 625 | 13.7 ± 0.6 |
| 59 | (structure, •2HCl) | 940 | 3163 | 21116 | ND | 3.4 | 6.7 | ND | 11.5 ± 0.5 |
| 60 | (structure, •2HCl) | 28 | 24 | 1751 | ND | 1.2 | 72 | ND | ND |

TABLE 5-continued
Potency and selectivity of compounds on human NOSes and Caco-2 apparent permeability.
| Compound | Structure | $K_i$ (nM)[a,b] | | | | Selectivity | | | PAMBA-BBB $P_e$ (10⁻⁶ c s⁻¹)[c] |
|---|---|---|---|---|---|---|---|---|---|
| | | RnNOS | HnNOS | HiNOS | HeNOS | hn/rn | hn/hi | hn/he | |
| 61 | 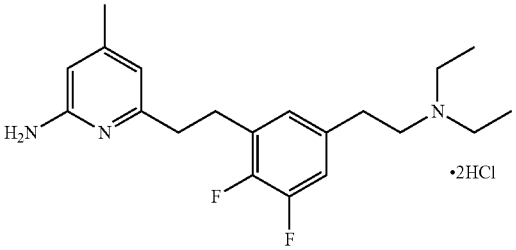 [SMILES: CCN(CC)CCc1cc(F)c(F)c(CCc2cc(C)cc(N)n2)c1] | 35 | 54 | 4212 | ND | 1.5 | 78 | ND | ND |
| 62 | 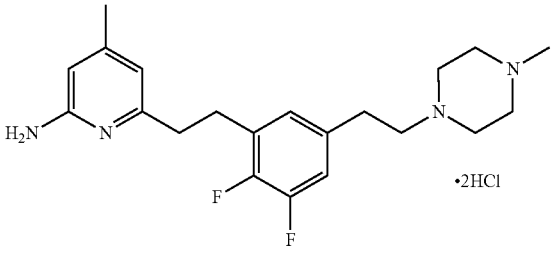 [SMILES: Cc1cc(N)nc(CCc2cc(CCN3CCN(C)CC3)cc(F)c2F)c1] | 83 | 88 | 10440 | ND | 1.0 | 119 | ND | ND |
| 63 | 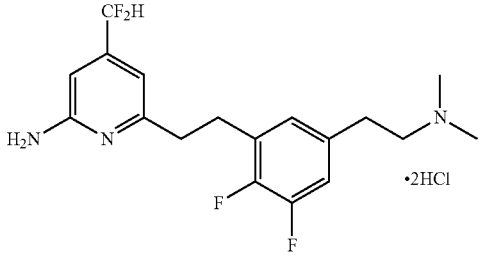 | 369 | 249 | 21476 | ND | 1.5 | 86 | 50 | 16.0 ± 1.5 |
| 64 | 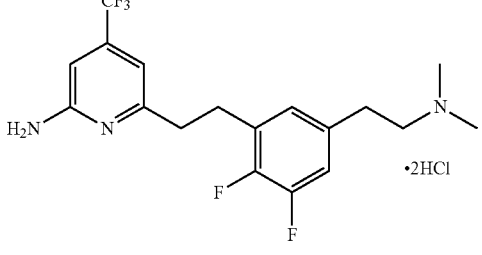 | 1313 | 2058 | 26316 | 101989 | 1.6 | 13 | 50 | 17.3 ± 0.5 |
| 65 | 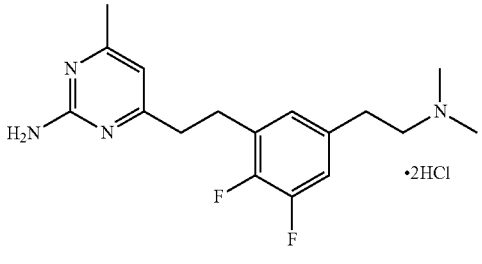 [SMILES: Cc1cc(CCc2cc(CCN(C)C)cc(F)c2F)nc(N)n1] | 6577 | 3833 | 39422 | ND | 1.7 | 10 | ND | 11.7 ± 1.83 |

TABLE 5-continued

Potency and selectivity of compounds on human NOSes and Caco-2 apparent permeability.

| Compound | Structure | $K_i$ (nM)[a,b] | | | | Selectivity | | | PAMBA-BBB $P_e$ (10$^{-6}$ c s$^{-1}$)[c] |
|---|---|---|---|---|---|---|---|---|---|
| | | RnNOS | HnNOS | HiNOS | HeNOS | hn/rn | hn/hi | hn/he | |
| 66 | [structure: 6-amino-4-methoxy-pyridine with ethylene linker to 3,4-difluorophenyl with CH2CH2N(Me)2, ·2HCl] | 75 | 55 | 4982 | ND | 1.4 | 91 | ND | 6.8 ± 0.67 |
| 67 | [structure: 6-amino-4-chloro-pyridine with alkyne linker to 3,4-difluorophenyl with CH2CH2N(Me)2, ·2HCl] | 1995 | 2417 | 65333 | ND | 1.2 | 27 | ND | 11.3 ± 0.49 |
| 68 | [structure: 6-amino-4-chloro-pyridine with O-CH2-(2,3-difluorophenyl), ·HCl] | 102000 | NT | NT | NT | NT | NT | NT | NT |
| 69 | [structure: 6-amino-4-methyl-pyridine with propyl-N(Me)2, ·2HCl] | 26 | 29 | 2831 | 537 | 1.1 | 98 | 19 | ND |
| 70 | [structure: 6-amino-4-methyl-pyridine with propyl-NHMe, ·2HCl] | 29 | 21 | 669 | ND | 1.4 | 32 | ND | ND |
| 71 | [structure: 6-amino-4-methyl-pyridine with propargyl-NHMe, ·2HCl] | 88 | 92 | 3575 | ND | 1.0 | 39 | ND | ND |

TABLE 5-continued

Potency and selectivity of compounds on human NOSes and Caco-2 apparent permeability.

| Compound | Structure | $K_i$ (nM)[a,b] | | | | Selectivity | | | PAMPA-BBB $P_e$ ($10^{-6}$ $s^{-1}$)[c] |
|---|---|---|---|---|---|---|---|---|---|
| | | RnNOS | HnNOS | HiNOS | HeNOS | hn/rn | hn/hi | hn/he | |
| 72 | 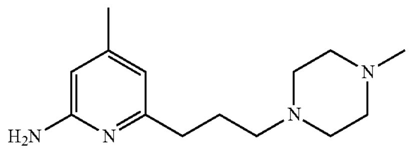 | 55 | 171 | 10160 | ND | 3.0 | 59 | ND | ND |
| 73 | 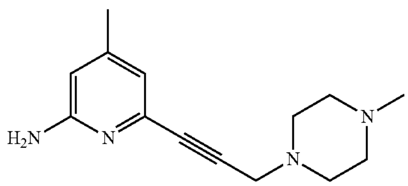 | 947 | 2124 | 113733 | ND | 2.2 | 54 | ND | ND |

[a]$K_i$ values were calculated from the IC50 values of a dose-response curve using the Cheng-Prusoff equation. 8 to 11 concentrations were tested, and the IC50 value was calculated from an average of at least two duplicates. The standard errors were less than 10%. The ratio hn/rn was determined to evaluate the potential translation of these inhibitors from preclinical data to a clinical study. This ratio was aimed to be as close to 1.0 as possible so that there would be little to no significant difference in the amount of inhibitors used in rat and human dosage.
[b]The plate reader syringes will be equilibrated with assay buffer (100 mM Hepes with 10% glycerol: pH = 7.4) before the assay.
[c]The Pe was obtained after 17 h incubation of compoundsat 25° C. with an orbital agitation at 100 rpm.
ND = Not determined.
NT = not tested.

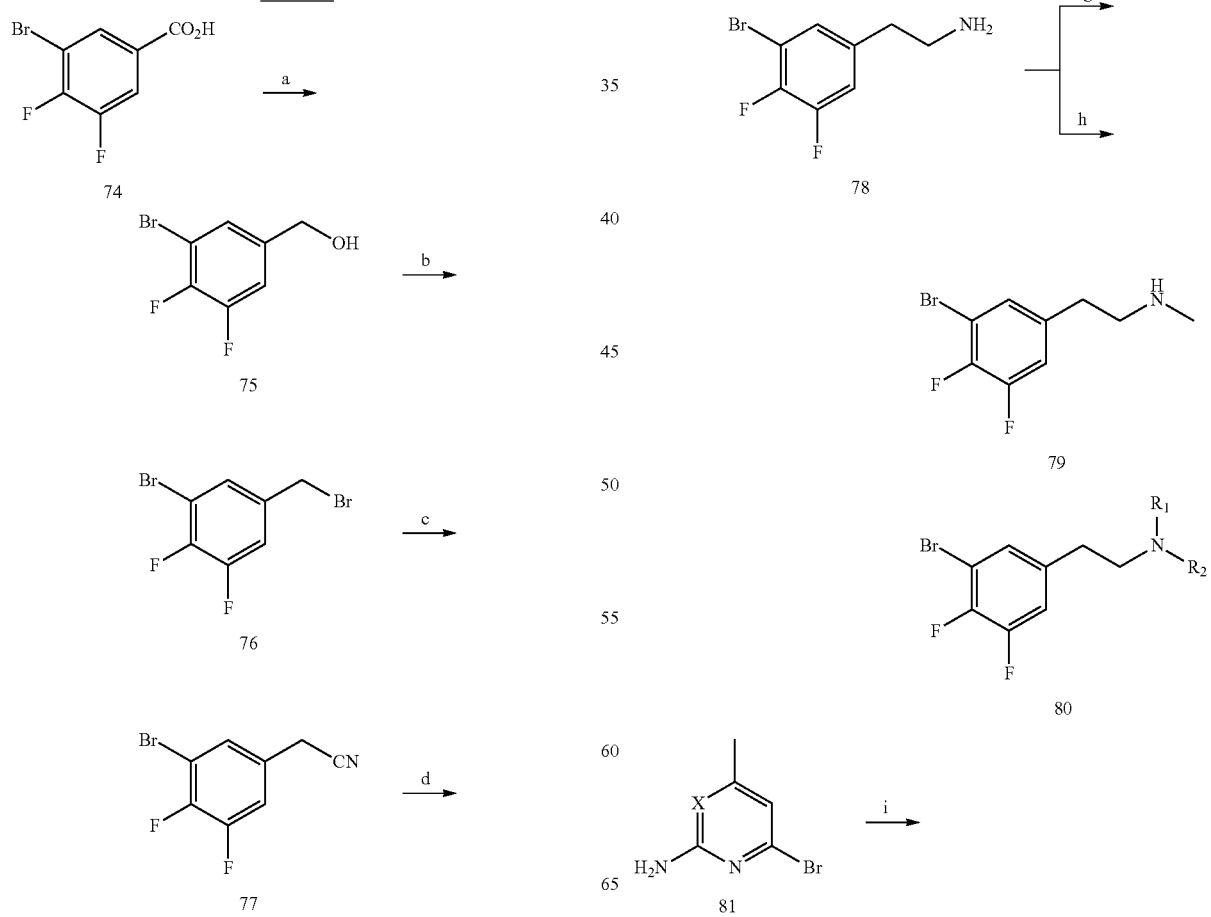

Scheme 7

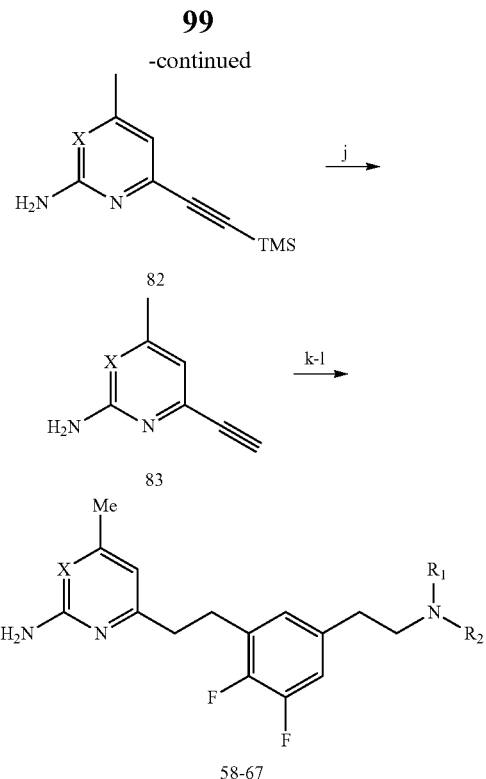

58-67

(a) BH₃·SMe₂, THF, 0° C. to rt, 24 h, 95%; (b) CBr₄, PPh₃, 0° C. to rt, 28 h, DCM, 89%; (c) KCN, (nBu)₄NBr, DCM:H₂O (1:1) (0.2M), 24 h, 91%; (d) BH₃·SMe₂, THF, 0° C. t rt, 30 h, 90%; (e) Boc₂O, Et₃N, DCM, rt, 22 h, 90%; (f) NaH, MeI, 0° C. to rt, 24 h, DMF, 69%; (g) TFA, 0° C. to rt, 24 h 88%; (h) Aldehyde or Ketone, NaBH₃CN, CH₃CO₂H, 80° C., 24 h, 70-80%; (i) Ethynyltrimethylsilane, Pd(PPh₃)₄, CuI, Et₃N, 120° C., CH₃CN (0.12M), 24 h, 30-80%; (j) K₂CO₃, MeOH, rt, 1 h, 80-90%; (k) 79-80, Pd(PPh₃)₄, CuI, Et₃N, 120° C., CH₃CN (0.12M), 24 h, 50-85%; (l) Pd/C, H₂, MeOH, rt, 24 h, 50-90%;

Synthesis of (3-bromo-4,5-difluorophenyl)methanol (75)

Compound 75 was prepared by following general procedure F. To a solution of 3-bromo-4,5-difluorobenzoic acid (74, 5.1 g, 21.52 mmol) in THF (150 mL) was added BH₃·SMe₂ (3.06 mL, 32.30 mmol) dropwise at 0° C. for 10 min under an argon atmosphere. After the addition, the resulting heterogeneous mixture was gradually warmed to 25° C. and stirred for 24 h. After completion, as indicated by TLC, the reaction mixture was poured slowly over saturated sodium bicarbonate and extracted with Et₂O (2×100 mL). The combined organic layers were washed with brine, dried over Na₂SO₄, filtered, and concentrated under reduced pressure. The crude product (75) was taken to the next step without further purification Synthesis of (1-bromo-5-(bromomethyl)-2,3-difluorobenzene (76)

Compound 76 was prepared by following general procedure F. A solution of alcohol 75 (4.56 g, 20.44 mmol) and carbon tetrabromide (7.46 g, 22.49 mmol) in DCM (50 mL) was prepared in a 200 mL round bottom flask and cooled to 0° C. Triphenylphosphine (5.90 g, 22.49 mmol) in DCM (50 mL) was added via dropping funnel over 30 min with vigorous stirring. After the addition of PPh₃ at 0° C., the reaction mixture was allowed to warm to 25° C. The colorless solution becomes a pale orange color and was stirred for an additional 28 h at room temperature. The reaction mixture was concentrated, and the resulting crude product was treated with excess hexane (500 mL). The white precipitate was filtered, and the remaining solution was concentrated and purified by flash column chromatography eluting with hexane: EtOAc (80:20 v:v) to afford compound 76 (5.20 g, 89%) as a yellow oil.

Synthesis of 2-(3-bromo-4,5-difluorophenyl)acetonitrile (77)

Compound 77 was prepared by following general procedure F. A 250 mL round bottom flask was charged with 76 (5.2 g, 18.19 mmol), potassium cyanide (1.244 g, 19.10 mmol), and tetrabutylammonium bromide (0.586 g, 1.819 mmol) under a nitrogen atmosphere. After addition of DCM and water in a 1:1 ratio (0.2 M), the biphasic system was allowed to stir vigorously for 24 h at room temperature. After this time, the organic phase was carefully separated from the aqueous phase and collected in a conical flask. The aqueous phase was extracted with DCM (2×50 mL). The combined organic layers were washed with brine, dried over Na₂SO₄, filtered, and concentrated under reduced pressure. The crude brown solid (77) was taken to the next step without further purification.

Synthesis of 2-(3-bromo-4,5-difluorophenyl)ethan-1-amine (78)

Compound 78 was prepared by following general procedure F. To a solution of 77 (3.84 g, 16.55 mmol) in THF (83 mL, 0.2M) was added BH₃·SMe₂ (4.71 mL, 49.65 mmol) dropwise at 0° C. for 10 mi under an argon atmosphere. After the addition, the resulting mixture was gradually warmed to 25° C. and stirred for 30 h. After completion of the reaction, as indicated by TLC, the reaction mixture was carefully quenched with MeOH (50 mL) and then 6M HCl (20 mL) at 0° C. and concentrated under reduced pressure. The crude ammonium salt was then dissolved in water (50 mL) and washed with EtOAc (2×50 mL). The aqueous layer was neutralized with 10% NaOH (pH 11), extracted with EtOAc (2×100 mL), dried over Na₂SO₄, filtered, and concentrated under reduced pressure. The crude product was further purified by flash column chromatography, eluting with hexane: EtOAc (50:50 v:v) then DCM:MeOH:Et₃N (70:20:10 v:v) to afford 78 (3.05 g, 78%) as a yellow oil.

Typical Procedure for Single Reductive Amination (79)

Compound 79 was prepared by following general procedure F. A mixture of 78 (0.5 g, 2.12 mmol), (Boc)₂O (0.51 g, 2.33 mmol) and Et₃N (0.59 mL, 4.24 mmol) in DCM (20 mL) was stirred for 22 h at room temperature under an argon atmosphere. The progress of the reaction was monitored by TLC. After completion of the reaction, the mixture was treated with water (50 mL) and extracted with DCM (3×50 mL). The combined organic layers were washed with brine, dried over Na₂SO₄, filtered, and concentrated under reduced pressure. The crude Boc protected amine (0.64 g, 1.91 mmol) was subjected to the next step without further purification. The mono Boc protected amine (0.64 g, 1.91 mmol) was dissolved in DMF (10 mL) and cooled to 0° C. NaH (92 mg, 2.30 mmol) was added to this under an argon atmosphere, and the resulting mixture was stirred for 1 h. The resulting suspension was treated with methyl iodide (0.14 mL, 2.30 mmol) and warmed gradually to 25° C., and stirring was continued for 24 h. After completion of the reaction, the mixture was diluted with water (100 mL) and extracted with Et₂O (3×20 mL). The combined organic layers were washed with brine, dried over Na₂SO₄, filtered, and concentrated under reduced pressure. The crude N-methyl-Boc-protected amine (0.46 g, 1.31 mmol) was taken to the next step without further purification. The crude N-methyl-Boc-protected amine (0.46 g, 1.31 mmol) was treated with excess trifluoroacetic acid (5 mL) at 0° C. and stirred for 8 h at 25° C. under an argon atmosphere. After completion of the reaction, as indicated by TLC, the reaction mixture was quenched slowly with 6 M NaOH at 0° C. and extracted with DCM (2×100 mL). The combined organic layers were washed with brine, dried over Na₂SO₄, filtered, and concentrated under reduced pressure. The crude product was further purified by flash column chromatography, eluting with hexane: EtOAc (50:50 v:v) then DCM:MeOH:Et₃N (70:20:10 v:v) to afford 79 (0.29 g, 88%) as a brown oil.

Typical Procedure for Double Reductive Amination (80)

Compound 80 was prepared by following general procedure F. To a stirred mixture of 2-(3-bromo-4,5-difluorophenyl)ethan-1-amine (78) (3.05 g, 12.92 mmol) and paraformaldehyde (3.88 g, 129.2 mmol) in CH₃CO₂H (162 mL, 0.08M) at 25° C. under an argon atmosphere, was added sodium cyanoborohydride (4.06 g, 64.6 mmol) all in one portion. The heterogeneous mixture was heated to 80° C., and stirring was continued for 24 h; during this time the heterogeneous mixture became a clear brown solution. After completion of the reaction, the mixture was concentrated under reduced pressure. The resulting thick oil was dissolved in DCM (100 mL), neutralized carefully with 2 M NaOH (pH 11). The organic fraction was separated from the aqueous phase. The aqueous phase was further extracted with DCM (2×100 mL). The combined organic layers were washed with brine, dried over Na₂SO₄, filtered, and concentrated under reduced pressure. The crude product was further purified by flash column chromatography, eluting with hexane: EtOAc (50:50 v:v) then DCM:MeOH:Et₃N (70:20:10 v:v) to afford 80 (2.70 g, 79%) as a brown oil.

Typical Procedure for Sonogashira Coupling Reaction (82)

Compound 82 was prepared by following general procedure F. A flame-dried pressure vessel containing 6-bromo-4-methylpyridin-2-amine (81) (7.0 g, 37.43 mmol), Pd(PPh₃)₄ (0.216 g, 0.187 mmol), and CuI (0.713 g, 3.74 mmol) was filled with argon by three vacuum-flush cycles to remove any traces of oxygen. To this were added CH₃CN (31 mL, 1.2 M), Et₃N (21 mL, 149.7 mmol), and ethynyltrimethylsilane (25.9 mL, 187.1 mmol), and the resulting mixture was stirred for 24 h at 120° C. After completion of the reaction, the reaction mixture was cooled to room temperature, filtered through Celite, and concentrated by rotary evaporation. Purification of the crude residue using flash column chromatography, eluting with hexane: EtOAc (50:50 v:v) then DCM:MeOH:Et₃N (70:20:10 v:v), furnished the desired product (82) as a brown oil (6.43 g, 84%).

Typical Procedure for Desilylation (83)

Compound 83 was prepared by following general procedure F. A 100 mL round bottom flask was charged with 82 (6.49 g, 31.77 mmol), and potassium carbonate (5.27 g, 38.12 mmol) under an argon atmosphere. After the addition of MeOH (20 mL, 1.6M), the heterogeneous mixture was allowed to stir for 1 h at room temperature. After completion of the reaction, the mixture was concentrated under reduced pressure. The crude solid was diluted with water and extracted with DCM (2×100 mL). The combined organic layers were washed with brine, dried over Na₂SO₄, filtered, and concentrated under reduced pressure. The crude product was purified by flash column chromatography, eluting with hexane: EtOAc (80:20 v:v) to afford 83 (3.73 g, 89%) as a brown solid.

Typical Procedure for Sonogashira Reaction and Hydrogenation (58-67)

Compounds 58-67 were prepared by following general procedure F. The Sonogashira reaction was performed following the same procedure as represented in the synthesis of 82. The purified Sonogashira coupled product was dissolved in MeOH, and hydrogenation was performed following the protocol in General Procedure C. The crude product was then purified by reverse-phase flash column chromatography eluting with H₂O: CH₃CN (95:5 v:v) to H₂O: CH₃CN (30:70 v:v) to afford final compounds 58-67.

General Procedure G

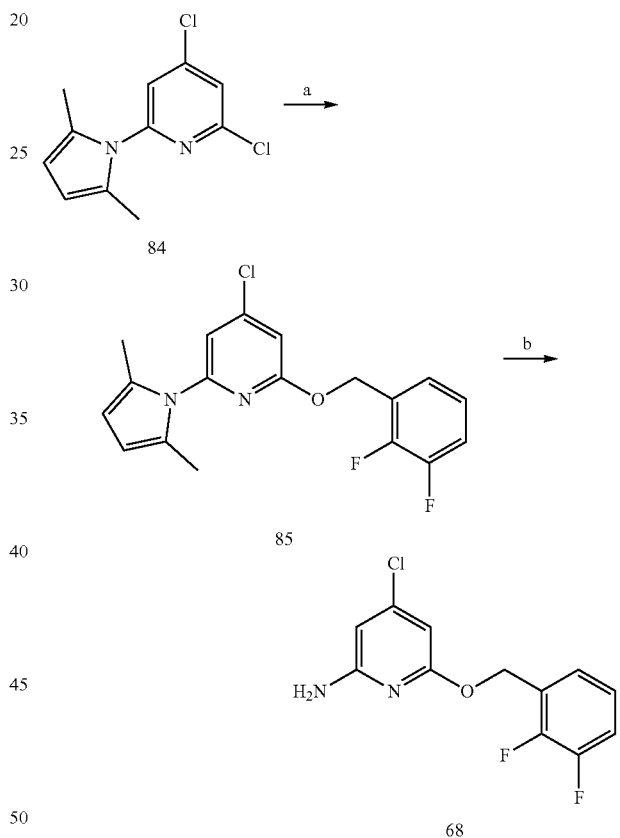

Scheme 8

(a) (2,3-difluorophenyl)methanol, K₂CO₃, 120° C., DMF (0.16M), 12 h, 62%; (b) NH₂OH, 100° C., EtOH:H₂O (2:1, 0.03M), 24 h, 73%.

Typical Procedure for S$_N$Ar Reaction and Pyrrole Deprotection (68)

Compound 68 was prepared by following General Procedure G. A flame-dried pressure vessel containing 84 (0.1 g, 0.415 mmol), (2,3-difluorophenyl)methanol (0.111 g, 0.498 mmol), and K₂CO₃ (0.287 g, 2.08 mmol), was filled with argon by three vacuum-flush cycles. To this was added DMF (3 mL, 0.16M), and the resulting mixture was stirred for 12 h at 120° C. After completion of the reaction, the reaction mixture was cooled to RT, diluted with excess water (50 mL), and extracted with Et₂O (2×100 mL). The combined organic layers were washed with brine, dried over Na₂SO₄, filtered, and concentrated under reduced pressure.

Crude product 85 was then taken to the next step without further purification. To a solution of protected amine 85 (0.127 g, 0.364 mmol) in EtOH (7.4 mL) was added hydroxylamine hydrochloride (0.127 g, 1.82 mmol) followed by H$_2$O (3.7 mL). The reaction mixture was heated at 100° C. for 24 h. After being cooled to room temperature, the solvent was evaporated under reduced pressure. The resulting brown oil was partitioned between Et$_2$O (20 mL) and water (20 mL). The aqueous layer was extracted with Et$_2$O (2×20 mL), and the combined organic layers were dried over Na$_2$SO$_4$. The solvent was removed by rotary evaporation, and the resulting brown oil was purified by flash column chromatography eluting with hexane: EtOAc (90:10 v:v) to hexane: EtOAc (50:50 v:v), furnishing the desired product (68) as a brown solid (72 mg, 73%)

General Procedure H

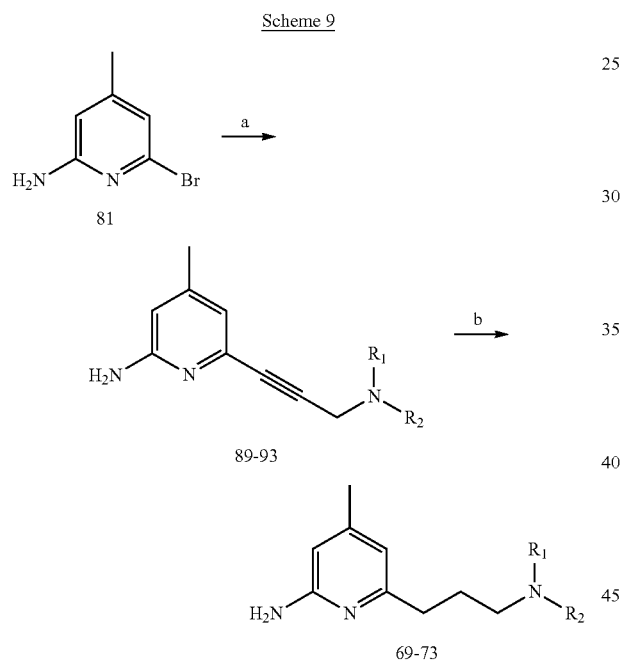

(a) 86-88, Pd(PPh$_3$)$_4$, CuI, Et$_3$N, 120° C., CH$_3$CN (0.1M), 24 h, 70-90%; (b) Pd/C or Pd(OH)$_2$/C, H$_2$, MeOH, 25-80° C., 8-24 h

Typical Procedure for Sonogashira Reaction and Hydrogenation (69-73)

Compounds 69-73 were prepared by following General Procedure H. The Sonogashira reaction was performed following the same procedure as represented in the synthesis of 82. The purified Sonogashira coupled product was dissolved in MeOH, and the hydrogenation was performed following the same protocol in General Procedure C. The crude product was then purified by reverse-phase flash column chromatography, eluting with H$_2$O:CH$_3$CN (95:5 v:v) to H$_2$O:CH$_3$CN (30:70 v:v) to afford final compounds 69-73.

Result and Discussion

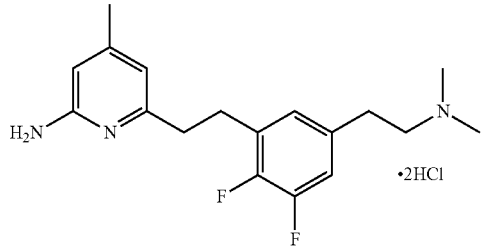

6-(5-(2-(Dimethylamino)ethyl)-2,3-difluorophenethyl)-4-methylpyridin-2-amine hydrochloride (58)

Compound 58 (Off-white solid, 89 mg, 0.279 mmol, 88%) was prepared from 81 according to General Procedure F. $^1$H NMR (500 MHz, CDCl$_3$): δ 6.94 (ddd, J=11.2, 7.3, 2.2 Hz, 1H), 6.77 (dt, J=6.0, 1.8 Hz, 1H), 6.25 (s, 1H), 6.23 (s, 1H), 2.99-2.95 (m, 2H), 2.80-2.77 (m, 2H), 2.71-2.67 (m, 2H), 2.50-2.46 (m, 2H), 2.29 (s, 6H), 2.14 (s, 3H). $^{13}$C NMR (126 MHz, CDCl$_3$): δ 160.7, 159.0, 151.5 (dd, J=245.7, 13.9 Hz), 151.0, 148.6 (dd, J=244.4, 12.6 Hz), 137.4 (dd, J=6.3, 3.8 Hz), 131.8 (d, J=13.9 Hz), 126.9 (t, J=3.8 Hz), 116.0 (d, J=17.6 Hz), 114.6, 108.1, 61.9, 45.3, 38.7, 33.7, 30.0 (t, J=1.9 Hz), 21.0. LRMS (ESI) Calcd for C$_{18}$H$_{24}$F$_2$N$_3$ [(M+H)$^+$]: 320.19, found: 320.49.

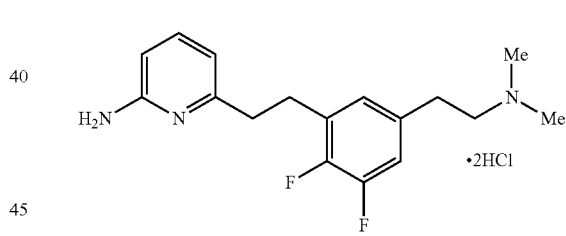

6-(5-(2-(Dimethylamino)ethyl)-2,3-difluorophenethyl)pyridin-2-amine hydrochloride (59)

Compound 59 (white solid, 188 mg, 0.616 mmol, 80%) was prepared from 2-amino-4,6-dichloropyridine according to General Procedure F. $^1$H NMR (500 MHz, CD$_3$OD): δ 7.82 (dd, J=8.9, 7.1 Hz, 1H), 7.18 (t, J=8.2 Hz, 2H), 6.89 (d, J=8.9 Hz, 1H), 6.69 (d, J=7.1 Hz, 1H), 3.44-3.36 (m, 2H), 3.18-3.02 (m, 6H), 2.96 (s, 6H). $^{13}$C NMR (126 MHz, CD$_3$OD): δ 156.3, 151.6 (dd, J$_{C-F}$=247.6, 13.4 Hz), 150.1, 149.2 (dd, J$_{C-F}$=245.6, 13.0 Hz), 145.7, 134.5 (dd, J$_{C-F}$=6.2, 4.5 Hz), 130.4 (d, J$_{C-F}$=12.7 Hz), 127.4 (d, J$_{C-F}$=3.3 Hz), 117.3 (d, J$_{C-F}$=17.9 Hz), 113.1, 112.2, 59.3, 43.7, 34.1, 30.9, 28.8. LRMS (ESI) Calcd for C$_{17}$H$_{22}$F$_2$N$_3$ [(M+H)$^+$]: 306.18, found: 305.90.

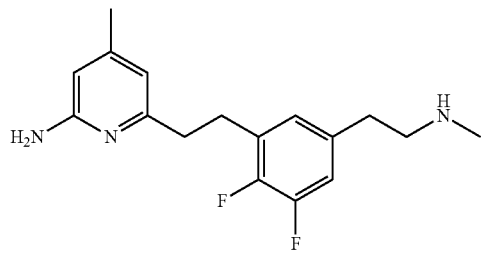

6-(2,3-Difluoro-5-(2-(methylamino)ethyl)phenethyl)-4-methylpyridin-2-amine (60)

Compound 60 (off-white solid, 86 mg, 0.282 mmol, 85%) was prepared from 81 according to General Procedure F. $^1$H NMR (500 MHz, CDCl$_3$): δ 6.83 (ddd, J=10.9, 7.2, 2.2 Hz, 1H), 6.74 (dt, J=6.1, 1.8 Hz, 1H), 6.30 (s, 1H), 6.17 (s, 1H), 4.39 (bs, 2H), 3.07-2.94 (m, 2H), 2.86-2.80 (m, 2H), 2.77 (t, J=6.9 Hz, 2H), 2.68 (t, J=6.9 Hz, 2H), 2.42 (s, 3H), 2.17 (s, 3H), 1.93 (bs, 1H). $^{13}$C NMR (126 MHz, CDCl$_3$): δ 157.9, 157.3, 149.4 (dd, J=248.2, 13.9 Hz), 148.3, 146.5 (dd, J=244.4, 12.6 Hz), 135.0 (dd, J=6.3, 3.8 Hz), 129.9 (d, J=12.6 Hz), 124.5 (d, J=3.8 Hz), 113.9 (d, J=17.6 Hz), 113.5, 105.7, 52.0, 37.1, 35.4, 34.5, 28.1, 20.0. LRMS (ESI) Calcd for C$_{17}$H$_{21}$F$_2$N$_3$ [(M+H)$^+$]: 306.18, found: 306.60.

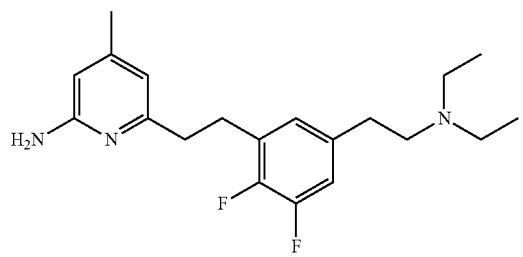

6-(5-(2-(Diethylamino)ethyl)-2,3-difluorophenethyl)-4-methylpyridin-2-amine (61)

Compound 61 (off-white solid, 83 mg, 0.239 mmol, 82%) was prepared from 81 according to General Procedure F. $^1$H NMR (500 MHz, CDCl$_3$): 6.82 (ddd, J=10.9, 7.2, 2.2 Hz, 1H), 6.72 (dt, J=6.0, 1.8 Hz, 1H), 6.30 (s, 1H), 6.16 (s, 1H), 4.38 (bs, 2H), 3.01-2.97 (m, 2H), 2.87-2.76 (m, 2H), 2.66-2.53 (m, 8H), 2.17 (s, 3H), 1.04 (t, J=7.2 Hz, 6H). $^{13}$C NMR (126 MHz, CDCl$_3$): δ 159.0, 158.4, 150.3 (dd, J=248.2, 13.9 Hz), 149.3, 147.4 (dd, J=244.4, 12.6 Hz), 136.7 (dd, J=6.3, 5.0 Hz), 130.8 (d, J=13.9 Hz), 125.5 (t, J=3.8 Hz), 115.0 (d, J=17.6 Hz), 114.6, 106.7, 54.7, 47.0, 38.3, 32.9, 29.2, 21.0, 11.9. LRMS (ESI) Calcd for C$_{20}$H$_{27}$F$_2$N$_3$ [(M+H)$^+$]: 348.46, found: 348.30.

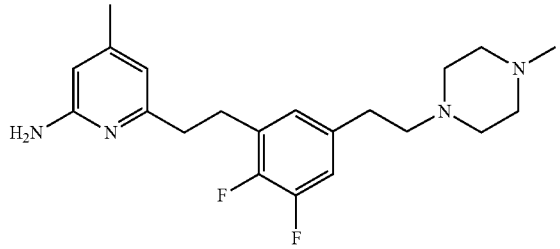

6-(2,3-Difluoro-5-(2-(4-methylpiperazin-1-yl)ethyl)phenethyl)-4-methylpyridin-2-amine (62)

Compound 62 (yellow solid, 166 mg, 0.443 mmol, 82%) was prepared from 81 according to General Procedure F. $^1$H NMR (500 MHz, CD$_3$OD): δ 6.93 (ddd, J=11.3, 7.3, 2.2 Hz, 1H), 6.75 (dt, J=6.0, 1.8 Hz, 1H), 6.24 (s, 1H), 6.22 (s, 1H), 2.99-2.94 (m, 2H), 2.80-2.76 (m, 2H), 2.71-2.67 (m, 2H), 2.67-2.30 (m, 10H), 2.29 (s, 3H), 2.14 (s, 3H). $^{13}$C NMR (126 MHz, CD$_3$OD): δ 160.8, 159.0, 151.4 (dd, J=245.7, 13.9 Hz), 151.0, 148.5 (dd, J=243.2, 12.6 Hz), 137.7 (dd, J=6.3, 3.8 Hz), 131.7 (d, J=12.6 Hz), 126.9 (t, J=3.8 Hz), 116.0 (d, J=16.4 Hz), 114.7, 108.1, 61.0, 55.6, 53.6, 46.0, 38.7, 33.2, 30.0, 21.0. LRMS (ESI) Calcd for C$_{21}$H$_{28}$F$_2$N$_4$ [(M+H)$^+$]: 375.24, found: 375.11.

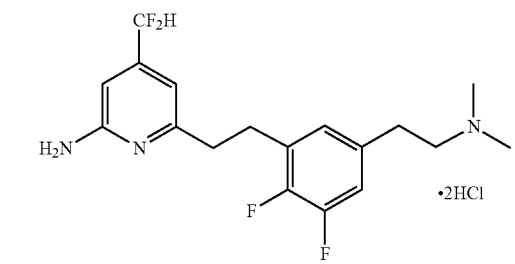

4-(Difluoromethyl)-6-(5-(2-(dimethylamino)ethyl)-2,3-difluorophenethyl)pyridin-2-amine hydrochloride (63)

Compound 63 (brown solid, 40 mg, 0.113 mmol, 85%) was prepared from 6-chloro-4-(difluoromethyl)pyridin-2-amine according to General Procedure F. $^1$H NMR (500 MHz, CDCl$_3$): δ 6.84 (ddd, J=10.8, 7.2, 2.2 Hz, 1H), 6.71 (dt, J=6.0, 1.8 Hz, 1H), 6.53 (s, 1H), 6.45 (t, J=56.0 Hz, 1H), 6.44 (s, 1H), 4.58 (s, 2H), 3.04-3.01 (m, 2H), 2.94-2.90 (m, 2H), 2.69-2.66 (m, 2H), 2.48-2.45 (m, 2H), 2.28 (s, 6H). $^{13}$C NMR (126 MHz, CDCl$_3$): δ 160.8, 158.6, 150.4 (dd, J$_{C-F}$=247.4, 13.3 Hz), 147.5 (dd, J$_{C-F}$=244.9, 12.7 Hz), 144.5 (t, J$_{C-F}$=22.8 Hz), 136.3 (t, J$_{C-F}$=5.0 Hz), 130.4 (d, J$_{C-F}$=12.7 Hz), 125.4 (t, J$_{C-F}$=3.2 Hz), 115.1 (d, J$_{C-F}$=17.1 Hz), 113.4 (t, J$_{C-F}$=240.9 Hz), 109.2 (t, J$_{C-F}$=5.6 Hz), 102.4 (t, J$_{C-F}$=6.5 Hz), 61.2, 45.5, 38.4, 33.6, 28.9 (t, J$_{C-F}$=2.3 Hz). LRMS (ESI) Calcd for C$_{18}$H$_{22}$F$_4$N$_3$ [(M+H)$^+$]: 356.17, found: 356.16.

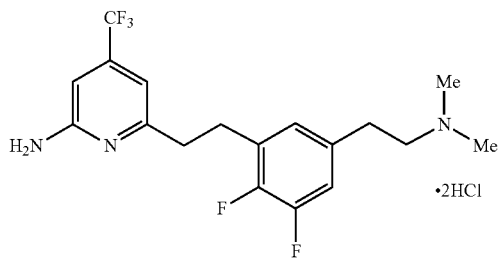

6-(5-(2-(Dimethylamino)ethyl)-2,3-difluorophen-ethyl)-4-(trifluoromethyl)pyridin-2-amine (64)

Compound 64 (off-white solid, 36 mg, 0.080 mmol, 30%) was prepared from 6-chloro-4-(trifluoromethyl)pyridin-2-amine according to General Procedure F. $^1$H NMR (500 MHz, CDCl$_3$): δ 6.96 (ddd, J=11.2, 7.2, 2.1 Hz, 1H), 6.79 (dt, J=6.2, 1.8 Hz, 1H), 6.61 (s, 1H), 6.49 (s, 1H), 3.06-2.99 (m, 2H), 2.92-2.89 (m, 2H), 2.74-2.71 (m, 2H), 2.59-2.56 (m, 2H), 2.37 (s, 6H). $^{13}$C NMR (126 MHz, CDCl$_3$): δ 161.9, 161.4, 151.5 (dd, $J_{C-F}$=247.0, 13.9 Hz), 148.7 (dd, $J_{C-F}$=243.2, 12.6 Hz), 141.3 (q, $J_{C-F}$=32.8 Hz), 137.1 (q, $J_{C-F}$=5.0 Hz), 131.5 (d, $J_{C-F}$=12.6 Hz), 126.9 (t, $J_{C-F}$=3.2 Hz), 124.6 (q, $J_{C-F}$=272.6 Hz), 116.2 (d, $J_{C-F}$=17.6 Hz), 107.6 (q, $J_{C-F}$=3.2 Hz), 103.2 (q, $J_{C-F}$=3.8 Hz), 61.6, 45.1, 38.9, 33.4, 29.6. LRMS (ESI) Calcd for C$_{18}$H$_{21}$F$_5$N$_3$ [(M+H)$^+$]: 374.1650, found: 374.69.

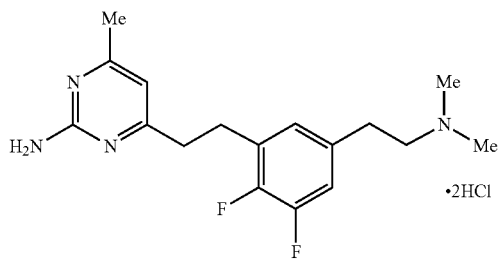

4-(5-(2-(Dimethylamino)ethyl)-2,3-difluorophen-ethyl)-6-methylpyrimidin-2-amine hydrochloride (65)

Compound 65 (pale yellow solid, 95 mg, 0.297 mmol, 80%) was prepared from 81' according to general procedure F. $^1$H NMR (500 MHz, CD$_3$OD): δ 7.16 (ddt, J=12.5, 5.4, 2.3 Hz, 2H), 6.84 (s, 1H), 3.42-3.34 (m, 2H), 3.18-3.11 (m, 2H), 3.11-3.01 (m, 4H), 2.95 (s, 6H), 2.49 (s, 3H). $^{13}$C NMR (126 MHz, CD$_3$OD): δ 157.5 (2×C), 151.7 (dd, $J_{C-F}$=247.5, 13.3 Hz), 149.2 (dd, $J_{C-F}$=245.7, 12.8 Hz), 134.4 (d, $J_{C-F}$=4.3 Hz), 134.3 (d, $J_{C-F}$=4.6 Hz), 131.1 (d, $J_{C-F}$=12.7 Hz), 127.3 (t, $J_{C-F}$=3.2 Hz), 117.1 (d, $J_{C-F}$=17.9 Hz), 111.0, 59.3, 43.6, 37.5, 30.9, 27.5, 20.9. LRMS (ESI) Calcd for C$_{17}$H$_{23}$F$_2$N$_4$ [(M+H)$^+$]: 321.19, found: 321.07.

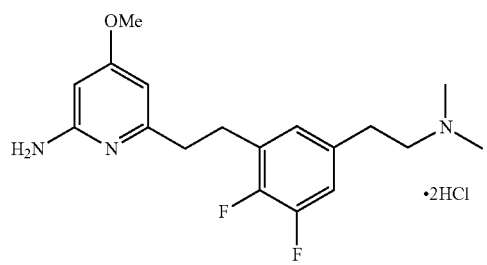

6-(5-(2-(Dimethylamino)ethyl)-2,3-difluorophen-ethyl)-4-methoxypyridin-2-amine hydrochloride (66)

Compound 66 (pale yellow solid, 62 mg, 0.185 mmol, 62%) was prepared from 6-chloro-4-methoxypyridin-2-amine according to General Procedure F. $^1$H NMR (500 MHz, CD$_3$OD): δ 7.19-7.15 (m, 2H), 6.33 (d, J=2.1 Hz, 1H), 6.26 (d, J=1.6 Hz, 1H), 3.92 (s, 3H), 3.42-3.35 (m, 2H), 3.12-2.99 (m, 6H), 2.95 (s, 6H). $^3$C NMR (126 MHz, CD$_3$OD): δ 172.6, 157.9, 151.6 (dd, $J_{C-F}$=247.7, 13.4 Hz), 151.3, 149.2 (dd, $J_{C-F}$=245.8, 13.0 Hz), 134.5 (dd, $J_{C-F}$=6.1, 4.4 Hz), 130.4 (d, $J_{C-F}$=12.6 Hz), 127.4, 117.3 (d, $J_{C-F}$=17.8 Hz), 105.1, 91.6, 59.4, 57.4, 43.7, 34.0, 30.9, 28.7. LRMS (ESI) Calcd for C$_{18}$H$_{24}$F$_2$N$_3$O [(M+H)$^+$]: 336.19, found: 336.29.

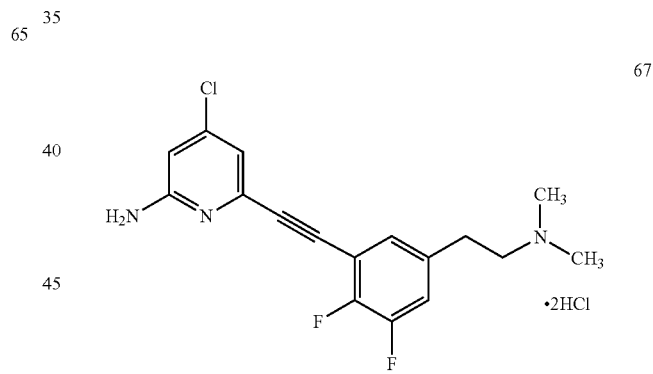

4-Chloro-6-((5-(2-(dimethylamino)ethyl)-2,3-difluo-rophenyl)ethynyl)pyridin-2-amine hydrochloride (67)

Compound 67 (brown solid, 142 mg, 0.423 mmol, 65%) was prepared from 2-amino-4,6-dichloropyridine according to General Procedure F. $^1$H NMR (500 MHz, CD$_3$OD): δ 7.32-7.23 (m, 2H), 6.87 (d, J=1.7 Hz, 1H), 6.63 (d, J=1.7 Hz, 1H), 2.82 (dd, J=9.3, 6.6 Hz, 2H), 2.67 (dd, J=9.4, 6.4 Hz, 2H), 2.37 (s, 6H). $^{11}$C NMR (126 MHz, CD$_3$OD): δ 161.9, 151.5 (dd, $J_{C-F}$=248.2, 12.6 Hz), 150.7 (dd, $J_{C-F}$=252.0, 13.9 Hz), 146.0, 142.2, 138.4 (dd, $J_{C-F}$=6.3, 5.0 Hz), 129.8 (d, $J_{C-F}$=3.8 Hz), 120.0 (d, $J_{C-F}$=17.6 Hz), 117.6, 113.6 (dd, $J_{C-F}$=11.3, 1.3 Hz), 109.9, 94.4 (d, $J_{C-F}$=3.8 Hz), 81.7 (d, $J_{C-F}$=3.8 Hz), 61.3, 45.2, 33.2. LRMS (ESI) Calcd for C$_{17}$H$_{16}$ClF$_2$N$_3$ [(M+H)$^+$]: 336.11, found: 336.28.

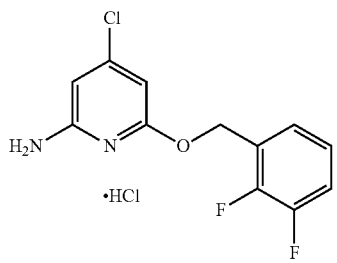

4-Chloro-6-((2,3-difluorobenzyl)oxy)pyridin-2-aminehydrochloride (68)

Compound 68 (pale yellow solid, 72 mg, 0.266 mmol, 73%) was prepared from 2,4-dichloro-6-(2,5-dimethyl-1H-pyrrol-1-yl)pyridine according to General Procedure G. $^1$H NMR (500 MHz, CD$_3$OD): δ 7.32-7.15 (m, 3H), 7.04 (s, 1H), 6.87 (s, 1H), 6.00 (s, 1H), 4.88 (s, 1H). $^{13}$C NMR (126 MHz, CD$_3$OD): 163.2, 157.6, 150.5 (dd, $J_{C-F}$=248.2, 12.6 Hz), 149.2 (dd, $J_{C-F}$=248.2, 12.6 Hz), 139.3, 132.7 (d, $J_{C-F}$=10.1 Hz), 126.2 (dd, $J_{C-F}$=7.6, 3.8 Hz), 124.5 (t, $J_{C-F}$=3.8 Hz), 118.3 (d, $J_{C-F}$=17.6 Hz), 111.5, 109.0, 68.5. LRMS (ESI) Calcd for C$_{12}$H$_{10}$ClF$_2$N$_2$O [(M+H)$^+$]: 271.04, found: 271.72.

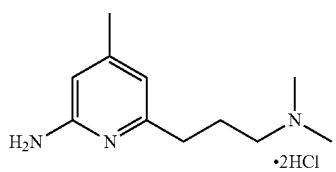

6-(3-(Dimethylamino)propyl)-4-methylpyridin-2-amine hydrochloride (69)

Compound 69 (brown solid, 172 mg, 0.890 mmol, 84%) was prepared from 81 according to General Procedure H. $^1$H NMR (500 MHz, CD$_3$OD): δ 6.72 (s, 2H), 3.28-3.20 (m, 2H), 2.93 (s, 6H), 2.84 (t, J=7.8 Hz, 2H), 2.38 (s, 3H), 2.22-2.16 (m, 2H). $^{13}$C NMR (126 MHz, CD$_3$OD): δ 159.1, 155.9, 148.5, 114.9, 111.3, 57.7 (2×C), 43.6, 30.3, 24.7, 22.0. LRMS (ESI) Calcd for C$_{11}$H$_{20}$N$_3$ [(M+H)$^+$]: 194.17, found: 195.42.

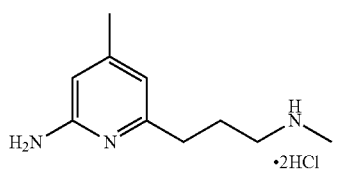

4-Methyl-6-(3-(methylamino)propyl)pyridin-2-amine hydrochloride (70)

Compound 70 (brown solid, 202 mg, 1.13 mmol, 89%) was prepared from 81 according to General Procedure H. $^1$H NMR (500 MHz, CD$_3$OD): δ 6.69 (s, 1H), 6.68 (s, 1H), 3.13-3.04 (m, 2H), 2.92 (s, NH, 1H), 2.86-2.82 (m, 2H), 2.73 (s, 3H), 2.38 (s, 3H), 2.14-2.07 (m, 2H). $^{13}$C NMR (126 MHz, CD$_3$OD): δ 159.2, 156.0, 148.7, 114.8, 111.3, 49.2, 33.6, 30.4, 26.0, 22.0. LRMS (ESI) Calcd for C$_{10}$H$_{18}$N$_3$ [(M+H)$^+$]: 180.15, found: 180.50.

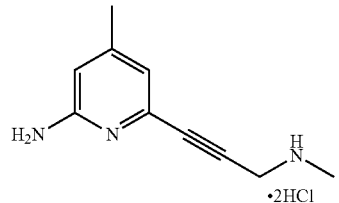

4-Methyl-6-(3-(methylamino)prop-1-yn-1-yl)pyridin-2-amine hydrochloride (71)

Compound 71 (brown solid, 172 mg, 0.890 mmol, 84%) was prepared from 81 according to General Procedure H. $^1$H NMR (500 MHz, CD$_3$OD): δ 6.72 (s, 2H), 3.28-3.20 (m, 2H), 2.93 (s, 6H), 2.84 (t, J=7.8 Hz, 2H), 2.38 (s, 3H), 2.22-2.16 (m, 2H). $^{13}$C NMR (126 MHz, CD$_3$OD): δ 159.1, 155.9, 148.5, 114.9, 111.3, 57.7 (2×C), 43.6, 30.3, 24.7, 22.0. LRMS (ESI) Calcd for C$_{10}$H$_{14}$N$_3$ [(M+H)$^+$]: 176.12, found: 177.52.

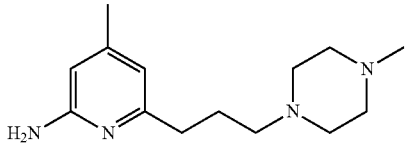

4-Methyl-6-(3-(4-methylpiperazin-1-yl)propyl)pyridin-2-amine (72)

Compound 72 (brown solid, 163 mg, 0.656 mmol, 80%) was prepared from 81 according to General Procedure H. $^1$H NMR (500 MHz, CDCl$_3$): δ 6.34 (s, 1H), 6.14 (s, 1H), 4.27 (s, 2H), 2.73-2.33 (m, 11H), 2.27 (s, 3H), 2.18 (s, 4H), 1.88-1.82 (m, 2H). $^{13}$C NMR (126 MHz, CDCl$_3$): δ 160.3, 158.2, 149.1, 114.4, 106.4, 58.3, 55.3, 53.3, 46.2, 36.0, 27.1, 21.0. LRMS (ESI) Calcd for C$_{14}$H$_{25}$N$_4$ [(M+H)$^+$]: 249.21, found: 250.09.

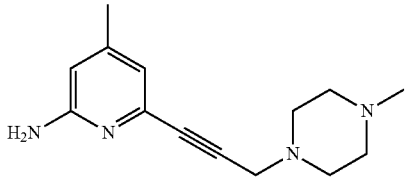

4-Methyl-6-(3-(4-methylpiperazin-1-yl)prop-1-yn-1-yl)pyridin-2-amine (73)

Compound 73 (off-white solid, 240 mg, 0.982 mmol, 92%) was prepared from 81 according to General Procedure H. ¹H NMR (500 MHz, CDCl₃): δ 6.62 (s, 1H), 6.22 (d, J=1.5 Hz, 1H), 3.50 (s, 2H), 2.82-2.32 (m, 8H), 2.27 (s, 3H), 2.15 (s, 3H). ¹³C NMR (126 MHz, CDCl₃): δ 158.4, 148.9, 140.6, 119.1, 108.8, 85.4, 83.1, 55.1, 52.0, 47.6, 46.1, 20.8. LRMS (ESI) Calcd for $C_{14}H_{21}N_4$ [(M+H)⁺]: 245.18, found: 246.10.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound of a Formula (I) or a salt or solvate thereof:

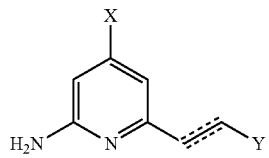

(I)

where X is hydrogen, $C_1$-$C_6$-alkyl, $C_1$-$C_6$-alkoxy, halogen, or haloalkyl, ===== represents a single, double, or triple bond;

Y is aryl substituted with halogen and a substituent having a formula —Z—$R^a$; or Y is 7-10 membered heteroaryl substituted at one or more ring positions with a substituent having a formula —Z—$R^a$; or Y has a formula —Z—$R^a$;

Z is selected from $C_1$-$C_6$-alkyl, $C_2$-$C_6$-alkenyl, and $C_2$-$C_6$-alkynyl;

$R^a$ is selected from alkylamino, dialkylamino, and a 4-6 membered heterocycle which contains at least one nitrogen atom and which heterocycle is optionally substituted at one or more positions with alkyl, alkoxy, or halogen; and wherein if Y is aryl substituted with one halogen and one substituent having a formula —$C_1$-$C_6$-alkyl-$R^a$, then $R^a$ is the 4-6 membered heterocycle which contains at least one nitrogen atom and which heterocycle is optionally substituted at one or more positions with alkyl, alkoxy, or halogen.

2. The compound of claim 1, wherein $R^a$ is selected from pyrrolidinyl which optionally is substituted at one or more positions with alkyl or alkoxy or halogen, azetinyl which optionally is substituted at one or more positions with alkyl, morpholinyl optionally substituted at one or more position with alkyl, and piperazinyl optionally substituted at one or more positions with alkyl.

3. The compound of claim 1 of a Formula (Ia):

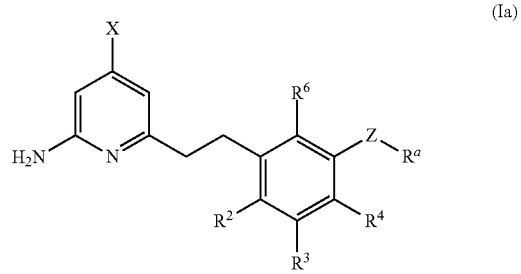

(Ia)

wherein $R^2$, $R^3$, $R^4$, and $R^6$, are each independently H or halogen; and at least one of $R^2$, $R^3$, $R^4$, and $R^6$ is halogen.

4. The compound of claim 3, wherein $R^3$ is halogen.

5. The compound of claim 3, wherein $R^2$ is halogen.

6. The compound of claim 3, wherein $R^2$ is halogen and $R^3$ is halogen.

7. The compound of claim 1, wherein Z is $CH_2$.

8. The compound of claim 1, wherein R is dimethylamino.

9. The compound of claim 1 of a Formula (IIb):

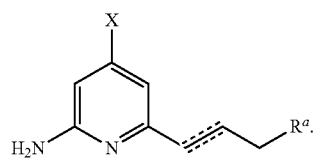

10. The compound of claim 1 of a formula:

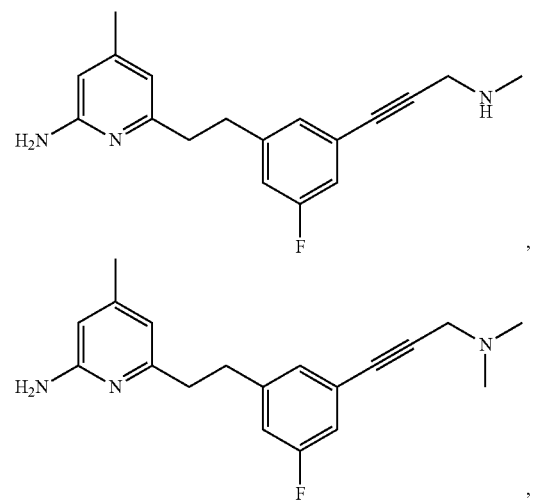

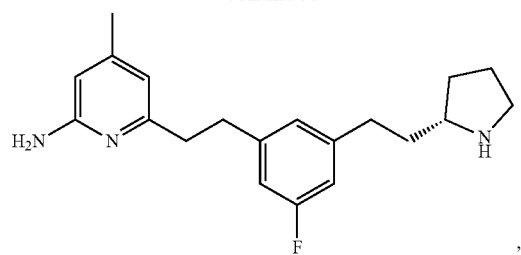
,
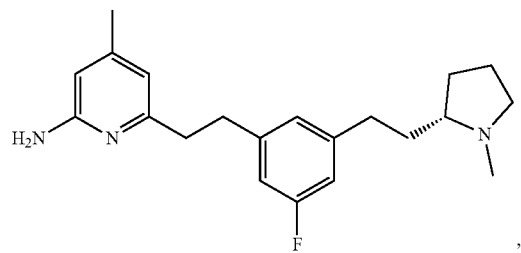
,
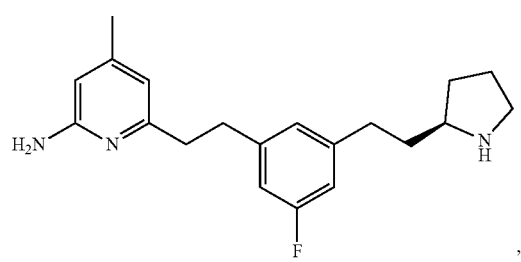
,
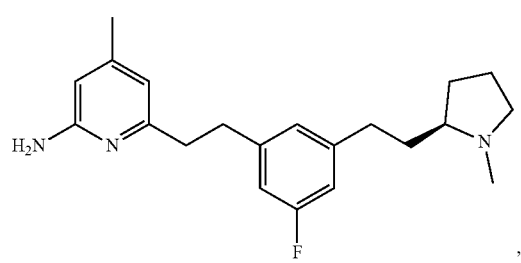
,
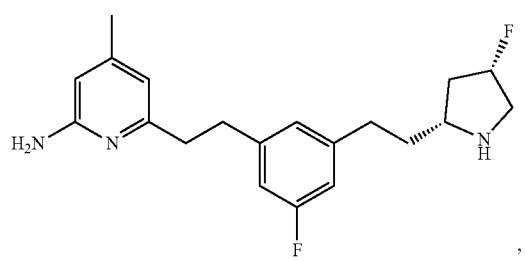
,
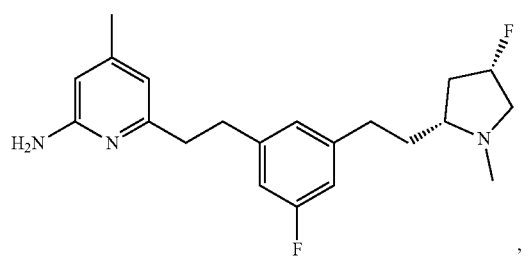
,
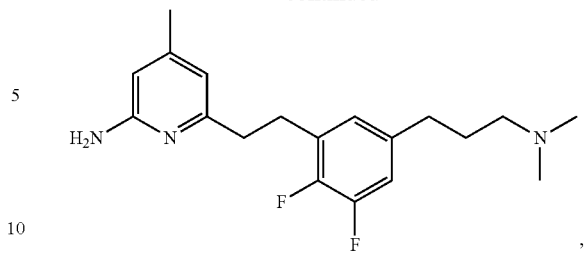
,
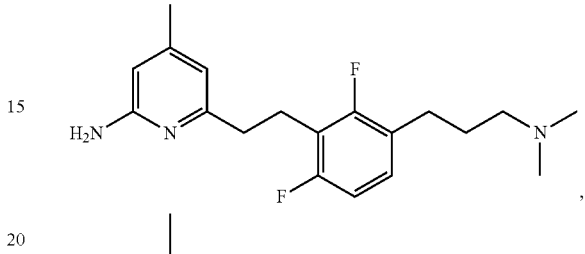
,
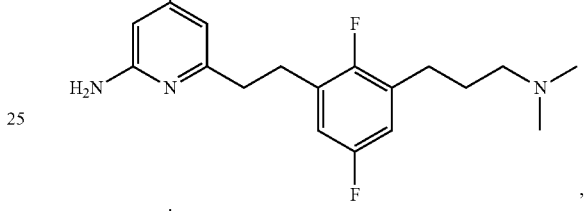
,
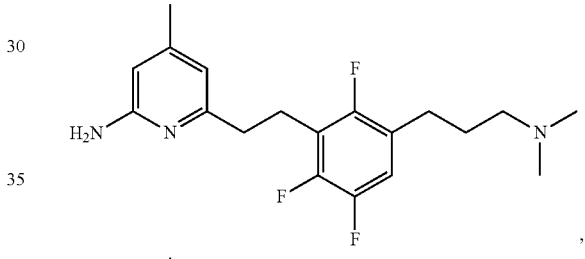
,
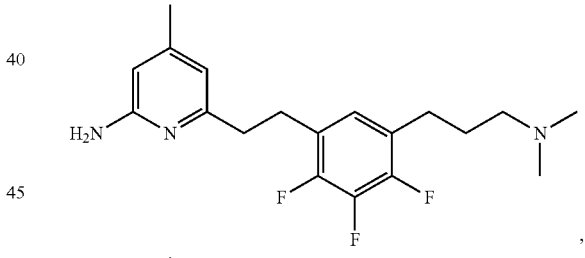
,
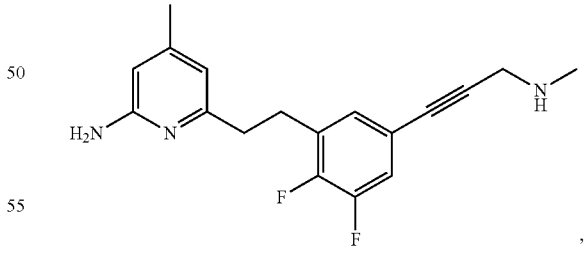
,
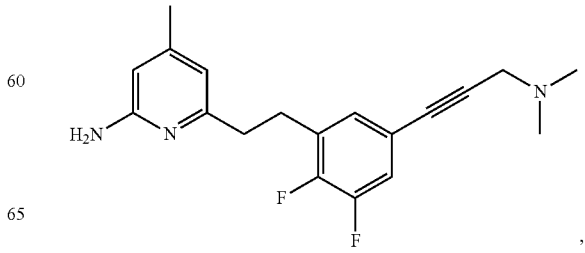
, 115
-continued
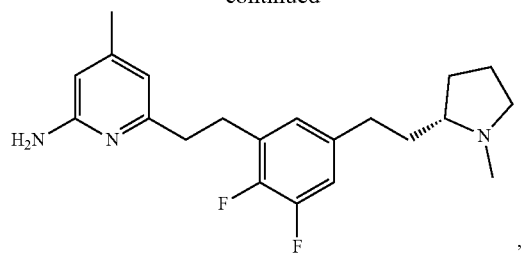
,
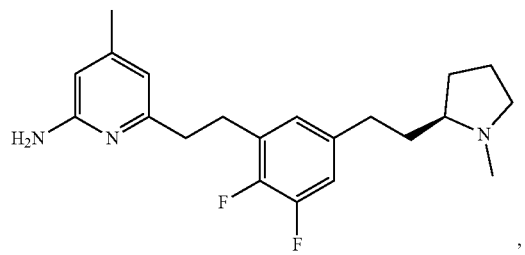
,
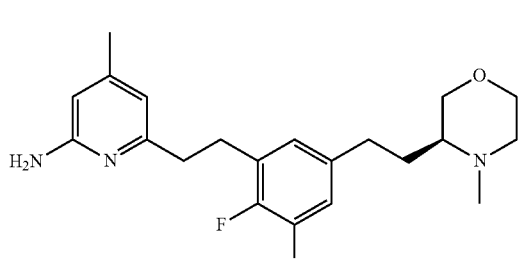
,
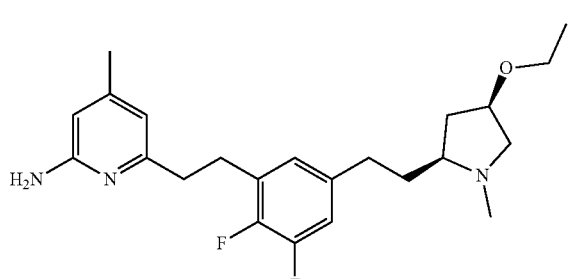
,
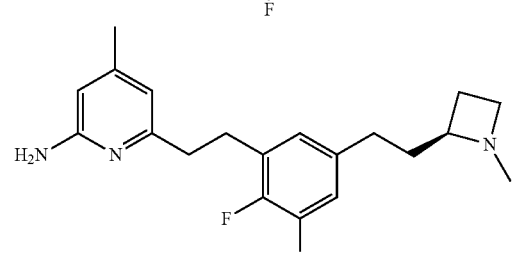
,
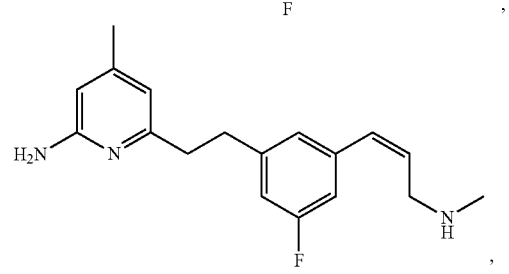
,
116
-continued
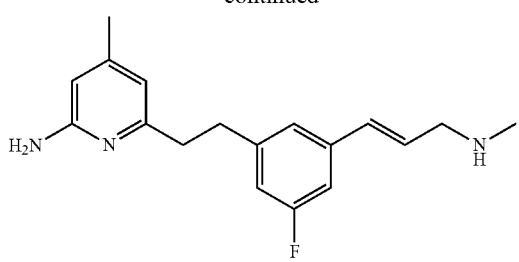
,
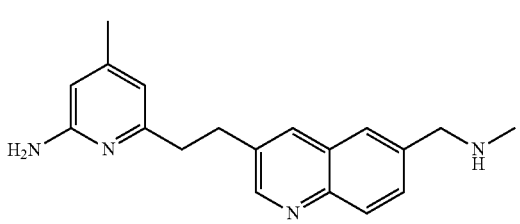
,
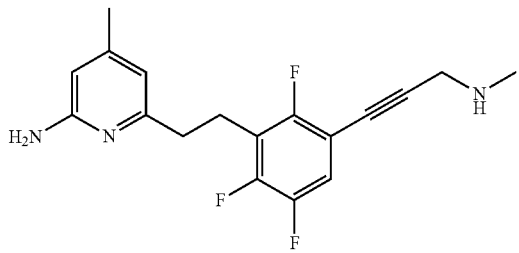
,
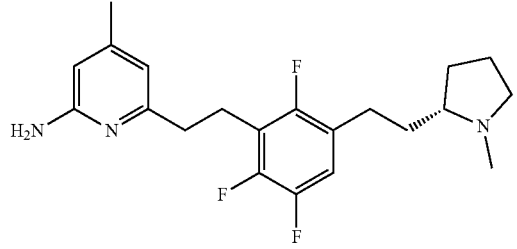
,
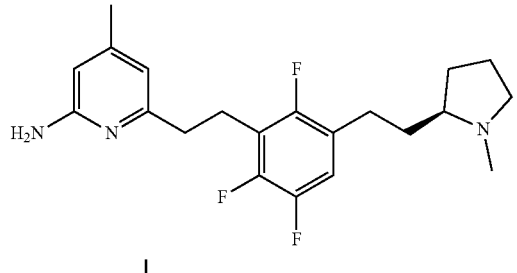
,
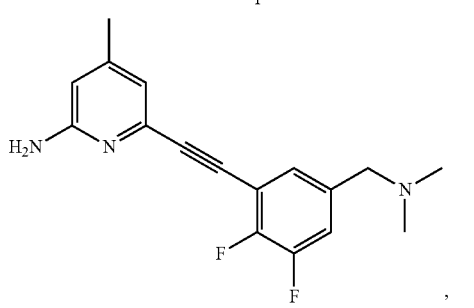
, 117
-continued
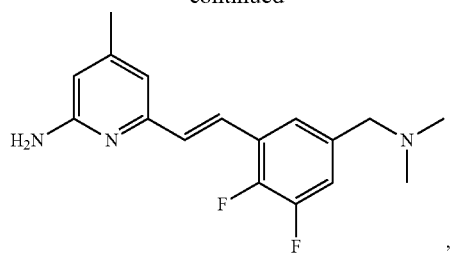
,
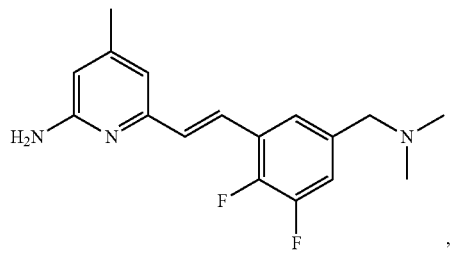
,
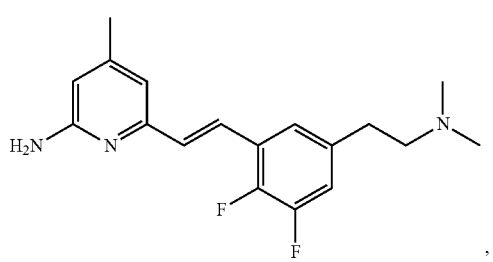
,
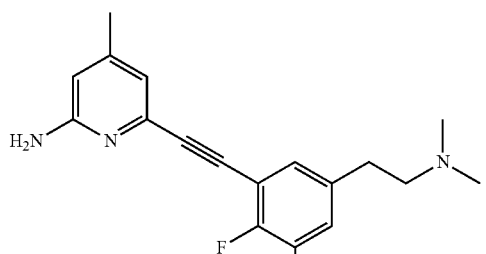
,
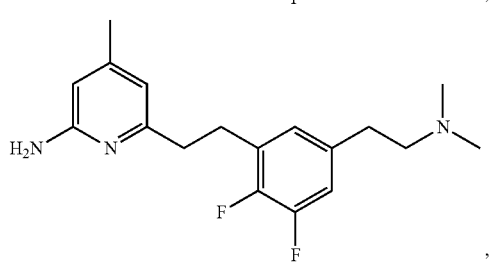
,
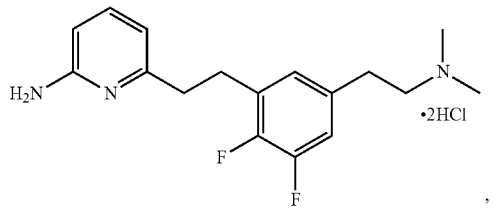
,
118
-continued
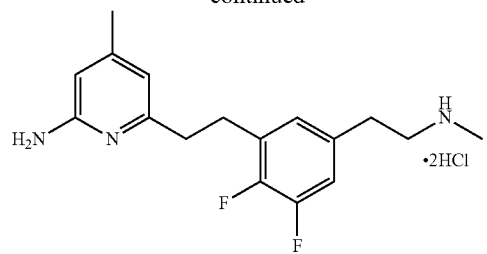
,
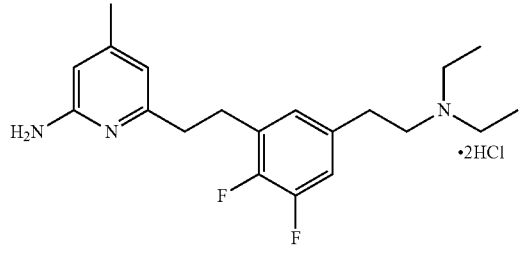
,
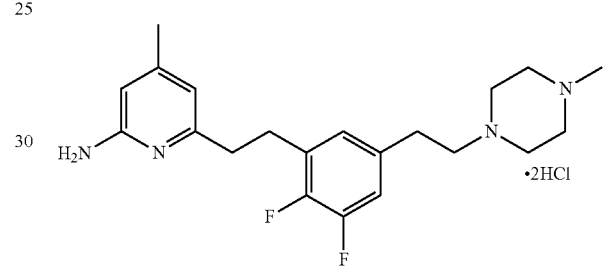
,
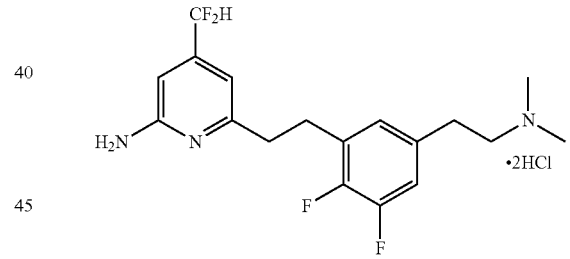
,
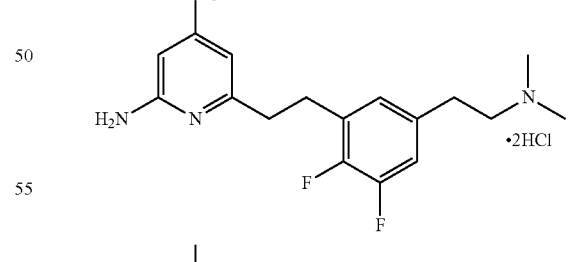
,
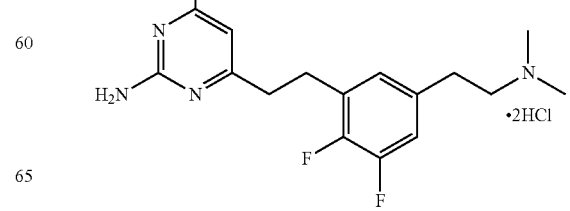
,

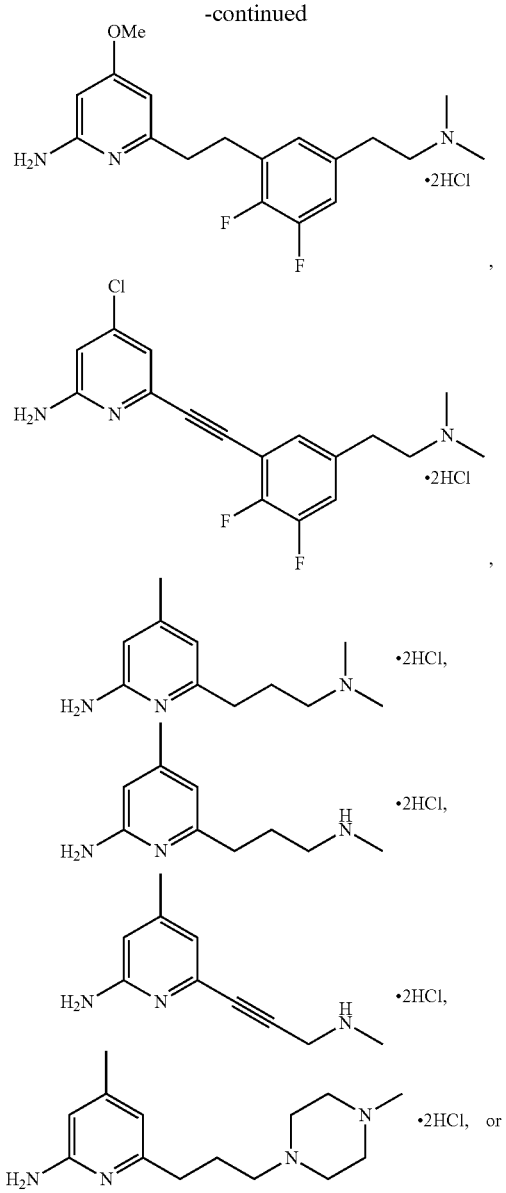

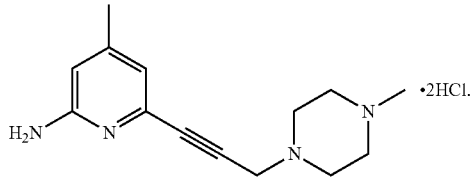

11. The compound of claim 1, wherein the compound has an effective permeability $P_e$ for the blood brain barrier of at least about $8\times10^{-6}$ cm/s.

12. The compound of claim 1, wherein the compound has a selectivity for nNOS versus iNOS of at least about 30.

13. The compound of claim 1, wherein the compound has a selectivity for nNOS versus eNOS of at least about 1000.

14. A pharmaceutical composition comprising the compound of claim 1 and a pharmaceutically acceptable carrier.

15. A method of treating a disease or disorder associated with nitric oxide synthase in a subject in need thereof, the method comprising administering to the subject an effective amount of the compound of claim 1.

16. The method of claim 15, wherein the disease or disorder is a neurodegenerative disease or disorder.

17. The method of claim 15, wherein the disease or disorder is Alzheimer's disease.

18. The method of claim 15, wherein the disease or disorder is Huntington's disease.

19. The method of claim 15, wherein the disease or disorder is Parkinson's disease.

20. The method of claim 15, wherein the disease or disorder is amyotrophic lateral sclerosis (ALS).

21. The method of claim 15, wherein the disease or disorder is cerebral palsy.

22. The method of claim 15, wherein the disease or disorder is a migraine headache.

23. A method of inhibiting nitric oxide synthase (NOS) in a cell, the method comprising contacting the cell with the compound of claim 1.

* * * * *